(12) United States Patent
Boden et al.

(10) Patent No.: US 11,389,531 B2
(45) Date of Patent: Jul. 19, 2022

(54) METHODS AND APPARATUS FOR THE DELIVERY OF HEPATITIS B VIRUS (HBV) VACCINES

(71) Applicants: Janssen Sciences Ireland Unlimited Company, County Cork (IE); Ichor Medical Systems, Inc., San Diego, CA (US)

(72) Inventors: Daniel Boden, San Mateo, CA (US); Helen Horton, Mol (BE); Jean-Marc Edmond Fernand Marie Neefs, Lier (BE); Soumitra Roy, Townsend, DE (US); Andrew W. Hannaman, San Diego, CA (US); Robert M. Bernard, Las Vegas, NV (US); Stephen A. Morse, Woodinville, WA (US); Oliver Ruck, Lewisville, TX (US); Adam Hartman, Denton, TX (US); Thomas David Cox, Plano, TX (US); Dorien De Pooter, Veerle (BE)

(73) Assignees: Janssen Sciences Ireland Unlimited Company, County Cork (IE); Ichor Medical Systems, Inc., San Diego, CA (US)

(*) Notice: Subject to any disclaimer, the term of this patent is extended or adjusted under 35 U.S.C. 154(b) by 580 days.

(21) Appl. No.: 16/223,318

(22) Filed: Dec. 18, 2018

(65) Prior Publication Data
US 2019/0184010 A1 Jun. 20, 2019

Related U.S. Application Data

(60) Provisional application No. 62/607,430, filed on Dec. 19, 2017.

(51) Int. Cl.
*A61K 39/29* (2006.01)
*C12N 7/00* (2006.01)
(Continued)

(52) U.S. Cl.
CPC .......... *A61K 39/292* (2013.01); *A61B 17/205* (2013.01); *A61N 1/0502* (2013.01);
(Continued)

(58) Field of Classification Search
CPC ...... A61M 37/0092; A61M 2037/0007; A61M 5/46; A61M 5/20; A61M 5/2033;
(Continued)

(56) References Cited

U.S. PATENT DOCUMENTS 4,727,138 A 2/1988 Goeddel
4,738,927 A 4/1988 Taniguchi
(Continued)

FOREIGN PATENT DOCUMENTS

JP H10500017 1/1998
KR 20080015211 A 2/2008
(Continued)

OTHER PUBLICATIONS

Boukhebza et al., "Comparative analysis of immunization schedules using a novel adenovirus-based immunotherapeutic targeting hepatitis B in naïve and tolerant mouse models" Vaccine, 32(26), pp. 3258-3263, 2014.
(Continued)

*Primary Examiner* — Kevin C Sirmons
*Assistant Examiner* — Alexandra Lalonde
(74) *Attorney, Agent, or Firm* — Ice Miller LLP

(57) ABSTRACT

Methods and apparatus for the reproducible, consistent and efficacious delivery of an HBV vaccine to a subject. The disclosure comprises apparatus for the controlled administration of the HBV vaccine through an orifice to the subject, a plurality of penetrating electrodes arranged with a predetermined spatial relationship relative to the orifice, and an
(Continued)

electrical signal generator operatively connected to the electrodes.

23 Claims, 31 Drawing Sheets

Specification includes a Sequence Listing.

(51) Int. Cl.
*A61P 31/20* (2006.01)
*A61N 1/32* (2006.01)
*A61N 1/05* (2006.01)
*A61B 17/20* (2006.01)
*C12N 15/82* (2006.01)
*C12N 15/86* (2006.01)
*A61K 39/00* (2006.01)
*A61N 1/30* (2006.01)

(52) U.S. Cl.
CPC ............. *A61N 1/325* (2013.01); *A61N 1/327* (2013.01); *A61P 31/20* (2018.01); *C12N 7/00* (2013.01); *C12N 15/8206* (2013.01); *C12N 15/86* (2013.01); *A61K 2039/53* (2013.01); *A61K 2039/54* (2013.01); *A61N 1/306* (2013.01); *C12N 2730/10111* (2013.01); *C12N 2730/10134* (2013.01); *C12N 2730/10171* (2013.01)

(58) Field of Classification Search
CPC .............. A61M 5/2448; A61M 5/2455; A61M 5/31568; A61M 5/3202; A61M 5/425; A61M 2005/206; A61M 2005/208; A61M 2005/2086; A61M 2005/2481; A61M 2005/31588; A61M 2005/2073; A61M 2005/2403; A61M 2005/2407; A61M 2005/2414; A61M 2005/244; A61M 2005/2026; A61M 2005/2411; A61M 2005/2433; A61M 2005/2347; A61M 2005/2485; A61M 37/00; A61M 37/0076; A61M 2205/13; A61M 2205/14; A61M 2205/18; A61M 2205/3306; A61M 2205/3313; A61M 2205/332; A61M 2205/50; A61M 2205/505; A61M 2205/581; A61M 2205/582; A61M 2205/586; A61M 2205/6009; A61M 2205/8206; A61M 2205/27; A61M 2205/12; A61M 2205/123; A61M 2205/19; A61M 2209/086; A61M 5/24; A61M 5/2422; A61M 5/2429; A61M 5/28; A61M 5/281; A61M 5/3134; A61M 5/31571; A61M 2202/30; A61M 2202/00; A61N 1/0428; A61N 1/18; A61N 1/325; A61N 1/306; A61N 1/0502; A61N 1/0504; A61N 1/30; A61N 1/20; A61N 1/32; A61N 1/327; A61N 1/0448; A61N 1/0412; A61N 1/08; A61N 1/303; A61K 39/292; A61P 31/20; A61B 17/205; A61B 17/20; A61B 2018/0016; A61B 2018/00196; C12N 15/8206; C12N 15/86; C12N 2730/10111

See application file for complete search history.

(56) References Cited

U.S. PATENT DOCUMENTS

| | | |
|---|---|---|
| 4,762,791 A | 8/1988 | Goeddel |
| 4,810,643 A | 3/1989 | Souza |
| 4,892,743 A | 1/1990 | Leibowitz |
| 4,966,843 A | 10/1990 | McCormick |
| 4,999,291 A | 3/1991 | Souza |
| 5,017,691 A | 5/1991 | Lee |
| 5,116,742 A | 5/1992 | Cech |
| 5,225,337 A | 7/1993 | Robertson |
| 5,246,921 A | 9/1993 | Reddy |
| 5,273,525 A | 12/1993 | Hofmann |
| 5,780,036 A | 7/1998 | Chisari |
| 5,873,549 A | 2/1999 | Lane et al. |
| 5,873,849 A | 2/1999 | Bernard |
| 5,958,060 A | 9/1999 | Premerlani |
| 6,041,252 A | 3/2000 | Walker |
| 6,110,161 A | 8/2000 | Mathiesen |
| 6,117,660 A | 9/2000 | Walters |
| 6,224,879 B1 | 5/2001 | Sjoeberg |
| 6,261,281 B1 | 7/2001 | Mathiesen |
| 6,273,525 B1 | 8/2001 | Erban |
| 6,278,895 B1 | 8/2001 | Bernard |
| 6,319,901 B1 | 11/2001 | Bernard |
| 6,697,669 B2 | 2/2004 | Dev |
| 6,873,549 B2 | 3/2005 | Khalid |
| 6,873,849 B2 | 3/2005 | De La Red |
| 6,912,417 B1 | 6/2005 | Bernard |
| 6,939,862 B2 | 9/2005 | Bureau |
| 6,958,060 B2 | 10/2005 | Mathiesen |
| 6,982,087 B2 | 1/2006 | Johnston |
| 7,328,064 B2 | 2/2008 | Mathiesen |
| 7,419,674 B2 | 9/2008 | Chulay |
| 7,664,545 B2 | 2/2010 | Westersten |
| 7,850,977 B2 | 12/2010 | Kamrud |
| 8,080,255 B2 | 12/2011 | Smith |
| 8,187,249 B2 | 5/2012 | Bernard |
| 8,209,006 B2 | 6/2012 | Smith |
| 8,216,589 B2 | 7/2012 | Yum |
| 8,859,198 B2 | 10/2014 | Bartholomeusz |
| 8,961,995 B2 | 2/2015 | Frolov |
| 9,364,664 B2 | 6/2016 | Masterson |
| 9,452,285 B2 | 9/2016 | Draghia-Akli |
| 9,801,897 B2 | 10/2017 | Geall |
| 9,802,035 B2 | 10/2017 | Masterson |
| 10,538,786 B2 | 1/2020 | Kamrud |
| 11,020,476 B2 | 6/2021 | Boden |
| 11,021,692 B2 | 6/2021 | Boden |
| 11,185,688 B2 | 11/2021 | Hannaman |
| 2004/0213805 A1 | 10/2004 | Verheije |
| 2004/0235133 A1 | 11/2004 | Frolov |
| 2005/0070700 A1 | 3/2005 | Giese |
| 2005/0277605 A1 | 12/2005 | Wu |
| 2008/0279891 A1 | 11/2008 | Johnston |
| 2009/0018031 A1 | 1/2009 | Trinklein |
| 2009/0075384 A1 | 3/2009 | Kamrud |
| 2011/0110974 A1 | 5/2011 | Depla |
| 2012/0078161 A1* | 3/2012 | Masterson ............. A61N 1/325 604/21 |
| 2012/0121650 A1 | 5/2012 | Johnston |
| 2014/0079734 A1 | 3/2014 | Frolov |
| 2014/0222105 A1* | 8/2014 | Broderick ............ A61N 1/0476 607/59 |
| 2015/0328404 A1* | 11/2015 | Murakami ............ A61M 5/347 604/67 |
| 2016/0074500 A1 | 3/2016 | Pushko |
| 2016/0166678 A1 | 6/2016 | Kallen |
| 2016/0362472 A1 | 12/2016 | Bitter |
| 2017/0314043 A1 | 11/2017 | Kamrud |
| 2018/0104359 A1 | 4/2018 | Kamrud |
| 2018/0171340 A1 | 6/2018 | Kamrud |
| 2020/0164062 A1 | 5/2020 | Goh |

FOREIGN PATENT DOCUMENTS

| | | |
|---|---|---|
| WO | 8502862 | 7/1985 |
| WO | 8504188 | 9/1985 |
| WO | 9006370 | 6/1990 |
| WO | 9503777 A1 | 2/1995 |
| WO | 9531565 | 11/1995 |
| WO | 9637616 | 11/1996 |
| WO | 200224224 A2 | 3/2002 |
| WO | 2002042480 A2 | 5/2002 |

(56) References Cited

FOREIGN PATENT DOCUMENTS

| | | |
|---|---|---|
| WO | 2004055161 A2 | 7/2004 |
| WO | 2005087311 A1 | 9/2005 |
| WO | 2008/020656 A1 | 2/2008 |
| WO | 2008093976 A1 | 8/2008 |
| WO | 2011015656 A2 | 2/2011 |
| WO | 2012/006376 A2 | 1/2012 |
| WO | 2012087983 | 6/2012 |
| WO | 2012/109404 A1 | 8/2012 |
| WO | 2012109668 A1 | 8/2012 |
| WO | 2013007772 A1 | 1/2013 |
| WO | 2014170493 A2 | 10/2014 |
| WO | 2016020538 A1 | 2/2016 |
| WO | 2016054003 A1 | 4/2016 |
| WO | 2016184822 A1 | 11/2016 |
| WO | 2017024000 A1 | 2/2017 |
| WO | 2017/076988 A1 | 5/2017 |
| WO | 2017172838 A1 | 10/2017 |
| WO | 2017176319 A1 | 10/2017 |
| WO | 2017180770 A1 | 10/2017 |
| WO | 2018075235 A1 | 4/2018 |
| WO | 2018106615 A1 | 6/2018 |
| WO | 2018/189522 A1 | 10/2018 |
| WO | 2018/225731 A1 | 12/2018 |
| WO | 2018225731 A1 | 12/2018 |
| WO | 2019/099624 A1 | 5/2019 |
| WO | 2019099624 A1 | 5/2019 |
| WO | 2019/123250 A1 | 6/2019 |
| WO | 2019/126120 A1 | 6/2019 |
| WO | 2019123252 A1 | 6/2019 |

OTHER PUBLICATIONS

Jones et al., "Hepatitis B virus reverse transcriptase: diverse functions as classical and emerging targets for antiviral intervention", Emerging Microbes and Infections, 2(9), e56, 9 pages, 2013.

Obeng-Adjel et al. "DNA vaccine cocktail expressing genotype A and C HBV surface and consensus core antigens generates robust cytotoxic and antibody responses and mice and Rhesus macaques" Cancer Gene Therapy, 20, 652-662 2013.

World Health Organization, Hepatitis B: Fact sheet No. 204 [Internet] Mar. 2015. Available from https://www.who.int/news-room/fact-sheets/detail/hepatitis-b.

Int'l Search Report and Written Opinion dated Jun. 25, 2018 in Int'l Application No. PCT/US2017/067269.

Int'l Search Report and Written Opinion dated Feb. 14, 2019 in Int'l Application No. PCT/US2018/066157.

Bartenschlager et al., "Expression of the P-protein of the human hepatitis B virus in a vaccinia virus system and detection of the nucleocapsid-associated P-gene product by radiolabelling at newly introduced phosphorylation sites", Nucleic Acids Research, vol. 20, No. 2, pp. 195-202,1992.

Perrine Martin et al, "TG1050, an immunotherapeutic to treat chronic hepatitis B, induces robust T cells and exerts an antiviral effect in HBV-persistent mice", GUT, UK, (Nov. 26, 2014), vol. 64, No. 12, doi:10.1136/gutjnl-2014-308041, ISSN 0017-5749, pp. 1961-1971, XP055453477.

Ramirez et at., "Biology of Attenuated Modified Vaccinia Virus Ankara Recombinant Vector in Mice: Virus Fate and Activation of B- and T-Cell Immune Responses in Comparision with the Western Reserve Strain and advantages as a Vaccine", Journal of Virology, Vo. 74, No. 2, pp. 923-933, 2000.

Reyes-Sandoval Arturo et al, "Prime-Boost Immunization with Adenoviral and Modified Vaccinia Virus Ankara Vectors Enhances the Durability and Polyfunctionality of Protective Malaria CD8(+) T-Cell Responses", Infection and Immunity, (Jan. 2010), vol. 78, No. 1, pp. 145-153, XP002778539.

Van Marie et al., Arterivirus discontinuous mRNA transcription is guided by base pairing between sense and antisense transcription-regulating sequences, Pro. Natl. Acad. Sci. USA, Aug. 6, 1999, pp. 12056-12061, vol. 96, Issue 21.

Van Marie, et al., Characterization of an Equine Arteritis Virus Replicase Mutant Defective in Subgenomic mRNA Synthesis, J. Virol., 1999, pp. 5274-5281, vol. 73, Issue 7.

Obeng-Adjei et al., "Synthetic DNA immunogen encoding hepatitis B core antigen drives immune response in liver," Cancer Gene Therapy, 2012, 19:779-787.

Agapov et al., Noncytopathic Sindbis Virus RNA Vectors for Heterologous Gene Expression, Proc. Natl. Acad. Sci., 1998, pp. 12989-12994, vol. 95.

Altmann et al., Cotransfection of ICAM-1 and HLA-DR Reconstitutes Human Antigen-Presenting Cell Function in Mouse L Cells, Nature, 1989, pp. 512-514, vol. 338.

Altschul SF et al., "Basic Local Alignment Search Tool"; J. Mol. Biol. 215:403-410 (1990).

Araujo et al., "Expression of Hepatitis B virus surface antigen (HBsAg) from genotypes A, D and F and influence of amino acid variations related or not to genotypes on HBsAg detection," Brazilian Journal of Infectious Diseases, Jan. 1, 2009, vol. 13, Nr: 4.

Atkins, G, et al. Therapeutic and Prophylactic Applications of Alphavirus Vectors, Expert Reviews in Molecular Medicine, Cambridge University Press, vol. 10, No. 1, pp. 1-18 (2008).

Attwood, T. The Babel of Bioinformatics, Science (2000) vol. 290, No. 5491, pp. 471-473 (Year: 2000).

Baker et al., Protein Structure Predication and Structural Genomics, Science (2001) vol. 294, No. 5540, pp. 93-96 (Year: 2001).

Barbieri et al., Purification and partial characterization of another form of the antiviral protein from the seeds of *Phytolacca americana* L. (pokeweed), Biochem. J., 1982, pp. 55-59, vol. 203.

Barrette-Ng et al., Structure of Arterivirus nsp-4, J. Biol. Chem., 2002, pp. 39960-39966, vol. 277, Issue 42.

Beerens & Snijder, An RNA Pseudoknot in the 3' End of the Arterivirus Genome Has a Critical Role in Regulating Viral RNA Synthesis, J. Virol., 2007, pp. 9426-9436, vol. 81, Issue 17.

Belloni et al. "IFN-a inhibits HBV transcription and replication in cell culture and in humanized mice by targeting the epigenetic regulation of the nuclear cccDNA minichromosome" J. Clin. Invest., 122(2), 529-537, 2012.

Berglund, P. et al., Enhancing Immune Response Using Suicidal DNA Vaccines,, Nature Biotechnology, vol. 16, pp. 562-565 (1998).

Besnard et al., Selection against expression of the *Escherichia coli* gene gpt in hprt+ mouse teratocarcinoma and hybrid cells, Mol. Cell. Biol., 1987, pp. 4139-4141, vol. 7.

Bolz et al.: "Use of Recombinant Virus Replicon Particles for Vaccination against *Mycobacterium ulcerans* Disease"; PLoS Negl Trop Dis,, Aug. 14, 2015, vol. 9(8):e0004011., PDF File: p. 1-18.

Brakenhoff et al., Molecular cloning and expression of hybridoma growth factor in *Escherichia coli*, J. Immunol., Dec. 15, 1987, pp. 4116-4121, vol. 139, Issue 12.

Bzik et al., Molecular cloning and sequence analysis of the Plasmodium falciparum dihydrofolate reductase-thymidylate synthase gene, Proc. Natl. Acad. Sci. USA, Dec. 1987, pp. 8360-8364, vol. 84.

Calderwood et al., Nucleotide sequence of the Shiga-like toxin genes of *Escherichia coli*, Proc. Natl. Acad. Sci. USA, Jul. 1987, pp. 4364-4368, vol. 84.

Carroll and Collier, Active Site of Pseudomonas aeruginosa Exotoxin A, J. Biol. Chem., 1987, pp. 8707-8711, vol. 262.

Castillo-Olivares et al., Generation of a Candidate Live Marker Vaccine for Equine Arteritis Virus by Deletion of the Major Virus Neutralization Domain, J. Virol., 2003, pp. 8470-8480, vol. 77, Issue 15.

Chen et al., The complete primary structure of abrin-a B chain. FEBS Letters, 1992, pp. 115-118, vol. 309.

Cheng, W. et al. Enhancement of Sindbis Virus Self-Replicating RNA Vaccine Potency by Linkage of *Mycobacterium* tuberculosis Heat Shock Protein 70 Gene to an Antigen Gene, Journal of Immunology, vol. 166, pp. 6218-6226 (2001).

Chin et al., Tissue-specific Expression of Hepatic Functions Genetic Aspects, Ann. N.Y. Acad. Sci., Oct. 1986, pp. 120-130, vol. 478.

Cohen et al. "Is chronic hepatitis B being undertreated in the United States?" J. Viral Hepat., 18(6), 377-83,2011.

(56) References Cited

OTHER PUBLICATIONS

Collins et al., Primary Amino Acid Sequence of α-Trichosanthin and Molecular Models for Abrin A-chain and α-Trichosanthin, J. Biol. Chem., 1990, pp. 8665-8669, vol. 265.
Coussens et al., Tyrosine kinase receptor with extensive homology to EGF receptor shares chromosomal location with neu oncogene, Science, 1985, pp. 1132-1139, vol. 230.
Davis, N. et al., In Vitro Synthesis of Infectious Venezuelan Equine Encephalitis Virus RNA from a cDNA Clone: Analysis of a Viable Deletion Mutant Virology, vol. 171, pp. 189-204 (1989).
De Vries et al., Genetic Manipulation of Equine Arteritis Virus Using Full-Length cDNA Clones: Separation of Overlapping Genes and Expression of a Foreign Epitope. Virology, 2000, pp. 84-97, vol. 270.
De Vries et al., Recombinant Equine Arteritis Virus Expression Vector, Virology, Jun. 5, 2001, pp. 259-276, vol. 284, Issue 2.
De Wilde et al., Cyclophilin Inhibitors Block Arterivirus Replication by Interfering with Viral RNA Synthesis, J. Virol., 2013, pp. 1454-1464, vol. 87, Issue 3.
Den Boon et al., Equine Arteritis Virus Subgenomic RNA Transcription: UV Inactivation and Translation Inhibition Studies, Virology, 1995, pp. 364-372, vol. 213.
Deng et al., Structural Basis for the Regulatory Function of a Complex Zinc-binding Domain in a Replicative Arterivirus Helicase Resembling a Nonsense-Mediated mRNA Decay Helicase, Nucl. Acids Res., 2013, pp. 3464-3477, vol. 42, Issue 5.
Ding et al., In Vivo Genome-Wide Profiling of RNA Secondary Structure Reveals Novel Regulatory Features, Nature, 2014, pp. 696-700 (and Methods), vol. 505.
Dowdy et al., Efficient Generation of Human iPSCs by a Synthetic Self-Replicative RNA, Cell Stem Cell, 2013, pp. 246-254, vol. 13.
Dubensky, T. et al. Sindbis Virus DNA-Based Expression Vectors: Utility for In Vitro and In Vivo Gene Transfer, Journal of Virology, vol. 70, No. 1, pp. 508-519 (1996).
Evensen et al., Direct Molecular Cloning and Expression of Two Distinct Abrin A-chains, J. Biol. Chem., Apr. 15, 1991, pp. 6848-6852, vol. 266, Issue 11.
Fainstein et al., Nucleotide sequence analysis of human abl and bcr-abl cDNAs, Oncogene, Dec. 1, 1989, pp. 1477-1481, vol. 4. Issue 12.
Faktor et al., The identification of hepatitis B virus X gene responsive elements reveals functional similarity of X and HTLV-I tax, Oncogene, Jun. 1, 1990, pp. 867-872, vol. 5, Issue 6.
Familletti et al., A convenient and rapid cytopathic effect inhibition assay for interferon, Methods in Enz., 1981, pp. 387-394, vol. 78.
Fang et al., Efficient-2 Frameshifting by Mammalian Ribosomes to Synthesize an Additional Arterivirus Protein, PNAS, 2012, pp. E2920-E2928.
Field et al., Isolation and Characterization of Acyclovir-Resistant Mutants of Herpes Simplex Virus, J. Genl. Virol., 1980, pp. 115-124, vol. 49.
Finter et al., The Use of Interferon-α in Virus Infections, Drugs, 1991, pp. 749-765, vol. 42.
Firth et al., Discovery of a Small Arterivirus Gene that Overlaps the GP5 Coding Sequence and is Important for Virus Production, J. Genl. Virol., 2011, pp. 1097-1106, vol. 92.
Foy, et al., "Hypervariable domains of nsP3 proteins of New World and Old World alphaviruses mediate formation of distinct, virus-specific protein complexes", J. Virol., vol. 87, No. 4, p. 1997-2010, (Dec. 2012).
Frolov et al, (Journal of Virology, 1999, p. 3854-3865).
Frolov, I et al., Translation of Sindbis Virus mRNA: analysis of sequences downstream of the initiating AUG codon that enhance translation. Journal of Virology, vol. 70, No. 2, pp. 1182-1190 (1996).
Frolov, I et al.Translation of Sindbis Virus mRNA: Effects of Sequences Downstream of the Initiating Codon, Journal of Virology, vol. 68, No. 12, pp. 8111-8117, (1994).

Frolov, I. et al. Cis-acting RNA elements at the 5' end of Sindbis virus genome RNA regulate minus- and plus-strand RNA synthesis, RNO, vol. 7, pp. 1638-1651 (2001).
Gansbacher et al., Interleukin 2 Gene Transfer into Tumor Cells Abrogates Tumorigenicity and Includes Protective Immunity, J. Ex. Med., The Rockefeller University Press, Oct. 1990, pp. 1217-1224, vol. 172.
Gansbacher et al., Retroviral Vector-mediated γ-Interferon Gene Transfer into Tumor Cells Generates Potent and Long Lasting Antitumor Immunity, Cancer Res., Dec. 15, 1999, pp. 7820-7825, vol. 50.
GenBank accession # JX473847, dated Dec. 22, 2012; accessed Apr. 17, 2019, 6 pages.
GenBank: KT121715.1: Accession KT121715, Version KT121715.1. 2015, Sindbis virus isolate Treatmant1_population9, complete genome (Year: 2015).
GenBank: L01443.1 Accession No. L01443, 2004, Venezuelan equine encephalitis virus strain TC-83, complete genome (Year: 2004).
GenBank/NCBI accession No. J02363, dated Oct. 25, 2000; accessed Jul. 16, 2018, 7 pages.
GenBank/NCBI accession No. L01443.1., dated Nov. 17, 2014; accessed Oct. 3, 2016, 7 pages.
GenBank/NCBI accession No. L04653, dated Jun. 1, 2001; accessed Jul. 16, 2018, 6 pages.
GenBank/NCBI accession No. NC_001449, dated Feb. 10, 2015; accessed Jul. 16, 2018, 7 pages.
GenBank/NCBI accession No. NC_003215, dated Feb. 10, 2015; accessed Jul. 16, 2018, 6 pages.
GenBank/NCBI accession No. U38304; dated Feb. 10, 2015; accessed Jul. 16, 2018, 5 pages.
GenBank/NCBI accession No. U38305, dated Jan. 30, 2016, accessed Jul. 16, 2018, 5 pages.
GenBank/NCBI accession No. X04129, dated Mar. 13, 2001; accessed Jul. 16, 2018, 5 pages.
Gibson et al., Enzymatic assembly of DNA molecules up to several hundred kilobases, Nature Methods, Apr. 12, 2009, pp. 343-345, vol. 6.
Glaser AL et al., An infectious cDNA clone of equine arteritis virus: a tool for future fundamental studies and vaccine development. Proceedings of the 8th International Conference on Equine Infectious Diseases, Dubai 1998; 1999, pp. 166-176.
Golumbek et al., Treatment of established renal cancer by tumor cells engineered to secrete interleukin-4, Science, Nov. 1, 1991, pp. 713-716, vol. 254.
Gorchakov, R. et al., Selection of Functional 5 cis-Acting Elements Promoting Efficient Sindbis Virus Genome Replication, Journal of Virology, vol. 78, No. 1, pp. 61-75 (2004).
Gotte, et al., "The Enigmatic Alphavirus Non-Structural Protein 3 (nsP3) Revealing Its Secrets at Last", Viruses, vol. 10, No. 3, p. 105, 1/26 to 26/26, (Feb. 2018).
Grabstein et al., Cloning of a T cell growth factor that interacts with the beta chain of the interleukin-2 receptor. Science, 1994, pp. 965-968, vol. 264.
Hardy, R. et al. Requirements at the 3 End of the Sindbis Virus Genome for Efficient Synthesis of Minus-Strand RNA, Journal of Virology, pp. 4630-4639 (2005).
Hooper et al., Molecular Smallpox Vaccine Delivered by Alphavirus Replicons Elicits Protective Immunity in Mice and Non-Human Primates, Vaccine, 2009, pp. 494-511, vol. 28, Issue 2.
Horikawa et al., Molecular cloning and nucleotide sequence of cDNA encoding the human liver S-adenosylmethionine synthetase, Biochem. Intl., Sep. 1, 1991, pp. 81-90, vol. 25, Issue 1.
Huang et al. Development of a vaccine vector based on a subgenomic replicon of porcine reproductive and respiratory syndrome virus. J Virol Methods. Sep. 2009;160(1-2):22-8. (Year: 2009).
Hyde, J. et al., The 5' and 3' ends of alphavirus RNAs—non-coding is not non-functional, Virus Res., vol. 206, pp. 99-107 (2015).
Int'l Search Report and Written Opinion dated Feb. 14, 2019 in Int'l Application No. PCT/US2018/066157, 19 pages.
Int'l Search Report and Written Opinion dated Mar. 26, 2018 in Int'l Application No. PCT/IB2017058148, 14 pages.

(56) References Cited

OTHER PUBLICATIONS

Int'l Search Report and Written Opinion dated Mar. 27, 2019 in Int'l Application No. PCT/IB2018/060257, 15 pages.
Int'l Search Report and Written Opinion dated Apr. 17, 2019 in Int'l Application No. PCT/IB2018/060259, 16 pages.
Int'l Search Report and Written Opinion dated May 22, 2018 in Int'l Application No. PCT/IB2017/058142, 17 pages.
Int'l Search Report and Written Opinion dated Jun. 25, 2018 in Int'l Application No. PCT/US2017/067269, 17 pages.
International Search Report and Written Opinion dated Dec. 13, 2019 in International Appl. No. PCT/US2019/055125, 15 pages.
International Search Report and Written Opinion, dated Dec. 1, 2017, in International Application No. PCT/US2017/054928, 18 pages.
International Search Report and Written Opinion, dated Jul. 10, 2017, in International Patent Application No. PCT/US2017/027249, filed Apr. 12, 2017, 16 pages.
International Search Report and Written Opinion, dated Jul. 3, 2018, in International Application No. PCT/US2017/064561, 22 pages.
International Search Report dated Apr. 23, 2019, regarding PCT/US2019/014210, 13 pages.
Irvin JD et al., Purification and properties of a second antiviral protein from Phytolacca americana which inactivates eukaryotic ribosomes, Arch. Biochem. & Biophys., Apr. 1, 1980, pp. 418-425, vol. 200, Issue 2.
Irvin JD, Pokeweed antiviral protein, Pharmac. Ther., 1983, pp. 371-387, vol. 21, Issue 3.
Irvin JD, Purification and partial characterization of the antiviral protein from Phytolacca americana which inhibits eukaryotic protein synthesis, Arch. Biochem & Biophys, Aug. 1975, pp. 522-528, vol. 169, Issue 2.
Jackson et al., Nucleotide sequence analysis of the structural genes for Shiga-like toxin I encoded by bacteriophage 933J from *Escherichia coli*. Microb. Path., Feb. 1987, pp. 147-153, vol. 2, Issue 2.
Jayaraman et al., Enhancement of in vivo cell-mediated immune responses by three distinct cytokines, J. Immunol., 1990, pp. 942-951, vol. 144.
Jeeva S, Lee JA, Park SY, Song CS, Choi IS, Lee JB. Development of porcine respiratory and reproductive syndrome virus replicon vector for foot-and-mouth disease vaccine. Clin Exp Vaccine Res. Jan. 2014;3(1):100-9. doi: 10.7774/cevr.2014.3.1.100. Epub Dec. 18, 2013. PMID: 24427767; PMCID: PMC3890444. (Year: 2014).
Johansson et al., 2012, PLOS ONE, Intradermal Electroporation of Naked Replicon RNA Elicits Strong Immune Responses, 7(1):e29732.
Kamrud et al., Alphavirus Replicon Approach to Promoterless Analysis of IRES Elements, Virology, 2007, pp. 376-387, vol. 360.
Karlin & Altschul, Applications and statistics for multiple high-scoring segments in molecular sequences Proc. Nat'l. Acad. Sci. USA 90:5873-87 (1993).
Karupiah et al., Elevated natural killer cell responses in mice infected with recombinant vaccinia virus encoding murine IL-2, J. Immunol., Jan. 1, 1990, pp. 290-298, vol. 144, Issue 1.
Kelly, B. et al. Potential of Alphavirus Vectors in the Treatment of Advanced Solid Tumors, Recent Patents on Anti-Drug Discovery, vol. 2, No. 2, pp. 159-166 (2007).
Kerr et al., Anti-penicillin-V-amidase conjugates kill antigen-positive tumor cells when combined with doxorubicin phenoxyacetamide, Cancer. Immunol. Immunother.,1990, pp. 202-206, vol. 31, Issue 4.
Kim et al. 2014. Enhancement of protein expression by alphavirus replicons by designing self-replicating subgenomic RNAs. Proceedings National Academy of Sciences, 111 (29):10708-10713.
Kim, et al., "New World and Old World Alphaviruses Have Evolved to Exploit Different Components of Stress Granules, FXR and G3BP Proteins, for Assembly of Viral Replication Complexes", PLOS Pathogens, vol. 12, No. 8, p. 1-31, (Aug. 2016).
Kinney, R. et al., Attenuation of Venezuelan Equine Encephalitis Virus Strain TC-83 Is Encoded by the 5'-Noncoding Region and the E2 Envelope Glycoprotein, Journal of Virology, vol. 67, No. 3, pp. 1269-1277, (1993).

Klimstra et al., Adaptation of Sindbis Virus to BHK Cells Selects for Use of Heparan Sulfate as an Attachment Receptor. J. Virol. 72: pp. 7357 (1988), 10 pages.
Knoops et al., Ultrastructural Characterization of Arterivirus Replication Structures: Reshaping the Endoplasmic Reticulum to Accommodate Viral RNA Synthesis, J. Virol., 2011, pp. 2474-2487, vol. 86, Issue 5.
Kofler R. et al., Mimicking live flavivirus immunization with a noninfectious RNA vaccine, PNAS, vol. 101, No. 7, pp. 1951-1956, (2004).
Kulasegaran-Shylini et al., Structural and Functional Elements of Promoter Encoded by the 5' Untranslated Region of the Venezuelan Equine Encephalitis Virus Genome J. Virol. 83:17 p. 8327-8339 (2009).
Kulasegaran-Shylini et al., The 5'UTR-specific mutation in VEEV TC-83 genome has a strong effect on RNA replication and subgenomic RNA synthesis, but not on translation of the encoded proteins. Virology, 387(1): 211-221 (2009).
Lamb et al., Nucleotide sequence of cloned cDNA coding for preproricin, Eur. J. Biochem.,1985, pp. 265-270, vol. 148.
Lee et al., Multiagent Vaccines Vectored by Venezuelan Equine Encephalitis Virus Replicon Elicits Immune Responses to Marburg Virus and Protection against Anthrax and Botulinum Neurotoxin in Mice, Vaccine, 2006, pp. 6886-6892, vol. 24.
Lehmann et al., Arterivirus nsp12 Versus the Coronavirus nsp16 2'-O-Methyltransferase: Comparison of the C-terminal Cleavage Products of Two Nidovirus pp1ab Polyproteins, J. Genl. Virol., 2015, pp. 2643-2655, vol. 96.
Lehmann et al., Arterivirus RNA-Dependent RNA Polymerase: Vital Enzymatic Activity remains Elusive, Virology, 2016, pp. 68-74, vol. 487.
Linsley et al., Binding of the B Cell activation antigen B7 to CD28 costimulates T cell proliferation and Interleukin 2 mRNA accumulation, J. Exp. Med., Mar. 1991, pp. 721-730, vol. 173.
Linsley et al., CTLA-4 Is a second receptor for the B Cell activation antigen B7, J. Exp. Med., Sep. 1991, pp. 561-570, vol. 174.
Lundstrom, Kenneth L: "Replicon RNA Viral Vectors as Vaccines"; Vaccines, 2016, vol. 4(4). pii: E39. PDF File: p. 1-23.
Luo, R., et al., Antiviral activity of type I and type III interferons against porcine reproductive and respiratory syndrome virus (PRRSV), Antiviral Research, vol. 91, pp. 99-101 (2011).
Maher and Dolinick, Specific hybridization arrest of dihydrofolate reductase mRNA in vitro using anti-sense RNA or anti-sense oligonucleotides, Arch. Biochem & Biophys., Feb. 15, 1987, pp. 214-220, vol. 253, Issue 1.
Maio, et al., Modulation by cytokines of HLA antigens, intercellular adhesion molecule 1 and high molecular weight melanoma associated antigen expression and of immune lysis of clones derived from the melanoma cell line MeM 50-10. Can. Immunol. Immunother., Jan. 1989, pp. 34-42, vol. 30, Issue 1.
Manolaridis, et al., Structure and Genetic Analysis of the Arterivirus Nonstructural Protein 7α, J. Virol., 2011, pp. 7449-7453, vol. 85, Issue 14.
Maruggi Giulietta et al, "Engineered alphavirus replicon vaccines based on known attenuated viral mutants show limited effects on immunogenicity", Virology, (Oct. 5, 2013), vol. 447, No. 1, doi:10.1016/J.VIROL.2013.07.021, ISSN 0042-6822, pp. 254-264, XP028754361.
McKnight et al., Deduced consensus sequence of Sindbis virus strain AR339: mutations contained in laboratory strains which affect cell culture and in vivo phenotypes. Virol. 70:1981 (1996), 9 pages.
McLoughlin, M. et al. Alphavirus infections in salmonids—a review, Journal of Fish Diseases, vol. 30, pp. 511-531 (2007).
Mekalanos et al., Cholera toxin genes: nucleotide sequence, deletion analysis and vaccine development, Nature, 1983, pp. 551-557, vol. 306.
Meshram, et al., "Multiple Host Factors Interact with the Hypervariable Domain of Chikungunya Virus nsP3 and Determine Viral Replication in Cell-Specific Mode", J. Virol., vol. 92, No. 16, p. 1-24, (Aug. 2018).
Michel et al. "Therapeutic vaccines and immune-based therapies for the treatment of chronic hepatitis B: perspectives and challenges." J. Hepatol., 54(6), 1286-1296, 2011.

(56) References Cited

OTHER PUBLICATIONS

Mir et. al. A Multicistronic DNA Vaccine Induces Significant Protection against Tuberculosis in Mice and Offers Flexibility in the Expressed Antigen Repertoire. 2009. Clinical and Vaccine Immunology. Vol. 16, No. 10. p. 1467-1475 (Year: 2009).
Mogler, M. et al., RNA-based viral vectors, Expert Rev. Vaccines, pp. 1-30 (2014).
Molenkamp et al., Characterization of an Arterivirus Defective Interfering RNA, 2001, pp. 519-525. In the Nidoviruses (Coronaviruses and Arteriviruses), Ehud Lavi et al. (ed.), Kluwer Academic/Plenum Publishers.
Molenkamp et al., Isolation and Characterization of an Arterivirus Defective Interfering RNA Genome, J. Virol., 2000, pp. 3156-3165, vol. 74, Issue 7.
Molenkamp R et al, "The arterivirus replicase is the only viral protein required for genome replication and subgenomic mRNA transcription.", The Journal of General Virology Oct. 2000, (Oct. 2000), vol. 81, No. Pt 10, ISSN 0022-1317, pp. 2491-2496, XP002771366.
Mullen, Transfer of the bacterial gene for cytosine deaminase to mammalian cells confers lethal sensitivity to 5-fluorocytosine: A negative selection system, Proc. Natl. Acad. Sci. USA, Jan. 1992, pp. 33-37, vol. 89.
Muraggi, G et al. Engineered Alphavirus Replicon Vaccines Based on Known Attenuated Viral Mutants Show Limited Effects on Immunogenicity, Virology, vol. 44, pp. 254-264 (2013).
Nagata, et al., Synthesis in *E. coli* of a polypeptide with human leukocyte interferon activity, Nature, 1980, pp. 316-320, vol. 284.
Nedialkova et al., Arterivirus Nsp1 Modulates the Accumulation of Minus-Strand Templates to Control the Relative Abundance of Viral mRNAs, PLoS Pathogens, 2010, e1000772, pp. 1-15, vol. 6, Issue 2.
Nedialkova, et al., Biochemical Characterization of Arterivirus Nonstructural Protein 11 Reveals the Nidovirus-Wide Conservation of a Replicative Endoribonuclease, J. Virol., 2009, pp. 5671-5682, vol. 83, Issue 11.
Needleman, S. et al., A general method applicable to the search for similarities in the amino acid sequence of two proteins J. Mol. Biol. 48:443-53 (1970).
Nolz, J et al. Strategies and Implications for Prime-Boost Vaccination to Generate Memory CD8 T Cells, Advances in Experimental Medicine and Biology, pp. 69-83, (2011).
Obeng-Adjei et al. "DNA vaccine cocktail expressing genotype A and C HBV surface and consensus core antigens generates robust cytotoxic and antibody responses and mice and Rhesus macaques" Cancer Gene Therapy, 20, 652-662, 2013.
Obeng-Adjei et al., "Synthetic DNA immunogen encoding hepatitis B core antigen drives immune response in liver," Cancer Gene Therapy, Nov. 5, 2012 Appleton & Lange, New York, vol. 19, Nr: 11, pp. 779-787.
Pasternak, Genetic Manipulation of Arterivirus Alternative mRNA Leader-Body Junction Sites Reveals Tight Regulation of Structural Protein Expression, J. Virol., Dec. 2000, pp. 11642-11653, vol. 74, Issue 24.
Pasternak, Regulation of Relative Abundance of Arterivirus Subgenomic mRNAs, J. Virol., Aug. 2004, pp. 8102-8113, vol. 78, Issue 15.
Pasternak, Sequence requirements for RNA strand transfer during nidovirus discontinuous subgenomic RNA synthesis, EMBO J., 2001, pp. 7220-7228, vol. 20, Issue 24.
Pasternak, The stability of the duplex between sense and antisense transcription-regulating sequences is a crucial factor in arterivirus subgenomic mRNA synthesis, J. Virol., 2003, pp. 1175-1183, vol. 77, Issue 2.
Pearson, W. et al., Improved tools for biological sequence comparison, Proc. Natl. Acad. Sci. US, vol. 85, pp. 2444-2448 (1988).
Pedersen et al., Open Reading Frame 1a-Encoded Subunits of the Arterivirus Replicase induce Endoplasmic Reticulum-Derived Double-Membrane Vesicles which carry the Viral Replication Complex, J. Virol., 1999, pp. 2016-2026, vol. 73, Issue 3.
Perri et al., Replicon Vectors Derived from Sindbis Virus and Semliki Forest Virus that Establish Persistent Replication in Host Cells, J. Virol., 2000, pp. 9802-9807, vol. 74, Issue 20.
Petrakova et al., Noncytopathic Replication of Venezuelan Equine Encephalitis Virus and Eastern Equine Encephalitis Virus Replicons in Mammalian Cells, Journal of Virology, Jun. 2005, p. 7597-7608.
Pijlman, G. et al., Kunjin virus replicons: an RNA-based, noncytopathic viral vector system for protein production, vaccine and gene therapy applications, Expert Opin. Biol. Ther, vol. 6, No. 2, pp. 135-145 (2006).
Posthuma et al., Formation of the Arterivirus Replication/Transcription Complex: a Key Role for Nonstructural Protein 3 in the Remodeling of Intracellular Membranes, J. Virol., 2008, pp. 4480-4491, vol. 82, Issue 9.
Posthuma et al., Site-Directed Mutagenesis of the Nidovirus Replicative Endoribonuclease NendoU Exerts Pleiotropic Effects on the Arterivirus Life Cycle, J. Virol., 2006, pp. 1653-1661, vol. 80, Issue 4.
Pushko et al., Individual and Bivalent Vaccines Based on Alphavirus Replicons Protect Guinea Pigs against Infection with Lassa and Ebola Viruses, J. Virol., 2001, pp. 11677-11685, vol. 75, Issue 23.
Pushko et al., Replicon-Helper Systems from Attenuated Venezuelan Equine Encephalitis Virus: Expression of Heterologous Genes In Vitro and Immunization against Heterologous Pathogens In Vivo, Virology, Dec. 22, 1997, pp. 389-401, vol. 239, Issue 2.
Radford et al., Cell-Type Specificity of Interferon-γ-Mediated HLA Class I Gene Transcription in Human Hematopoietic Tumor Cells. American Society of Hepatology, 1991, pp. 2008-2015.
Rice, C. et al., Production of Infectious RNA Transcripts from Sindbis Virus cDNA Clones: Mapping of Lethal Mutations, Rescue of a Temperature-Sensitive Marker, and In Vitro Mutagenesis to Generate Defined Mutants, Journal of Virology, vol. 61, No. 12, pp. 3809-3819 (1987).
Rogne et al., The isolation and characterisation of a cDNA clone for human lecith in cholesterol acyl transferase and its use to analyze the genes in patients with LCAT deficiency and fish eye disease, Biochem., Biophys. Res. Commun., 1987, pp. 161-169, vol. 148, Issue 1.
Sanchez and Holmgren, Recombinant system for overexpression of cholera toxin B subunit in Vibrio cholerae as a basis for vaccine development, Proc. Natl. Acad. Sci. USA, Jan. 1989, pp. 481-485, vol. 86, Issue 2.
Seif et al., Stable Antiviral Expression in BALB/c 3T3 Cells Carrying a Beta Interferon Sequence behind a Major Histocompatibility Complex Promoter Fragment, J. Virol., Oct. 1991, pp. 664-671, vol. 65, Issue 2.
Seybert et al., Biochemical Characterization of the Equine Arteritis Virus Helicase Suggests a Close Functional Relationship Between Arterivirus and Coronavirus Helicases, J. Virol., 2000, pp. 9586-9593, vol. 74, Issue 20.
Shylini, R Structure-Function Studies of the Venezuelanequine Encephalitis Virus 5'utr Promoter Element and Its Role in Attenuation of the Virus, Dissertation for Doctor of Philosophy, The University of Texas Medical Branch (2009) 147 pages.
Sjoberg,E et al., A Significantly Improved Semliki Forest Virus Expression System Based on Translation Enhancer Segments from the Viral Capsid Gene, Biotechnology, Vo,. 12, pp. 1127-1131, (1994).
Smith et al., Comparison of Biosequences, Adv. Appl. Math., 2:482-89 (1981).
Snijder EJ et al., "Identification of a Novel Structural Protein of Arteriviruses," J. Virol, Aug. 1999, pp. 6335-6345, vol. 37, Issue 8.
Snijder et al., 2005. The order Nidovirales, pp. 390-404, In Topley and Wilson's microbiology and microbial infections, B. W. Mahy and V. ter Meulen (ed.), Hodder Arnold, London, United Kingdom.
Snijder et al., Heterodimerization of the Two Major Envelope Proteins is Essential for Arterivirus Infectivity, J. Virol., 2003, pp. 97-104, vol. 77, Issue 1.
Snijder et al., Proteolytic Processing of the Arterivirus Replicase, 1995, pp. 443-451. In Corona-and Related Viruses, P.J. Talbot and G.A. Levy (ed.), Plenum Press, NY.
Snijder et al., The Arterivirus Nsp2 Protease, J. Biol. Chem., 1995, pp. 16671-16676, vol. 270, Issue 28.

(56) References Cited

OTHER PUBLICATIONS

Snijder, E.J., Arterivirus RNA Synthesis Dissected, 2001, pp. 241-253. In the Nidoviruses (Coronaviruses and Arteriviruses), Ehud Lavi et al. (ed.), Kluwer Academic/Plenum Publishers.

Snijder, E.J., The Arterivirus Replicase, The Road from RNA to Protein(s), and Back Again, 1998, pp. 97-108. In Coronaviruses and Arteriviruses, Enjuanes et al. (ed.), Plenum Press, NY.

Stanton et al., Nucleotide sequence comparison of normal and translocated murine c-myc genes, Nature, Aug. 1984, pp. 423-425, vol. 310.

Stirpe et al., Gelonin, a New Inhibitor of Protein Synthesis, Non-toxic to Intact Cells, J. Biol. Chem., Jul. 25, 1980, pp. 6947-6953, vol. 255.

Strauss etal., The AlpahViruses: Gene Expression, Replication and Evolution, Microbiological Reviews, pp. 491-562, Sep. 1994.

Te Velthuis, et al., Zn2+ Inhibits Coronavirus and Arterivirus RNA Polymerase Activity In Vitro and Zinc Ionophores Block the Replication of these Viruses in Cell Culture, PLoS Pathogens, 2010, e1001176, pp. 1-10, vol. 6, Issue 11.

Tepper et al., Murine interleukin-4 displays potent anti-tumor activity in vivo, Cell, May 5, 1989, pp. 503-512, vol. 57.

Thaa et al., Myristoylation of the Arterivirus E Protein: The Fatty Acid Modification is not Essential for Membrane Association but Contributes Significantly to Virus Infectivity, J. Genl. Virol., 2009, pp. 2704-2712, vol. 90.

Tian et al. Arterivirus minor envelope proteins are a major determinant of viral tropism in cell culture. J Virol. Apr. 2012;86(7):3701-12. (Year: 2012).

Tijerina et al., DMS Footprinting of Structured RNAs and RNA-Protein Complexes, Nat. Protoc., 2007, pp. 2608-2623, vol. 2, Issue 10.

Tijms et al., A zinc finger-containing papain-like protease couples subgenomic mRNA synthesis to genome translation in a positive-stranded RNA virus, Proc. Natl. Acad. Sci. USA, 2001, pp. 1889-1894, vol. 98, Issue 4.

Tijms et al., Arterivirus Subgenomic mRNA Synthesis and Virion Biogenesis Depend on the Multifunctional nsp1 Autoprotease, J. Virol., Oct. 2007, pp. 10496-10505, vol. 81, Issue 19.

Toribio et al., An RNA Trapping Mechanism in Alphavirus MRNA Promotes Translation and Initiation Nucleic Acids Res. 19, 44(9): pp. 4368-4380 (2016).

Toribio et al., Inhibition of host translation by virus infection in vivo, PNAS, vol. 107, No. 21, pp. 9837-9842 (2010).

Tweten et al., Diphtheria toxin. Effect of substituting aspartic acid for glutamic acid 148 on ADP-ribosyltransferase activity., J. Biol. Chem., Jun. 3, 1985, pp. 10392-10394, vol. 260.

Twu et al., Hepatitis B virus X gene can transactivate heterologous viral sequences, Proc Natl. Acad. Sci. USA, Mar. 1989, pp. 2046-2050, vol. 86.

Uematsu et al.: "Lack of Interference with Immunogenicity of a Chimeric Alphavirus Replicon Particle-Based Influenza Vaccine by Preexisting Antivector Immunity"; Clin Vaccine Immunol., Jul. 2012, vol. 19(7), p. 991-998.

Van Aken et al., Expression, Purification, and In Vitro Activity of an Arterivirus Main Proteinase, Virus Res., 2006, pp. 97-106, vol. 120.

Van Aken et al., Mutagenesis Analysis of the nsp4 Main Proteinase Reveals Determinants of Arterivirus Replicase Polyprotein Autoprocessing, J. Virol., 2006, pp. 3428-3437, vol. 80, Issue 7.

Van Den Born et al., Discontinuous Subgenomic RNA Synthesis in Arteriviruses is Guided by an RNA Hairpin Structure Located in the Genomic Leader Region, J. Virol., 2005, pp. 6312-6324, vol. 79, Issue 10.

Van Den Born, et al., "An infectious recombinant equine arteritis virus expressing green fluorescent protein from its replicase gene," J. Genl. Virol., Apr. 2007, pp. 1196-1205, vol. 88.

Van Den Born, Value of routine funduscopy in patients with hypertension: systematic review, BMJ, Jul. 9, 2005, pp. 1-5, vol. 331.

Van Der Meer et al., ORF1a-Encoded Replicase Subunits are Involved in the Membrane Association of the Arterivirus Replication Complex, J. Virol., 1998, pp. 6689-6698, vol. 72, Issue 8.

Van Dinten et al., Proteolytic Processing of the Open Reading Framer 1b-Encoded Part of Arterivirus Replicase is Mediated by nsp4 Serine Protease and is Essential for Virus Replication, J. Virol., 1999, pp. 2027-2037, vol. 73, Issue 3.

Van Dinten et al., The Predicted Metal-Binding Region of the Arterivirus Helicase Protein is Involved in Subgenomic mRNA Synthesis, Genome Replication, and Virion Biogenesis, J. Virol., 2000, pp. 5213-5223, vol. 74, Issue 11.

Van Dinten, An infectious arterivirus cDNA clone: Identification of a replicase point mutation that abolishes discontinuous mRNA transcription, Proc. Natl. Acad. Sci. USA, Feb. 1997, pp. 991-996, vol. 94, Issue 3.

Van Hemert et al., The In Vitro RNA Synthesizing Activity of the Isolated Arterivirus Replication/Transcription Complex is Dependent on a Host Factor, J. Biol. Chem., 2008, pp. 16525-16536, vol. 283, Issue 24.

Van Kasteren et al., Arterivirus and Nairovirus Ovarian Tumor Domain-Containing Deubiquitinases Target Activated RIG-I to Control Innate Immune Signaling, J. Virol., 2011, pp. 773-785, vol. 82, Issue 2.

Van Kasteren et al., Deubiquitinase Function of Arterivirus Papain-Like Protease 2 Suppresses the Innate Immune Response in Infected Host Cells, PNAS, 2013, pp. E838-E847.

Van Marle et al., Arterivirus discontinuous mRNA transcription is guided by base pairing between sense and antisense transcription-regulating sequences, Pro. Natl. Acad. Sci. USA, Aug. 6, 1999, pp. 12056-12061, vol. 96, Issue 21.

Van Marle, et al., Characterization of an Equine Arteritis Virus Replicase Mutant Defective in Subgenomic mRNA Synthesis, J. Virol., 1999, pp. 5274-5281, vol. 73, Issue 7.

Ventoso, I. et al. Translational resistance of late alphavirus mRNA to elF2 phosphorylation: a strategy to overcome the antiviral effect of protein kinase PKR, Genes and Development, vol. 20, pp. 87-100 (2006).

Ventoso, I., Adaptive Changes in Alphavirus mRNA Translation Allowed Colonization of Vertebrate Hosts, Journal of Virology, vol. 86, No. 17, pp. 9484-9494 (2012).

Vrudhula et al., Prodrugs of doxorubicin and melphalan and their activation by a monoclonal antibody-penicillin-G amidase conjugate, J. Med. Chem., 1993, pp. 919-923, vol. 36, Issue 7.

Ward, S. et al., Generation of CTL responses using Kunjin replicon RNA, Immunology and Cell Biology, vol. 81, pp. 73-78 (2003).

Warner et al. Induction of the HIV-Specific and Antibody Responses in Mice Using Retroviral Vector-Transduced Cells, AIDS Res. and Human Retroviruses, vol. 7, No. 8, pp. 645-655 (1991).

Wassenaar, et al., Alternative Proteolytic Processing of the Arterivirus Replicase ORF1a Polyprotein: Evidence that NSP2 Acts as a Cofactor for the NSP4 Serine Protease, J. Virol., 1997, pp. 9313-9322, vol. 71, Issue 12.

Watanabe, et al., Exogenous expression of mouse interferon gamma cDNA in mouse neuroblastoma C1300 cells results in reduced tumorigenicity by augmented anti-tumor immunity, Proc. Natl. Acad. Sci. USA, Dec. 1989, pp. 9456-9460, vol. 86.

Weber et al., Immunotherapy of a murine tumor with interleukin 2. J. Exp. Med., 1987, pp. 1716-1733, vol. 166.

White, L. et al., Role of Alpha/Beta Interferon in Venezuelan Equine Encephalitis Virus Pathogenesis: Effect of an Attenuating Mutation in the 59 Untranslated Region, Journal of Virology, vol. 75, No. 8, pp. 3706-3718 (2001).

Wilson et al., Prospects for gene therapy of familial hypercholesterolemia, Mol. Biol. Med., Jun. 1, 1990, pp. 223-232, vol. 7, Issue 3.

Wood et al., Preproabrin: genomic cloning, characterisation and the expression of the A-chain in *Escherichia coli*, Eur. J. Biochem., 1991, pp. 723-732, vol. 198.

World Health Organization, Hepatitis B: Fact sheet No. 204 [Internet] Mar. 2015. Available from https://www.who.int/news-room/fact-sheets/detail/hepatitis-b, 6 pages.

(56) References Cited

OTHER PUBLICATIONS

Xu et al.: "Type-specific and cross-reactive antibodies induced by human papillomavirus 31 L1/L2 virus-like particle";, J Med Microbiol. 2007, vol. 56(Pt 7), p. 907-13.

Yamamoto et al., The human LDL receptor: a cysteine-rich protein with multiple Alu sequences in its mRNA, Cell, Nov. 1984, pp. 27-38, vol. 39, Issue 1.

Yin et. al. Similarities and Differences in Antagonism of Neuron Alpha/Beta and Sindbis Alphaviruses 2009. Journal of Virology. 83 (19) p. 10036-10047 (Year: 2009).

Zhou, X. et al. Self-replicating Semliki Forest virus RNA as recombinant vaccine, Vaccine, vol. 12, No. 16, pp. 1510-1514 (1994).

* cited by examiner

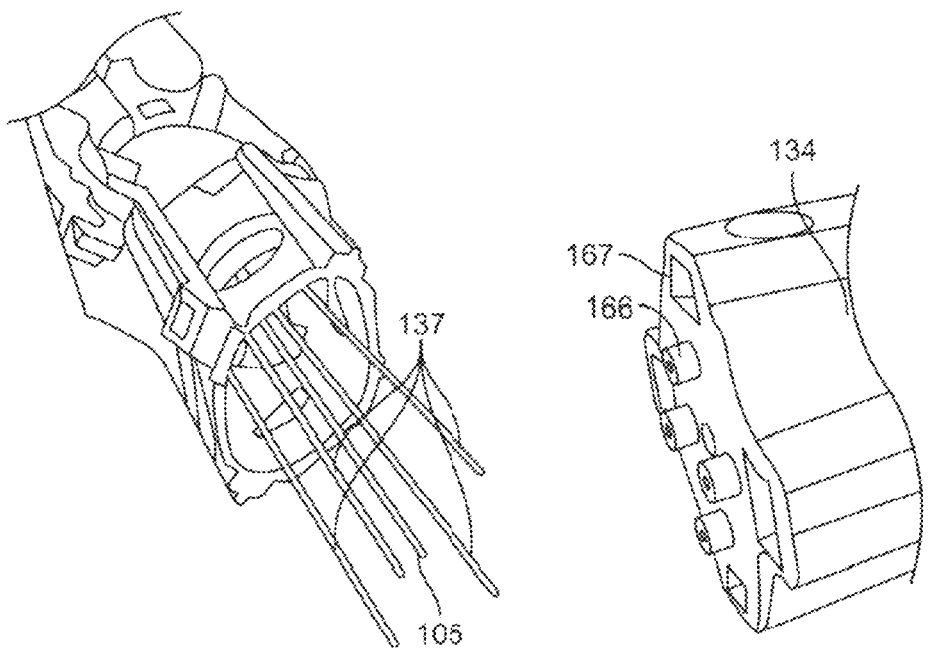
FIG. 9A
FIG. 9B
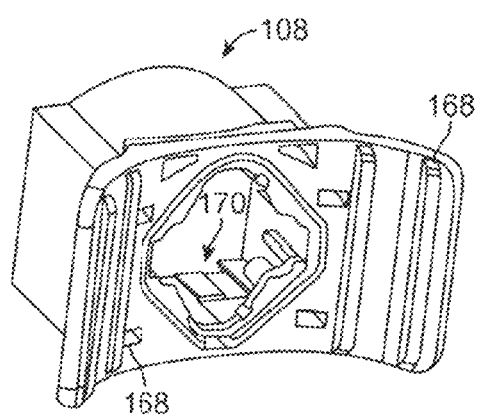
FIG. 9C

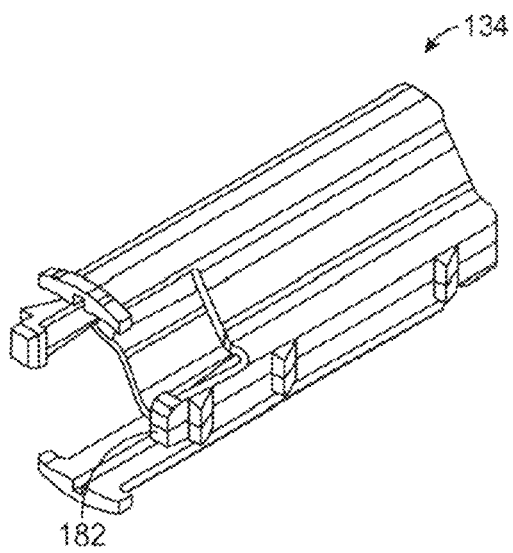 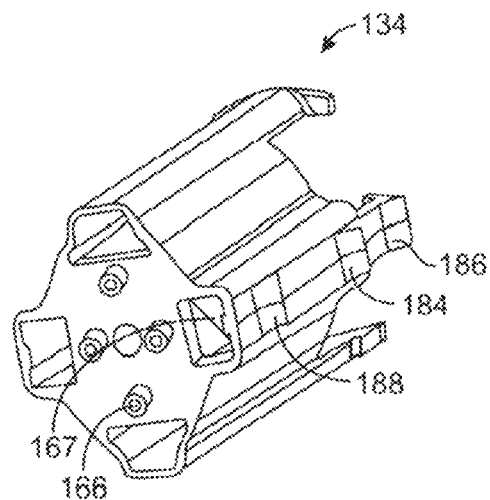
FIG. 11A          FIG. 11B
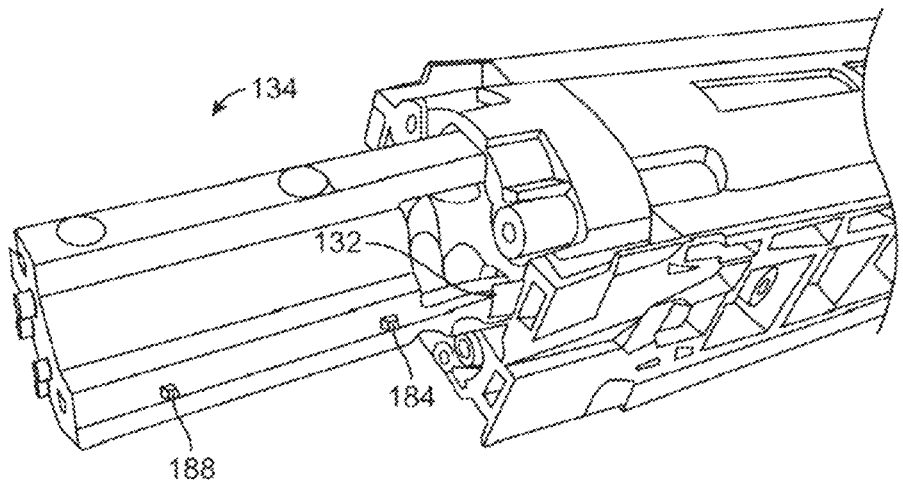
FIG. 11C

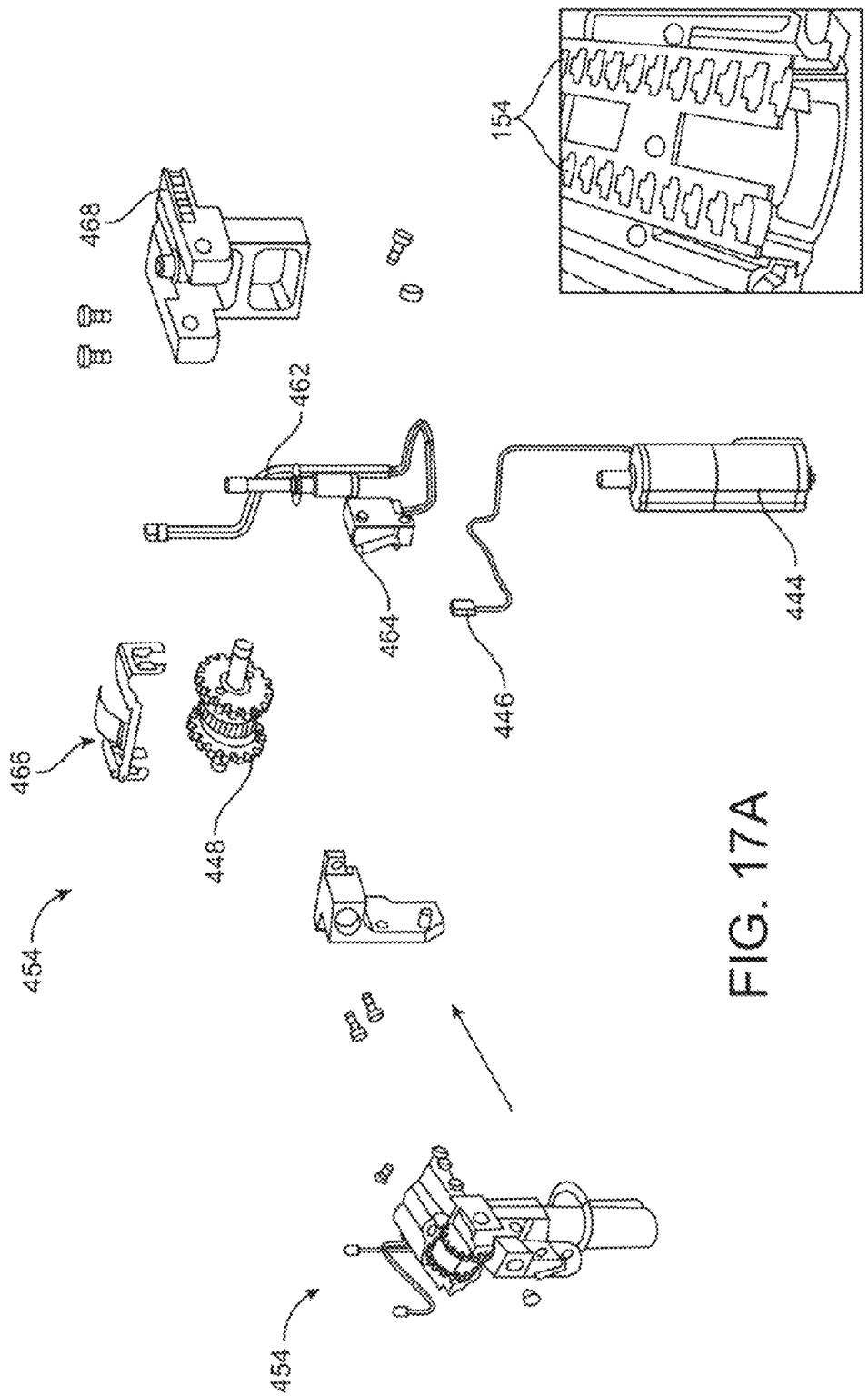

1. Core (lysate)
2. Core (sup)
3. Pol (lysate)
4. Pol (sup)
5. Core-FA2-Pol (sup)
6. Core-FA2-Pol (lysate)
7. Core-Pol (lysate)
8. Core-Pol (sup)

SEQUENCE LISTING

```
<160> NUMBER OF SEQ ID NOS: 24

<210> SEQ ID NO 1
<211> LENGTH: 444
<212> TYPE: DNA
<213> ORGANISM: Artificial Sequence
<220> FEATURE:
<223> OTHER INFORMATION: HBV truncated core antigen gene

<400> SEQUENCE: 1
gacatcgacc cttacaagga gttcggcgcc agcgtggaac tgctgtcttt tctgcccagt      60
gatttctttc cttccattcg agacctgctg gataccgcct ctgctctgta tcgggaagcc     120
ctggagagcc cagaacactg ctccccacac cataccgctc tgcgacaggc aatcctgtgc     180 tgggggagc tgatgaacct ggccacatgg gtgggatcga atctggagga ccccgcttca     240
cgggaactgg tggtcagcta cgtgaacgtc aatatgggcc tgaaaatccg ccagctgctg     300
tggttccata ttagctgcct gactttggga cgagagaccg tgctggaata cctggtgtcc     360
ttcggcgtct ggattcgcac tccccctgct tatcgaccac ccaacgcacc aattctgtcc     420
```
accctgcccg agaccacagt ggtc                                          444

<210> SEQ ID NO 2
<211> LENGTH: 148
<212> TYPE: PRT
<213> ORGANISM: Artificial Sequence
<220> FEATURE:
<223> OTHER INFORMATION: HBV truncated core antigen

<400> SEQUENCE: 2

Asp Ile Asp Pro Tyr Lys Glu Phe Gly Ala Ser Val Glu Leu Leu Ser
1               5                   10                  15

Phe Leu Pro Ser Asp Phe Phe Pro Ser Ile Arg Asp Leu Leu Asp Thr
            20                  25                  30

Ala Ser Ala Leu Tyr Arg Glu Ala Leu Glu Ser Pro Glu His Cys Ser
        35                  40                  45

Pro His His Thr Ala Leu Arg Gln Ala Ile Leu Cys Trp Gly Glu Leu
    50                  55                  60

Met Asn Leu Ala Thr Trp Val Gly Ser Asn Leu Glu Asp Pro Ala Ser
65                  70                  75                  80

Arg Glu Leu Val Val Ser Tyr Val Asn Val Asn Met Gly Leu Lys Ile
                85                  90                  95

Arg Gln Leu Leu Trp Phe His Ile Ser Cys Leu Thr Phe Gly Arg Glu
            100                 105                 110

Thr Val Leu Glu Tyr Leu Val Ser Phe Gly Val Trp Ile Arg Thr Pro
        115                 120                 125

Pro Ala Tyr Arg Pro Pro Asn Ala Pro Ile Leu Ser Thr Leu Pro Glu
    130                 135                 140

Thr Thr Val Val
145

<210> SEQ ID NO 3
<211> LENGTH: 2529
<212> TYPE: DNA
<213> ORGANISM: Artificial Sequence
<220> FEATURE:
<223> OTHER INFORMATION: HBV pol antigen gene

<400> SEQUENCE: 3
atgcccctgt cttaccagca ctttagaaag cttctgctgc tggacgatga agccgggcct        60
ctggaggaag agctgccaag gctggcagac gaggggctga accggagagt ggccgaagat       120
ctgaatctgg gaaacctgaa cgtgagcatc ccttggactc ataaagtcgg caacttcacc       180
gggctgtaca gctccacagt gcctgtcttc aatccagagt ggcagacacc atcctttccc       240
aacattcacc tgcaggagga catcattaat agatgcgaac agttcgtggg acctctgaca       300
gtcaacgaaa gaggcgcctg aaactgatc atgcctgcca ggttttaccc aaatgtgact        360
aagtatctgc cactggataa gggcatcaag ccttactatc agagcacct ggtgaaccat        420 tacttccaga ctagacacta tctgcatacc ctgtggaagg ccggaatcct gtacaaacga       480
gaaactaccc ggagtgcttc attttgtggc tccccatatt cttgggaaca ggagctgcag       540
catggcaggc tggtgttcca gaccagcaca cgccacgggg atgagtcctt ttgccagcag       600
tctagtggca tcctgagcag atccccgtg gggccttgtc tgcagtctca gctgcggaag        660
agtagactgg gactgcagcc acagcaggga cacctggcac gacggcagca gggaaggtct       720
ggcagtatcc gggctagagt gcatcccaca actagaaggc ctttcggcgt cgagccatca       780

| | |
|---|---|
| ggaagcggcc acaccacaaa caccgcatca agctcctcta gttgcctgca tcagtcagcc | 840 |
| gtgagaaagg ccgcttacag ccacctgtcc acatctaaaa ggcactcaag ctccgggcat | 900 |
| gctgtggagc tgcacaacat ccctccaaat tctgcacgca gtcagtcaga aggacccgtg | 960 |
| ttcagctgct ggtggctgca gtttcggaac tcaaagcctt gcagcgacta ttgtctgagc | 1020 |
| catattgtga atctgctgga ggattggggc ccttgtaccg agcacgggga acaccatatc | 1080 |
| aggattccac gaacaccagc acgagtgact ggaggggtgt cctggtggac aagaacccc | 1140 |
| cacaatacta ccgagagccg gctggtggtc gatttcagtc agttttcaag aggcaacaca | 1200 |
| agggtgtcat ggcccaaatt cgccgtccct aatctgcaga gtctgactaa cctgctgtct | 1260 |
| agtaatctga gctggctgtc cctggacgtg tccgcagcct tttaccacct gcctctgcat | 1320 |
| ccagctgcaa tgccccatct gctggtgggg tcaagcggac tgagtcgcta cgtcgcccga | 1380 |
| ctgtcctcta actcacgcat cattaatcac cagcatggca ccatgcagaa cctgcacgat | 1440 |
| agctgttccc ggaatctgta cgtgtctctg ctgctgctgt ataagacatt cggcagaaaa | 1500 |
| ctgcacctgt acagccatcc tatcattctg ggtttagga gatcccaat gggagtggga | 1560 |
| ctgagcccct cctgctggc acagtttacc tccgccattt gctctgtggt ccgccgagcc | 1620 |
| ttcccacact gtctggcttt ttcctatatg aacaatgtgg tcctgggcgc caaatccgtg | 1680 |
| cagcatctgg agtctctgtt cacagctgtc actaactttc tgctgagcct ggggatccac | 1740 |
| ctgaacccaa ataagactaa cgctgggggg tacagcctga atttcatggg atatgtgatt | 1800 |
| ggatcctggg ggaccctgcc acaggagcac atcgtgcaga agatcaagga atgctttcgg | 1860 |
| aagctgcccg tcaacagacc tatcgactgg aaagtgtgcc agcggattgt cggactgctg | 1920 |
| ggcttcgccg ctcccttac ccagtgcggg tacccagcac tgatgcccct gtatgcctgt | 1980 |
| atccagtcta gcaggctttt cacctttagt cctacataca aggcattcct gtgcaaacag | 2040 |
| tacctgaacc tgtatccagt ggcaaggcag cgacctggac tgtgccaggt ctttgcaaat | 2100 |
| gccactccta ccggctgggg gctggctatc ggacatcagc gaatgcgggg cacattcgtg | 2160 |
| gccccctgc ctattcacac tgctcagctg ctggcagcct gctttgctag atctaggagt | 2220 |
| ggagcaaagc tgatcggcac cgacaatagt gtggtcctgt caagaaaata cacatccttc | 2280 |
| ccatggctgc tgggatgtgc tgcaaactgg attctgaggg gcaccagctt cgtgtacgtc | 2340 |
| ccctcagccc tgaatcctgc tgacgatcca tcccgcgggc gactgggact gtaccgacct | 2400 |
| ctgctgagac tgcccttcag gcctacaact ggccggacat ctctgtatgc cgattcacca | 2460 |
| agcgtgccct cacacctgcc tgacagagtc cactttgctt caccccctgca cgtcgcttgg | 2520 |
| cggcctcca | 2529 |

<210> SEQ ID NO 4
<211> LENGTH: 843
<212> TYPE: PRT
<213> ORGANISM: Artificial Sequence
<220> FEATURE:
<223> OTHER INFORMATION: HBV pol antigen

<400> SEQUENCE: 4

```
Met Pro Leu Ser Tyr Gln His Phe Arg Lys Leu Leu Leu Asp Asp
1               5                   10                  15

Glu Ala Gly Pro Leu Glu Glu Glu Leu Pro Arg Leu Ala Asp Glu Gly
                20                  25                  30

Leu Asn Arg Arg Val Ala Glu Asp Leu Asn Leu Gly Asn Leu Asn Val
            35                  40                  45
```

```
Ser Ile Pro Trp Thr His Lys Val Gly Asn Phe Thr Gly Leu Tyr Ser
 50                  55                  60

Ser Thr Val Pro Val Phe Asn Pro Glu Trp Gln Thr Pro Ser Phe Pro
 65                  70                  75                  80

Asn Ile His Leu Gln Glu Asp Ile Ile Asn Arg Cys Glu Gln Phe Val
                 85                  90                  95

Gly Pro Leu Thr Val Asn Glu Lys Arg Leu Lys Leu Ile Met Pro
                100                 105                 110

Ala Arg Phe Tyr Pro Asn Val Thr Lys Tyr Leu Pro Leu Asp Lys Gly
            115                 120                 125

Ile Lys Pro Tyr Tyr Pro Glu His Leu Val Asn His Tyr Phe Gln Thr
        130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
                165                 170                 175

Gln Glu Leu Gln His Gly Arg Leu Val Phe Gln Thr Ser Thr Arg His
            180                 185                 190

Gly Asp Glu Ser Phe Cys Gln Gln Ser Ser Gly Ile Leu Ser Arg Ser
        195                 200                 205

Pro Val Gly Pro Cys Leu Gln Ser Gln Leu Arg Lys Ser Arg Leu Gly
    210                 215                 220

Leu Gln Pro Gln Gln Gly His Leu Ala Arg Arg Gln Gln Gly Arg Ser
225                 230                 235                 240

Gly Ser Ile Arg Ala Arg Val His Pro Thr Thr Arg Arg Pro Phe Gly
                245                 250                 255

Val Glu Pro Ser Gly Ser Gly His Thr Thr Asn Thr Ala Ser Ser Ser
            260                 265                 270

Ser Ser Cys Leu His Gln Ser Ala Val Arg Lys Ala Ala Tyr Ser His
        275                 280                 285

Leu Ser Thr Ser Lys Arg His Ser Ser Ser Gly His Ala Val Glu Leu
    290                 295                 300

His Asn Ile Pro Pro Asn Ser Ala Arg Ser Gln Ser Glu Gly Pro Val
305                 310                 315                 320

Phe Ser Cys Trp Trp Leu Gln Phe Arg Asn Ser Lys Pro Cys Ser Asp
                325                 330                 335

Tyr Cys Leu Ser His Ile Val Asn Leu Leu Glu Asp Trp Gly Pro Cys
            340                 345                 350

Thr Glu His Gly Glu His His Ile Arg Ile Pro Arg Thr Pro Ala Arg
        355                 360                 365

Val Thr Gly Gly Val Phe Leu Val Asp Lys Asn Pro His Asn Thr Thr
    370                 375                 380

Glu Ser Arg Leu Val Val Asp Phe Ser Gln Phe Ser Arg Gly Asn Thr
385                 390                 395                 400

Arg Val Ser Trp Pro Lys Phe Ala Val Pro Asn Leu Gln Ser Leu Thr
                405                 410                 415

Asn Leu Leu Ser Ser Asn Leu Ser Trp Leu Ser Leu Asp Val Ser Ala
            420                 425                 430

Ala Phe Tyr His Leu Pro Leu His Pro Ala Ala Met Pro His Leu Leu
        435                 440                 445

Val Gly Ser Ser Gly Leu Ser Arg Tyr Val Ala Arg Leu Ser Ser Asn
    450                 455                 460

Ser Arg Ile Ile Asn His Gln His Gly Thr Met Gln Asn Leu His Asp
```

```
                465                 470                 475                 480
        Ser Cys Ser Arg Asn Leu Tyr Val Ser Leu Leu Leu Tyr Lys Thr
                            485                 490                 495
        Phe Gly Arg Lys Leu His Leu Tyr Ser His Pro Ile Ile Leu Gly Phe
                        500                 505                 510
        Arg Lys Ile Pro Met Gly Val Gly Leu Ser Pro Phe Leu Leu Ala Gln
                        515                 520                 525
        Phe Thr Ser Ala Ile Cys Ser Val Val Arg Arg Ala Phe Pro His Cys
                    530                 535                 540
        Leu Ala Phe Ser Tyr Met Asn Val Val Leu Gly Ala Lys Ser Val
        545                 550                 555                 560
        Gln His Leu Glu Ser Leu Phe Thr Ala Val Thr Asn Phe Leu Leu Ser
                            565                 570                 575
        Leu Gly Ile His Leu Asn Pro Asn Lys Thr Lys Arg Trp Gly Tyr Ser
                        580                 585                 590
        Leu Asn Phe Met Gly Tyr Val Ile Gly Ser Trp Gly Thr Leu Pro Gln
                        595                 600                 605
        Glu His Ile Val Gln Lys Ile Lys Glu Cys Phe Arg Lys Leu Pro Val
                    610                 615                 620
        Asn Arg Pro Ile Asp Trp Lys Val Cys Gln Arg Ile Val Gly Leu Leu
        625                 630                 635                 640
        Gly Phe Ala Ala Pro Phe Thr Gln Cys Gly Tyr Pro Ala Leu Met Pro
                            645                 650                 655
        Leu Tyr Ala Cys Ile Gln Ser Lys Gln Ala Phe Thr Phe Ser Pro Thr
                        660                 665                 670
        Tyr Lys Ala Phe Leu Cys Lys Gln Tyr Leu Asn Leu Tyr Pro Val Ala
                    675                 680                 685
        Arg Gln Arg Pro Gly Leu Cys Gln Val Phe Ala Asn Ala Thr Pro Thr
                    690                 695                 700
        Gly Trp Gly Leu Ala Ile Gly His Gln Arg Met Arg Gly Thr Phe Val
        705                 710                 715                 720
        Ala Pro Leu Pro Ile His Thr Ala Gln Leu Leu Ala Ala Cys Phe Ala
                            725                 730                 735
        Arg Ser Arg Ser Gly Ala Lys Leu Ile Gly Thr Asp Asn Ser Val Val
                        740                 745                 750
        Leu Ser Arg Lys Tyr Thr Ser Phe Pro Trp Leu Leu Gly Cys Ala Ala
                    755                 760                 765
        Asn Trp Ile Leu Arg Gly Thr Ser Phe Val Tyr Val Pro Ser Ala Leu
                    770                 775                 780
        Asn Pro Ala Asp Asp Pro Ser Arg Gly Arg Leu Gly Leu Tyr Arg Pro
        785                 790                 795                 800
        Leu Leu Arg Leu Pro Phe Arg Pro Thr Thr Gly Arg Thr Ser Leu Tyr
                            805                 810                 815
        Ala Asp Ser Pro Ser Val Pro Ser His Leu Pro Asp Arg Val His Phe
                        820                 825                 830
        Ala Ser Pro Leu His Val Ala Trp Arg Pro Pro
                    835                 840

<210> SEQ ID NO 5
<211> LENGTH: 63
<212> TYPE: DNA
<213> ORGANISM: Artificial Sequence
<220> FEATURE:
<223> OTHER INFORMATION: Cystatin S signal peptide coding sequence
```

<400> SEQUENCE: 5

```
atggctcgac tctctgtgtac cctgctactc ctgatggcta ccctggctgg agctctggcc    60
agc                                                                   63
```

<210> SEQ ID NO 6
<211> LENGTH: 21
<212> TYPE: PRT
<213> ORGANISM: Artificial Sequence
<220> FEATURE:
<223> OTHER INFORMATION: Cystatin S signal peptide sequence

<400> SEQUENCE: 6

```
Met Ala Arg Pro Leu Cys Thr Leu Leu Leu Leu Met Ala Thr Leu Ala
1               5                   10                  15

Gly Ala Leu Ala Ser
            20
```

<210> SEQ ID NO 7
<211> LENGTH: 586
<212> TYPE: DNA
<213> ORGANISM: Artificial Sequence
<220> FEATURE:
<223> OTHER INFORMATION: hCMV promoter sequence

<400> SEQUENCE: 7

```
tgacattgat tattgactag ttattaatag taatcaatta cggggtcatt agttcatagc    60
ccatatatgg agttccgcgt tacataactt acggtaaatg gcccgcctgg ctgaccgccc   120
aacgaccccc gcccattgac gtcaataatg acgtatgttc ccatagtaac gccaataggg   180
actttccatt gacgtcaatg ggtggactat ttacggtaaa ctgcccactt ggcagtacat   240
caagtgtatc atatgccaag tacgccccct attgacgtca atgacggtaa atggcccgcc   300
tggcattatg cccagtacat gaccttatgg gactttccta cttggcagta catctacgta   360
ttagtcatcg ctattaccat ggtgatgcgg ttttggcagt acatcaatgg gcgtggatag   420
cggtttgact cacggggatt tccaagtctc cacccccattg acgtcaatgg gagtttgttt   480
tggcaccaaa atcaacggga ctttccaaaa tgtcgtaaca actccgcccc attgacgcaa   540
atgggcggta ggcgtgtacg gtgggaggtc tatataagca gagctc                 586
```

<210> SEQ ID NO 8
<211> LENGTH: 378
<212> TYPE: DNA
<213> ORGANISM: Artificial Sequence
<220> FEATURE:
<223> OTHER INFORMATION: triple enhancer regulatory sequence

<400> SEQUENCE: 8

```
ggctcgcatc tctccttcac gcgcccgccg ccctacctga ggccgccatc cacgccggtt    60
gagtcgcgtt ctgccgcctc ccgcctgtgg tgcctcctga actgcgtccg ccgtctaggt   120
aagtttaaag ctcaggtcga gaccgggcct ttgtccggcg ctcccttgga gcctacctag   180
actcagccgg ctctccacgc tttgcctgac cctgcttgct caactctagt tctctcgtta   240
acttaatgag acagatagaa actggtcttg tagaaacaga gtagtcgcct gcttttctgc   300
caggtgctga cttctctccc ctgggctttt ttcttttttct caggttgaaa agaagaagac   360
gaagaagacg aagaagac                                                378
```

<210> SEQ ID NO 9
<211> LENGTH: 99

```
<212> TYPE: DNA
<213> ORGANISM: Artificial Sequence
<220> FEATURE:
<223> OTHER INFORMATION: Bla promoter sequence

<400> SEQUENCE: 9 accccctattt gtttattttt ctaaatacat tcaaatatgt atccgctcat gagacaataa    60
ccctgataaa tgcttcaata atattgaaaa aggaagagt                           99

<210> SEQ ID NO 10
<211> LENGTH: 671
<212> TYPE: DNA
<213> ORGANISM: Artificial Sequence
<220> FEATURE:
<223> OTHER INFORMATION: pUC ori sequence

<400> SEQUENCE: 10
cccgtagaaa agatcaaagg atcttcttga gatccttttt ttctgcgcgt aatctgctgc    60
ttgcaaacaa aaaaaccgct accagcggtg gtttgtttgc cggatcaaga gctaccaact   120
ctttttccga aggtaactgg cttcagcaga gcgcagatac caaatactgt tcttctagtg   180
tagccgtagt taggccacca cttcaagaac tctgtagcac cgcctacata cctcgctctg   240
ctaatcctgt taccagtggc tgctgccagt ggcgataagt cgtgtcttac cgggttggac   300
tcaagacgat agttaccgga taaggcgcag cggtcgggct gaacggggggg ttcgtgcaca   360 cagcccagct tggagcgaac gacctacacc gaactgagat acctacagcg tgagctatga   420
gaaagcgcca cgcttcccga agggagaaag gcggacaggt atccggtaag cggcagggtc   480
ggaacaggag agcgcacgag ggagcttcca gggggaaacg cctggtatct ttatagtcct   540
gtcgggtttc gccacctctg acttgagcgt cgatttttgt gatgctcgtc aggggggcgg   600
agcctatgga aaaacgccag caacgcggcc ttttacggt tcctggcctt tgctggcct   660 tttgctcaca t                                                         671

<210> SEQ ID NO 11
<211> LENGTH: 225
<212> TYPE: DNA
<213> ORGANISM: Artificial Sequence
<220> FEATURE:
<223> OTHER INFORMATION: bGH polyadenylation signal sequence

<400> SEQUENCE: 11
ctgtgccttc tagttgccag ccatctgttg tttgcccctc ccccgtgcct tccttgaccc    60
tggaaggtgc cactcccact gtcctttcct aataaaatga ggaaattgca tcgcattgtc   120
tgagtaggtg tcattctatt ctggggggtg ggtggggca ggacagcaag ggggaggatt    180
gggaagacaa tagcaggcat gctggggatg cggtgggctc tatgg                   225

<210> SEQ ID NO 12
<211> LENGTH: 795
<212> TYPE: DNA
<213> ORGANISM: Artificial Sequence
<220> FEATURE:
<223> OTHER INFORMATION: Kan R gene

<400> SEQUENCE: 12
atgattgagc aagatggtct tcacgctggc tcgccagctg cgtgggtgga acgcctgttt    60
ggttatgatt gggcgcagca gactattgga tgttccgacg cggctgtatt tcggctgtct   120
gctcagggtc gccccgtgct gtttgtgaag acggatttgt ctggcgcatt aaatgagtta   180
```

-continued

```
caggacgagg cggctcgtct gagttggttg gccaccaccg gcgtgccctg cgccgcagtg    240
ctggatgtcg tgacagaagc aggccgcgat tggctccttc tcggcgaagt gccgggccag    300
gacctgctca gcagccactt ggcaccggca gaaaaagttt ctatcatggc cgacgccatg    360
cgtcgtcttc acactctcga tccggccacg tgcccctttg accaccaggc caagcatcgt    420
attgaacgtg cgcgtactcg gatggaagca ggtttagtag accaggacga tttggatgag    480
gaacatcaag gcctggcccc ggctgaactg tttgcgcgct aaaaagcgtc gatgccagat    540
ggcgaagatt tggtagtcac ccatggagat gcgtgtttgc aaacatcat ggttgaaaat     600 ggccgcttct caggctttat tgactgtggg cgcctgggtg ttgccgaccg ctatcaagat    660
attgcgctcg caactcgtga catcgctgaa gagctgggcg agaatgggc tgaccgtttc      720 ctggtactgt atggcattgc agcgcccgat tcccaacgca tcgcatttta tcgtctgctg    780
gatgagtttt tctaa                                                     795
```

<210> SEQ ID NO 13
<211> LENGTH: 264
<212> TYPE: PRT
<213> ORGANISM: Artificial Sequence
<220> FEATURE:
<223> OTHER INFORMATION: Kan R protein

<400> SEQUENCE: 13

```
Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Leu Asp Glu
145                 150                 155                 160

Glu His Gln Gly Leu Ala Pro Ala Glu Leu Phe Ala Arg Leu Lys Ala
                165                 170                 175

Ser Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255
```

Tyr Arg Leu Leu Asp Glu Phe Phe
            260

<210> SEQ ID NO 14
<211> LENGTH: 149
<212> TYPE: PRT
<213> ORGANISM: Artificial Sequence
<220> FEATURE:
<223> OTHER INFORMATION: HBV truncated core antigen

<400> SEQUENCE: 14

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val
145

<210> SEQ ID NO 15
<211> LENGTH: 447
<212> TYPE: DNA
<213> ORGANISM: Artificial Sequence
<220> FEATURE:
<223> OTHER INFORMATION: HBV truncated core antigen gene

<400> SEQUENCE: 15
atggacatcg acccttacaa ggagttcggc gccagcgtgg aactgctgtc tttctgccc      60 agtgatttct tccttccat tcgagacctg ctggataccg cctctgctct gtatcgggaa     120
gccctggaga gcccagaaca ctgctcccca caccataccg ctctgcgaca ggcaatcctg     180
tgctgggggg agctgatgaa cctggccaca tgggtgggat ccaatctgga ggaccccgct     240
tcacgggaac tggtggtcag ctacgtgaac gtcaatatgg gcctgaaaat ccgccagctg     300
ctgtggttcc atattagctg cctgactttt ggacgagaga ccgtgctgga atacctggtg     360
tccttcggcg tctggatccg cactccccct gcttatcgac acccaacgc accaattctg      420 tccaccctgc ccgagaccac agtggtc                                         447

<210> SEQ ID NO 16
<211> LENGTH: 2529
<212> TYPE: DNA
<213> ORGANISM: Artificial Sequence
<220> FEATURE:
<223> OTHER INFORMATION: HBV pol antigen gene

<400> SEQUENCE: 16

```
atgcccctgt cttaccagca ctttagaaag ctgctgctgc tggacgatga agccgggcct    60
ctggaggaag agctgccaag gctggcagac gaggggctga accggagagt ggccgaagat   120
ctgaatctgg gaaacctgaa cgtgagcatc ccttggactc ataaagtcgg caacttcacc   180
gggctgtaca gctccacagt gcctgtcttc aatccagagt ggcagacacc atcctttccc   240
aacattcacc tgcaggagga catcattaat agatgcgaac agttcgtggg acctctgaca   300
gtcaacgaaa agaggcgcct gaaactgatc atgcctgcca ggttttaccc aaatgtgact   360
aagtatctgc cactggataa gggcatcaag ccttactatc agagcacct ggtgaaccat    420
tacttccaga ctagacacta tctgcatacc cgtggaagg ccggaatcct gtacaaacga    480
gaaactaccc ggagtgcttc attttgtggc tccccatatt cttgggaaca ggagctgcag   540
catggcaggc tggtgttcca gaccagcaca cgccacgggg atgagtcctt ttgccagcag   600
tctagtggca tcctgagcag atcccccgtg gggccttgtc tgcagtctca gctgcggaag   660
agtagactgg gactgcagcc acagcaggga cacctggcac gacggcagca gggaaggtct   720
ggcagtatcc gggctagagt gcatcccaca actagaaggc ctttcggcgt cgagccatca   780
ggaagcggcc acaccacaaa caccgcatca agctcctcta gttgcctgca tcagtcagcc   840
gtgagaaagg ccgcttacag ccacctgtcc acatctaaaa ggcactcaag ctccgggcat   900
gctgtggagc tgcacaacat ccctccaaat tctgcacgca gtcagtcaga aggacccgtg   960
ttcagctgct ggtggctgca gtttcggaac tcaaagcctt gcagcgacta ttgtctgagc  1020
catattgtga atctgctgga ggattggggc ccttgtaccg agcacgggga acaccatatc  1080
aggattccac gaacaccagc acgagtgact ggaggggtgt tcctggtgga caagaaccc   1140
cacaatacta ccgagagccg gctggtggtc gatttcagtc agttttcaag aggcaacaca  1200
agggtgtcat ggcccaaatt cgccgtccct aatctgcaga gtctgactaa cctgctgtct  1260
agtaatctga gctggctgtc cctggacgtg tccgcagcct tttaccacct gcctctgcat  1320
ccagctgcaa tgccccatct gctggtgggg tcaagcggac tgagtcgcta cgtcgcccga  1380
ctgtcctcta actcacgcat cattaatcac cagcatggca ccatgcagaa cctgcacgat  1440
agctgttccc ggaatctgta cgtgtctctg ctgctgctgt ataagacatt cggcagaaaa  1500
ctgcacctgt acagccatcc tatcattctg gggtttagga agatcccaat gggagtggga  1560
ctgagcccct tcctgctggc acagtttacc tccgccattt gctctgtggt ccgccgagcc  1620
ttcccacact gtctggcttt ttcctatatg aacaatgtgg tcctgggcgc caaatccgtg  1680
cagcatctgg agtctctgtt cacagctgtc actaactttc tgctgagcct ggggatccac  1740
ctgaacccaa ataagactaa cgctgggggg tacagcctga atttcatggg atatgtgatt  1800
ggatcctggg gaccctgcc acaggagcac atcgtgcaga agatcaagga atgctttcgg  1860
aagctgcccg tcaacagacc tatcgactgg aaagtgtgcc agcggattgt cggactgctg  1920
ggcttcgccg ctcccttta ccagtgcggg tacccagcac tgatgcccct gtatgcctgt  1980
atccagtcta agcaggcttt caccttagt cctacataca aggcattcct gtgcaaacag  2040
tacctgaacc tgtatccagt ggcaaggcag cgacctggac tgtgccaggt cttttgcaaat  2100
gccactccta ccggctgggg gctggctatc ggacatcagc gaatgcgggg cacattcgtg  2160
gcccccctgc ctattcacac tgctcagctg ctggcagcct gctttgctag atctaggagt  2220
ggagcaaagc tgatcggcac cgacaatagt gtggtcctgt caagaaaata cacatccttc  2280
ccatggctgc tgggatgtgc tgcaaactgg attctgaggg gcaccagctt cgtgtacgtc  2340
```

```
ccctcagccc tgaatcctgc tgacgatcca tcccgcgggc gactgggact gtaccgacct    2400
ctgctgagac tgcccttcag gcctacaact ggccggacat ctctgtatgc cgattcacca    2460
agcgtgccct cacacctgcc tgacagagtc cactttgctt caccccctgca cgtcgcttgg    2520 cggcctcca                                                             2529

<210> SEQ ID NO 17
<211> LENGTH: 684
<212> TYPE: DNA
<213> ORGANISM: Artificial Sequence
<220> FEATURE:
<223> OTHER INFORMATION: hCMV promoter sequence

<400> SEQUENCE: 17
accgccatgt tgacattgat tattgactag ttattaatag taatcaatta cggggtcatt      60
agttcatagc ccatatatgg agttccgcgt tacataactt acggtaaatg gcccgcctgg     120
ctgaccgccc aacgacccccc gcccattgac gtcaataatg acgtatgttc ccatagtaac    180
gccaataggg actttccatt gacgtcaatg ggtggagtat ttacggtaaa ctgcccactt     240
ggcagtacat caagtgtatc atatgccaag tacgccccct attgacgtca atgacggtaa     300
atggcccgcc tggcattatg cccagtacat gaccttatgg gactttccta cttggcagta    360
catctacgta ttagtcatcg ctattaccat ggtgatgcgg ttttggcagt acatcaatgg     420
gcgtggatag cggtttgact cacggggatt tccaagtctc cacccccattg acgtcaatgg    480 gagtttgttt tggcaccaaa atcaacggga ctttccaaaa tgtcgtaaca actccgcccc    540
attgacgcaa atgggcggta ggcgtgtacg gtgggaggtc tatataagca gagctcgttt     600
agtgaaccgt cagatcgcct ggagacgcca tccacgctgt tttgacctcc atagaagaca     660
ccgggaccga tccagcctcc gcgg                                           684

<210> SEQ ID NO 18
<211> LENGTH: 81
<212> TYPE: DNA
<213> ORGANISM: Artificial Sequence
<220> FEATURE:
<223> OTHER INFORMATION: immunoglobulin secretion signal coding sequence

<400> SEQUENCE: 18
atggagttcg gcctgtcttg ggtctttctg gtggcaatcc tgaagggcgt gcagtgtgaa      60
gtgcagctgc tggagtctgg a                                               81

<210> SEQ ID NO 19
<211> LENGTH: 27
<212> TYPE: PRT
<213> ORGANISM: Artificial Sequence
<220> FEATURE:
<223> OTHER INFORMATION: immunoglobulin secretion signal sequence

<400> SEQUENCE: 19

Met Glu Phe Gly Leu Ser Trp Val Phe Leu Val Ala Ile Leu Lys Gly
1               5                   10                  15

Val Gln Cys Glu Val Gln Leu Leu Glu Ser Gly
            20                  25

<210> SEQ ID NO 20
<211> LENGTH: 996
<212> TYPE: PRT
<213> ORGANISM: Artificial Sequence
<220> FEATURE:
<223> OTHER INFORMATION: HBV core-pol fusion antigen sequence
```

<400> SEQUENCE: 20

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Ala Gly Ala Gly Met Pro Leu Ser Tyr Gln His
145                 150                 155                 160

Phe Arg Lys Leu Leu Leu Leu Asp Asp Glu Ala Gly Pro Leu Glu Glu
                165                 170                 175

Glu Leu Pro Arg Leu Ala Asp Glu Gly Leu Asn Arg Arg Val Ala Glu
            180                 185                 190

Asp Leu Asn Leu Gly Asn Leu Asn Val Ser Ile Pro Trp Thr His Lys
        195                 200                 205

Val Gly Asn Phe Thr Gly Leu Tyr Ser Ser Thr Val Pro Val Phe Asn
    210                 215                 220

Pro Glu Trp Gln Thr Pro Ser Phe Pro Asn Ile His Leu Gln Glu Asp
225                 230                 235                 240

Ile Ile Asn Arg Cys Glu Gln Phe Val Gly Pro Leu Thr Val Asn Glu
                245                 250                 255

Lys Arg Arg Leu Lys Leu Ile Met Pro Ala Arg Phe Tyr Pro Asn Val
            260                 265                 270

Thr Lys Tyr Leu Pro Leu Asp Lys Gly Ile Lys Pro Tyr Tyr Pro Glu
        275                 280                 285

His Leu Val Asn His Tyr Phe Gln Thr Arg His Tyr Leu His Thr Leu
    290                 295                 300

Trp Lys Ala Gly Ile Leu Tyr Lys Arg Glu Thr Thr Arg Ser Ala Ser
305                 310                 315                 320

Phe Cys Gly Ser Pro Tyr Ser Trp Glu Gln Glu Leu Gln His Gly Arg
                325                 330                 335

Leu Val Phe Gln Thr Ser Thr Arg His Gly Asp Glu Ser Phe Cys Gln
            340                 345                 350

Gln Ser Ser Gly Ile Leu Ser Arg Ser Pro Val Gly Pro Cys Leu Gln
        355                 360                 365

Ser Gln Leu Arg Lys Ser Arg Leu Gly Leu Gln Pro Gln Gln Gly His
    370                 375                 380

Leu Ala Arg Arg Gln Gln Gly Arg Ser Gly Ser Ile Arg Ala Arg Val
385                 390                 395                 400

His Pro Thr Thr Arg Arg Pro Phe Gly Val Glu Pro Ser Gly Ser Gly
```

```
              405             410             415
His Thr Thr Asn Thr Ala Ser Ser Ser Ser Cys Leu His Gln Ser
            420             425             430

Ala Val Arg Lys Ala Ala Tyr Ser His Leu Ser Thr Ser Lys Arg His
            435             440             445

Ser Ser Ser Gly His Ala Val Glu Leu His Asn Ile Pro Pro Asn Ser
            450             455             460

Ala Arg Ser Gln Ser Glu Gly Pro Val Phe Ser Cys Trp Trp Leu Gln
465             470             475             480

Phe Arg Asn Ser Lys Pro Cys Ser Asp Tyr Cys Leu Ser His Ile Val
                485             490             495

Asn Leu Leu Glu Asp Trp Gly Pro Cys Thr Glu His Gly Glu His His
            500             505             510

Ile Arg Ile Pro Arg Thr Pro Ala Arg Val Thr Gly Gly Val Phe Leu
            515             520             525

Val Asp Lys Asn Pro His Asn Thr Thr Glu Ser Arg Leu Val Val Asp
            530             535             540

Phe Ser Gln Phe Ser Arg Gly Asn Thr Arg Val Ser Trp Pro Lys Phe
545             550             555             560

Ala Val Pro Asn Leu Gln Ser Leu Thr Asn Leu Leu Ser Ser Asn Leu
                565             570             575

Ser Trp Leu Ser Leu Asp Val Ser Ala Ala Phe Tyr His Leu Pro Leu
            580             585             590

His Pro Ala Ala Met Pro His Leu Leu Val Gly Ser Ser Gly Leu Ser
            595             600             605

Arg Tyr Val Ala Arg Leu Ser Ser Asn Ser Arg Ile Ile Asn His Gln
            610             615             620

His Gly Thr Met Gln Asn Leu His Asp Ser Cys Ser Arg Asn Leu Tyr
625             630             635             640

Val Ser Leu Leu Leu Leu Tyr Lys Thr Phe Gly Arg Lys Leu His Leu
                645             650             655

Tyr Ser His Pro Ile Ile Leu Gly Phe Arg Lys Ile Pro Met Gly Val
            660             665             670

Gly Leu Ser Pro Phe Leu Leu Ala Gln Phe Thr Ser Ala Ile Cys Ser
            675             680             685

Val Val Arg Arg Ala Phe Pro His Cys Leu Ala Phe Ser Tyr Met Asn
            690             695             700

Asn Val Val Leu Gly Ala Lys Ser Val Gln His Leu Glu Ser Leu Phe
705             710             715             720

Thr Ala Val Thr Asn Phe Leu Leu Ser Leu Gly Ile His Leu Asn Pro
                725             730             735

Asn Lys Thr Lys Arg Trp Gly Tyr Ser Leu Asn Phe Met Gly Tyr Val
            740             745             750

Ile Gly Ser Trp Gly Thr Leu Pro Gln Glu His Ile Val Gln Lys Ile
            755             760             765

Lys Glu Cys Phe Arg Lys Leu Pro Val Asn Arg Pro Ile Asp Trp Lys
            770             775             780

Val Cys Gln Arg Ile Val Gly Leu Leu Gly Phe Ala Ala Pro Phe Thr
785             790             795             800

Gln Cys Gly Tyr Pro Ala Leu Met Pro Leu Tyr Ala Cys Ile Gln Ser
                805             810             815

Lys Gln Ala Phe Thr Phe Ser Pro Thr Tyr Lys Ala Phe Leu Cys Lys
            820             825             830
```

Gln Tyr Leu Asn Leu Tyr Pro Val Ala Arg Gln Arg Pro Gly Leu Cys
            835                 840                 845

Gln Val Phe Ala Asn Ala Thr Pro Thr Gly Trp Gly Leu Ala Ile Gly
    850                 855                 860

His Gln Arg Met Arg Gly Thr Phe Val Ala Pro Leu Pro Ile His Thr
865                 870                 875                 880

Ala Gln Leu Leu Ala Ala Cys Phe Ala Arg Ser Arg Ser Gly Ala Lys
            885                 890                 895

Leu Ile Gly Thr Asp Asn Ser Val Val Leu Ser Arg Lys Tyr Thr Ser
            900                 905                 910

Phe Pro Trp Leu Leu Gly Cys Ala Ala Asn Trp Ile Leu Arg Gly Thr
            915                 920                 925

Ser Phe Val Tyr Val Pro Ser Ala Leu Asn Pro Ala Asp Asp Pro Ser
            930                 935                 940

Arg Gly Arg Leu Gly Leu Tyr Arg Pro Leu Leu Arg Leu Pro Phe Arg
945                 950                 955                 960

Pro Thr Thr Gly Arg Thr Ser Leu Tyr Ala Asp Ser Pro Ser Val Pro
                965                 970                 975

Ser His Leu Pro Asp Arg Val His Phe Ala Ser Pro Leu His Val Ala
            980                 985                 990

Trp Arg Pro Pro
        995

<210> SEQ ID NO 21
<211> LENGTH: 1023
<212> TYPE: PRT
<213> ORGANISM: Artificial Sequence
<220> FEATURE:
<223> OTHER INFORMATION: HBV core-pol fusion antigen sequence with Ig
      signal sequence

<400> SEQUENCE: 21

Met Glu Phe Gly Leu Ser Trp Val Phe Leu Val Ala Ile Leu Lys Gly
1               5                   10                  15

Val Gln Cys Glu Val Gln Leu Leu Glu Ser Gly Met Asp Ile Asp Pro
            20                  25                  30

Tyr Lys Glu Phe Gly Ala Ser Val Glu Leu Leu Ser Phe Leu Pro Ser
        35                  40                  45

Asp Phe Phe Pro Ser Ile Arg Asp Leu Leu Asp Thr Ala Ser Ala Leu
    50                  55                  60

Tyr Arg Glu Ala Leu Glu Ser Pro Glu His Cys Ser Pro His His Thr
65                  70                  75                  80

Ala Leu Arg Gln Ala Ile Leu Cys Trp Gly Glu Leu Met Asn Leu Ala
            85                  90                  95

Thr Trp Val Gly Ser Asn Leu Glu Asp Pro Ala Ser Arg Glu Leu Val
            100                 105                 110

Val Ser Tyr Val Asn Val Asn Met Gly Leu Lys Ile Arg Gln Leu Leu
        115                 120                 125

Trp Phe His Ile Ser Cys Leu Thr Phe Gly Arg Glu Thr Val Leu Glu
    130                 135                 140

Tyr Leu Val Ser Phe Gly Val Trp Ile Arg Thr Pro Pro Ala Tyr Arg
145                 150                 155                 160

Pro Pro Asn Ala Pro Ile Leu Ser Thr Leu Pro Glu Thr Thr Val Val
                165                 170                 175

Ala Gly Ala Gly Met Pro Leu Ser Tyr Gln His Phe Arg Lys Leu Leu

```
                180                 185                 190
Leu Leu Asp Asp Glu Ala Gly Pro Leu Glu Glu Leu Pro Arg Leu
            195                 200                 205

Ala Asp Glu Gly Leu Asn Arg Arg Val Ala Glu Asp Leu Asn Leu Gly
210                 215                 220

Asn Leu Asn Val Ser Ile Pro Trp Thr His Lys Val Gly Asn Phe Thr
225                 230                 235                 240

Gly Leu Tyr Ser Ser Thr Val Pro Val Phe Asn Pro Glu Trp Gln Thr
                245                 250                 255

Pro Ser Phe Pro Asn Ile His Leu Gln Glu Asp Ile Ile Asn Arg Cys
            260                 265                 270

Glu Gln Phe Val Gly Pro Leu Thr Val Asn Glu Lys Arg Arg Leu Lys
        275                 280                 285

Leu Ile Met Pro Ala Arg Phe Tyr Pro Asn Val Thr Lys Tyr Leu Pro
    290                 295                 300

Leu Asp Lys Gly Ile Lys Pro Tyr Tyr Pro Glu His Leu Val Asn His
305                 310                 315                 320

Tyr Phe Gln Thr Arg His Tyr Leu His Thr Leu Trp Lys Ala Gly Ile
                325                 330                 335

Leu Tyr Lys Arg Glu Thr Thr Arg Ser Ala Ser Phe Cys Gly Ser Pro
            340                 345                 350

Tyr Ser Trp Glu Gln Glu Leu Gln His Gly Arg Leu Val Phe Gln Thr
        355                 360                 365

Ser Thr Arg His Gly Asp Glu Ser Phe Cys Gln Gln Ser Ser Gly Ile
    370                 375                 380

Leu Ser Arg Ser Pro Val Gly Pro Cys Leu Gln Ser Gln Leu Arg Lys
385                 390                 395                 400

Ser Arg Leu Gly Leu Gln Pro Gln Gln Gly His Leu Ala Arg Arg Gln
                405                 410                 415

Gln Gly Arg Ser Gly Ser Ile Arg Ala Arg Val His Pro Thr Thr Arg
            420                 425                 430

Arg Pro Phe Gly Val Glu Pro Ser Gly Ser Gly His Thr Thr Asn Thr
        435                 440                 445

Ala Ser Ser Ser Ser Ser Cys Leu His Gln Ser Ala Val Arg Lys Ala
    450                 455                 460

Ala Tyr Ser His Leu Ser Thr Ser Lys Arg His Ser Ser Ser Gly His
465                 470                 475                 480

Ala Val Glu Leu His Asn Ile Pro Pro Asn Ser Ala Arg Ser Gln Ser
                485                 490                 495

Glu Gly Pro Val Phe Ser Cys Trp Trp Leu Gln Phe Arg Asn Ser Lys
            500                 505                 510

Pro Cys Ser Asp Tyr Cys Leu Ser His Ile Val Asn Leu Leu Glu Asp
        515                 520                 525

Trp Gly Pro Cys Thr Glu His Gly Glu His His Ile Arg Ile Pro Arg
    530                 535                 540

Thr Pro Ala Arg Val Thr Gly Gly Val Phe Leu Val Asp Lys Asn Pro
545                 550                 555                 560

His Asn Thr Thr Glu Ser Arg Leu Val Val Asp Phe Ser Gln Phe Ser
                565                 570                 575

Arg Gly Asn Thr Arg Val Ser Trp Pro Lys Phe Ala Val Pro Asn Leu
            580                 585                 590

Gln Ser Leu Thr Asn Leu Leu Ser Ser Asn Leu Ser Trp Leu Ser Leu
        595                 600                 605
```

Asp Val Ser Ala Ala Phe Tyr His Leu Pro Leu His Pro Ala Ala Met
610                615                620

Pro His Leu Leu Val Gly Ser Ser Gly Leu Ser Arg Tyr Val Ala Arg
625                630                635                640

Leu Ser Ser Asn Ser Arg Ile Ile Asn His Gln His Gly Thr Met Gln
                645                650                655

Asn Leu His Asp Ser Cys Ser Arg Asn Leu Tyr Val Ser Leu Leu Leu
                660                665                670

Leu Tyr Lys Thr Phe Gly Arg Lys Leu His Leu Tyr Ser His Pro Ile
            675                680                685

Ile Leu Gly Phe Arg Lys Ile Pro Met Gly Val Gly Leu Ser Pro Phe
690                695                700

Leu Leu Ala Gln Phe Thr Ser Ala Ile Cys Ser Val Val Arg Arg Ala
705                710                715                720

Phe Pro His Cys Leu Ala Phe Ser Tyr Met Asn Asn Val Val Leu Gly
                725                730                735

Ala Lys Ser Val Gln His Leu Glu Ser Leu Phe Thr Ala Val Thr Asn
                740                745                750

Phe Leu Leu Ser Leu Gly Ile His Leu Asn Pro Asn Lys Thr Lys Arg
            755                760                765

Trp Gly Tyr Ser Leu Asn Phe Met Gly Tyr Val Ile Gly Ser Trp Gly
770                775                780

Thr Leu Pro Gln Glu His Ile Val Gln Lys Ile Lys Glu Cys Phe Arg
785                790                795                800

Lys Leu Pro Val Asn Arg Pro Ile Asp Trp Lys Val Cys Gln Arg Ile
                805                810                815

Val Gly Leu Leu Gly Phe Ala Ala Pro Phe Thr Gln Cys Gly Tyr Pro
                820                825                830

Ala Leu Met Pro Leu Tyr Ala Cys Ile Gln Ser Lys Gln Ala Phe Thr
            835                840                845

Phe Ser Pro Thr Tyr Lys Ala Phe Leu Cys Lys Gln Tyr Leu Asn Leu
850                855                860

Tyr Pro Val Ala Arg Gln Arg Pro Gly Leu Cys Gln Val Phe Ala Asn
865                870                875                880

Ala Thr Pro Thr Gly Trp Gly Leu Ala Ile Gly His Gln Arg Met Arg
                885                890                895

Gly Thr Phe Val Ala Pro Leu Pro Ile His Thr Ala Gln Leu Leu Ala
                900                905                910

Ala Cys Phe Ala Arg Ser Arg Ser Gly Ala Lys Leu Ile Gly Thr Asp
            915                920                925

Asn Ser Val Val Leu Ser Arg Lys Tyr Thr Ser Phe Pro Trp Leu Leu
930                935                940

Gly Cys Ala Ala Asn Trp Ile Leu Arg Gly Thr Ser Phe Val Tyr Val
945                950                955                960

Pro Ser Ala Leu Asn Pro Ala Asp Asp Pro Ser Arg Gly Arg Leu Gly
                965                970                975

Leu Tyr Arg Pro Leu Leu Arg Leu Pro Phe Arg Pro Thr Thr Gly Arg
            980                985                990

Thr Ser Leu Tyr Ala Asp Ser Pro Ser Val Pro Ser His Leu Pro Asp
            995                1000                1005

Arg Val His Phe Ala Ser Pro Leu His Val Ala Trp Arg Pro Pro
      1010                1015                1020

```
<210> SEQ ID NO 22
<211> LENGTH: 12
<212> TYPE: DNA
<213> ORGANISM: Artificial Sequence
<220> FEATURE:
<223> OTHER INFORMATION: linker coding sequence

<400> SEQUENCE: 22
gccggagctg gc                                                             12

<210> SEQ ID NO 23
<211> LENGTH: 248
<212> TYPE: DNA
<213> ORGANISM: Artificial Sequence
<220> FEATURE:
<223> OTHER INFORMATION: ApoAI gene fragment

<400> SEQUENCE: 23
ttggccgtgc tcttcctgac gggtaggtgt ccccctaacct agggagccaa ccatcggggg          60
gccttctccc taaatccccg tggcccaccc tcctgggcag aggcagcagg tttctcactg         120 gcccctctc ccccacctcc aagcttggcc tttcggctca gatctcagcc cacagctggc         180
ctgatctggg tctcccctcc caccctcagg gagccaggct cggcatttcg tcgacaagct         240
tagccacc                                                                 248

<210> SEQ ID NO 24
<211> LENGTH: 130
<212> TYPE: DNA
<213> ORGANISM: Artificial Sequence
<220> FEATURE:
<223> OTHER INFORMATION: SV40 polyadenylation signal sequence

<400> SEQUENCE: 24
aacttgttta ttgcagctta taatggttac aaataaagca atagcatcac aaatttcaca          60
aataaagcat ttttttcact gcattctagt tgtggtttgt ccaaactcat caatgtatct        120
tatcatgtct                                                               130
```

METHODS AND APPARATUS FOR THE DELIVERY OF HEPATITIS B VIRUS (HBV) VACCINES

CROSS REFERENCE TO RELATED APPLICATIONS

This application claims priority to U.S. Provisional Patent Application No. 62/607,430, filed Dec. 19, 2017, the disclosure of which is incorporated herein by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "688097-405 Sequence Listing," creation date of Dec. 10, 2018, and having a size of 46.6 KB. The sequence listing submitted via EFS-Web is part of the specification and is herein incorporated by reference in its entirety.

FIELD

The disclosure is directed to the administration of prophylactic and/or therapeutic Hepatitis B virus (HBV) vaccines to subjects in need thereof, and, more particularly, to the reproducible, consistent, and efficacious delivery of prophylactic and/or therapeutic HBV vaccines, such as nucleic acids encoding HBV antigens, to defined regions in selected tissue site of interest, facilitated by the local application of electrical fields, in a safe, effective, and consistent fashion across heterogeneous recipient populations with minimal user training.

BACKGROUND

Hepatitis B virus (HBV) is a small 3.2-kb hepatotropic DNA virus that encodes four open reading frames and seven proteins. About two billion people are infected with HBV, and approximately 240 million people have chronic hepatitis B infection (chronic HBV), characterized by persistent virus and subvirus particles in the blood for more than 6 months (Cohen et al. *J. Viral Hepat*. (2011) 18(6), 377-83). Persistent HBV infection leads to T-cell exhaustion in circulating and intrahepatic HBV-specific CD4+ and CD8+ T-cells through chronic stimulation of HBV-specific T-cell receptors with viral peptides and circulating antigens. As a result, T-cell polyfunctionality is decreased (i.e., decreased levels of IL-2, tumor necrosis factor (TNF)-α, IFN-γ, lack of proliferation, and degranulation). Therapeutic vaccination has the potential to eliminate HBV from chronically infected subjects (Michel et al. *J. Hepatol*. (2011) 54(6), 1286-1296). Immunogenic compositions containing one or more nucleic acid molecules encoding one or more HBV antigens can be used to provide therapeutic immunity to a subject in need thereof, such as a human having chronic HBV infection.

While naked DNA can be delivered to cells in vivo and result in gene expression, the efficiency of gene transfer is relatively low and variable. The local application of electrical signals has been shown to enhance the distribution and uptake of macromolecules in living tissue. Application of such electrical signals in tissue in association with the administration of a prophylactic or therapeutic HBV vaccine can have desirable effects on the tissue and/or the agent to be delivered. Specifically, techniques such as electroporation and iontophoresis have been utilized to significantly improve the distribution and/or uptake of nucleic acids, including both DNA and RNA sequences. Potential clinical applications of such techniques include the delivery of nucleic acid sequences for prophylactic and therapeutic immunization, and the delivery of nucleic acid sequences encoding therapeutic proteins or peptides.

The application procedures comprise the administration of an agent of interest to a target tissue site in conjunction with the application of electrical fields of sufficient magnitude and duration to induce the desired effects on the delivery, distribution, and/or potency of the agent. The electrical fields are propagated via two or more electrodes in electrically conductive communication with the tissue. Electrode configurations suitable for use with these techniques include tissue penetrating electrodes, surface contact electrodes, and air gap electrodes. Specific electrode configurations include, but are not limited to, elongate needle or rod electrodes, point electrodes, meander electrodes (i.e., shaped wire), planar electrodes, and combinations thereof. The specific type and arrangement of electrodes is selected based on the target tissue type and the objectives of the procedure. The desired outcome is best achieved when the electrical fields are propagated within the target tissue in the presence of the agent of interest.

A broad range of methods and devices have been described for the application of electrical fields in tissue in the presence of an agent of interest for the purpose of enhancing agent delivery in skin and muscle tissue. The devices include the use of both surface and tissue penetrating electrode systems as well as combinations thereof. In spite of the promise associated with electrically mediated agent delivery and the potential clinical applications of these techniques, there is still a need for reliable and consistent delivery of nucleic acids of interest to subjects. Significant sources of this variability are due to differences in the technique and skill level of the operator. Other sources of variability that are not addressed by current systems include differences in the physiologic characteristics between subjects that can affect the application of the procedure. Other considerations for the development of suitable devices include their ease of use and the implementation of designs that reduce the frequency and significance of potential user errors.

Given that safe, reliable, accurate, and consistent application of clinical therapies is highly desirable, the development of improved application systems is well warranted. Such development should include a means for minimizing operator-associated variability while providing a means to accommodate the differences in subject characteristics likely to be encountered during widespread clinical application of electrically mediated agent delivery. In other words, specific areas for refinement include the ability to maintain consistent performance across heterogeneous recipient populations and a reduction in the level of training and skill required for effective use by the user. In addition, the device, system or method should be designed to facilitate avoidance of user or device errors and minimize their impact when they occur.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY OF THE DISCLOSURE

The disclosure provides apparatus, kits and methods for the reproducible, consistent, and efficacious delivery of an HBV vaccine comprising a nucleic acid molecule encoding an HBV antigen, to a subject in need thereof, utilizing Electrically Mediated Therapeutic Agent Delivery (EMTAD). In embodiments described herein, the therapeutic agent is an HBV vaccine.

In an aspect of the disclosure, provided is an apparatus for the delivery of an HBV vaccine to a predetermined site within a subject comprising an assembly for controlled administration of the HBV vaccine to the subject comprising a reservoir containing the HBV vaccine, at least one orifice through which the agent is administered, and a controlled source of energy sufficient to transfer a predetermined amount of the HBV vaccine at a predetermined rate from the reservoir through the orifice to the predetermined site within the subject. In addition, the apparatus can comprise a plurality of penetrating electrodes arranged with a predetermined spatial relationship relative to the orifice, and an electrical signal generator operatively connected to the electrodes.

In another aspect of the disclosure, provided is a kit for the delivery of an HBV vaccine to a predetermined site within a subject, comprising the HBV vaccine and an apparatus comprising an assembly for controlled administration of the HBV vaccine to the subject, wherein the apparatus comprises a reservoir for the HBV vaccine, at least one orifice through which the HBV vaccine is administered, and a controlled source of energy sufficient to transfer a predetermined amount of the HBV vaccine at a predetermined rate from the reservoir through the orifice to the predetermined site within the subject. In addition, the apparatus can comprise a plurality of penetrating electrodes arranged with a predetermined spatial relationship relative to the orifice, and electrical signal generator operatively connected to the electrodes.

An HBV vaccine included in an apparatus or a kit of the present application can comprise:

a first nucleic acid molecule comprising a first polynucleotide encoding an HBV polymerase antigen having an amino acid sequence that is at least 98% identical to SEQ ID NO: 4, wherein the HBV polymerase antigen does not have reverse transcriptase activity and RNase H activity;

a second nucleic acid molecule comprising a second polynucleotide encoding a truncated HBV core antigen consisting of the amino acid sequence of SEQ ID NO: 2 or SEQ ID NO: 14; and a pharmaceutically acceptable carrier, wherein the first nucleic acid molecule and the second nucleic acid molecule are present in the same nucleic acid molecule or in two different nucleic acid molecules.

Other aspects of the disclosure include methods comprising HBV vaccine administration in controlled spatial and temporal relation with Electric Signal Administration (ESA).

Benefits and advantages to certain implementations according to present principles are manifold. Some implementations allow the selection of depth of needle and electrode insertion, allowing insertion into various types of desired tissue, (e.g., dermis, muscle, etc.) across heterogeneous populations of varying body mass and body composition. These implementations also facilitate adaptation of the methods for use in specific target populations, for instance, but not restricted to, human patients having chronic HBV infection and/or an HBV-induced disease. Provided herein are systems and methods comprising design features that render the systems and methods resistant to accidental discharge or potential misuse, e.g., due to dropping, jarring, and/or falling. In some embodiments are provided devices configured for multiple injection depths. Systems and methods according to present principles allow numerous safety interlocks to reduce the frequency and/or impact of user errors. These include features to facilitate proper preparation and configuration of the dose to be administered, ensuring that the device is applied with requisite force to the tissue of the recipient, ensuring that a safety cap has been removed, and so on. Systems, apparatus, kits and methods according to present principles can allow for a highly consistent therapy to be delivered irrespective of administrator or the type of recipient. Systems, apparatus, kits and methods described herein can allow for, e.g., a consistent force profile to be obtained prior to and during delivery of the therapy, so that recipients with varying skin and muscular characteristics can be dosed consistently.

This Summary is provided to introduce a selection of concepts in a simplified form. The concepts are further described in the Detailed Description section. Elements or steps other than those described in this Summary are possible, and no element or step is necessarily required. This Summary is not intended to identify key features or essential features of the claimed subject matter, nor is it intended for use as an aid in determining the scope of the claimed subject matter. The claimed subject matter is not limited to implementations that solve any or all disadvantages noted in any part of this disclosure.

Other aspects, features and advantages of the invention will be apparent from the following disclosure, including the detailed description of the invention and its preferred embodiments and the appended claims.

BRIEF DESCRIPTION OF THE DRAWINGS

The features of the disclosure are set forth with particularity in the appended claims. A better understanding of the features and advantages of the disclosure will be obtained by reference to the following detailed description that sets forth illustrative embodiments, in which the principles of the disclosure are utilized, and the accompanying drawings of which:

FIG. 1 illustrates potential sources of spatial variability associated with conventional needle syringe injection.

FIG. 2 is an overview of a system according to present principles, including a cartridge assembly 100, an applicator 400, and a controller system 700.

FIGS. 3A-3B show views of aspects of a device described herein. FIG. 3A shows a lateral view of a cartridge assembly 100 according to present principles. FIG. 3B shows a lateral view of a reservoir for HBV vaccine 101 embodied as a syringe, according to present principles.

FIG. 4 shows various exemplary components of a cartridge assembly 100 according to present principles.

FIGS. 5A-5E show views of aspects of an inner cartridge and cartridge breech in a device described herein. FIG. 5A illustrates a top view of an inner cartridge 103 according to present principles. FIG. 5B illustrates a bottom view of an inner cartridge 103 and cartridge breech according to present principles. FIG. 5C illustrates a detail side perspective view of an inner cartridge 103 according to present principles. FIG. 5D shows a lateral view of a cartridge breech 112 according to present principles. FIG. 5E illustrates reservoir interlock 120 with improved locking features to prevent the cartridge breech 112 from inadvertently moving forward.

FIG. 6 illustrates details of a cartridge assembly showing a rack 154, a initiating flag 172, and a continuing flag 174 according to present principles.

FIGS. 7A-7B show views of aspects of electrodes and/or electrode contacts in a device described herein. FIG. 7A shows details of electrode contacts 130 and various electrode contact portions according to present principles. FIG. 7B shows details of electrodes 122 and various electrode contacts portions according to present principles.

FIGS. 8A-8B show views of aspects of a force contact interlock system in a device described herein. FIG. 8A shows a top view of a force contact interlock system according to the present principle. FIG. 8B illustrates details of a force contact interlock system according to present principles.

FIGS. 9A-9D show views of aspects of a device described herein. FIG. 9A shows a needle 105 and distal inner cartridge electrodes 137 for tissue insertion according to present principles. FIG. 9B illustrates details of a stick shield 134 according to present principles. FIG. 9C illustrates an alignment guide 108 and splay shield 168 according to present principles. FIG. 9D illustrates stick shield supports intergral to outer cartridge cap 106.

FIGS. 10A-10D show views of aspects of exterior cartridge cap in a device described herein. FIG. 10A shows an exterior cartridge cap 110 according to present principles. FIG. 10B shows a side view of an exterior cartridge cap 110 according to present principles. FIG. 10C shows an exterior cartridge cap 110 in use in an alignment guide 108 and splay shield according to present principles. FIG. 10D shows an exterior cartridge cap 110 with extension members designed to hold the inner cartridge 103 in place during handling and loading.

FIGS. 11A-11C show details of stick shields in aspects of a device described herein. FIG. 11A shows a stick shield retaining hook 182 of a stick shield 134 according to present principles. FIG. 11B shows details of a stick shield 134 according to present principles. FIG. 11C shows stick shield supports 132 keeping a stick shield 134 in place according to present principles.

FIG. 12 shows details of an electrode support 124 according to present principles.

FIGS. 13A-13B show views of an applicator in a device described herein. FIG. 13A shows a side view of an applicator 400 according to present principles. FIG. 13B shows top views of an applicator 400 according to present principles.

FIGS. 17A-17B show views of an applicator in a device described herein. FIG. 17A is an exploded view of an applicator according to present principles, showing a loading drive subassembly 454. FIG. 17B shows a rack 154 in a loading drive subassembly 454 according to present principles.

Figure 18A:
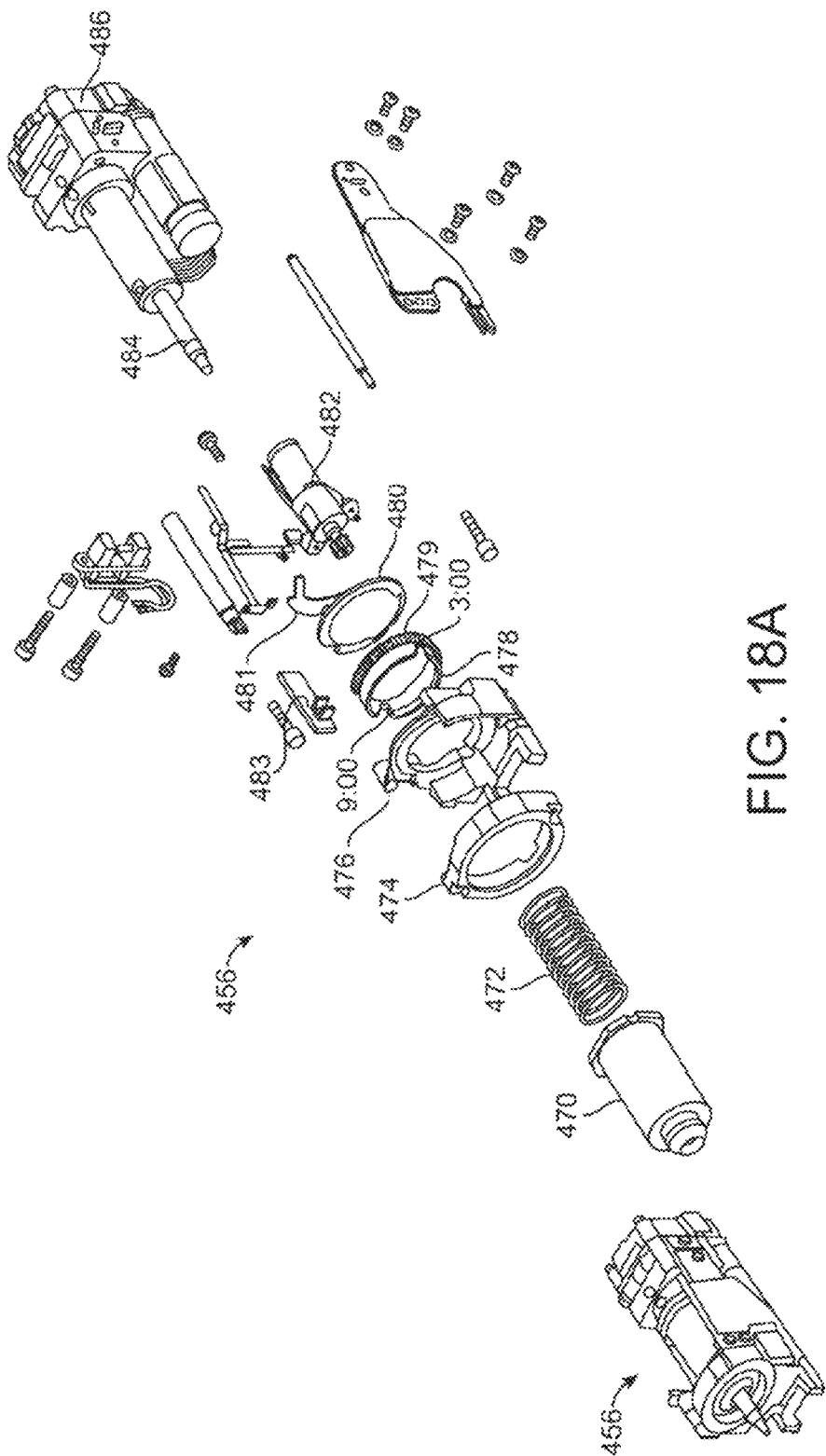
Figure 18B:
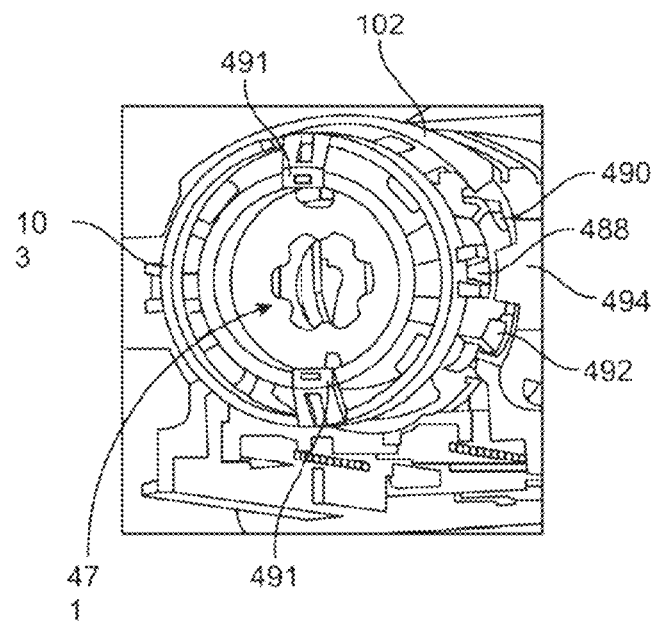
Figure 18C:
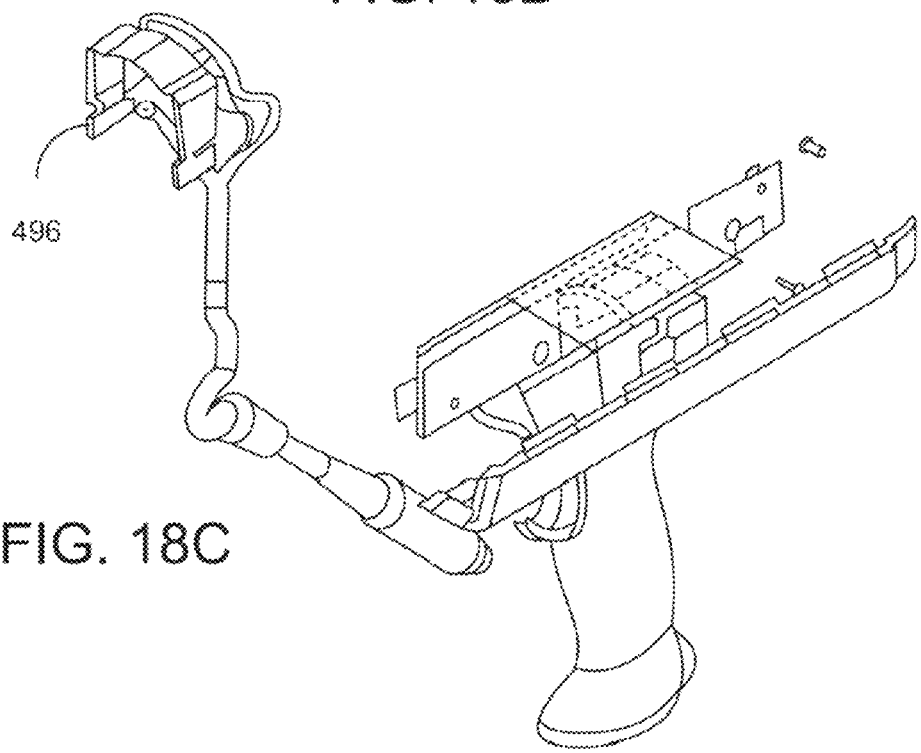

FIGS. 18A-18C show views of aspects of an applicator in a device described herein. FIG. 18A shows details of a cartridge loading subassembly 456 according to present principles, showing where the insertion/injection drive assembly of the applicator mates with the cartridge assembly. FIG. 18B shows a cross-sectional view of a cartridge assembly according to present principles, showing where the insertion/injection drive assembly of the applicator mates with the cartridge assembly. FIG. 18C shows details of cartridge loading, electrode insertion, and injection subassemblies 452 of an applicator 400 according to present principles.

Figure 19:
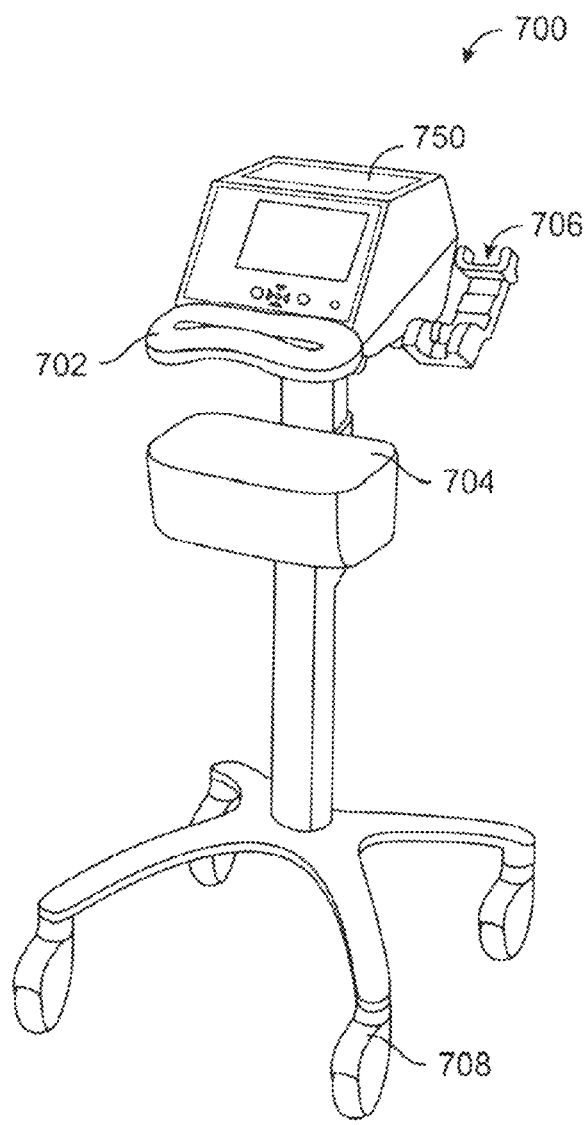

FIG. 19 shows various components of a controller system according to present principles.

Figure 20C:
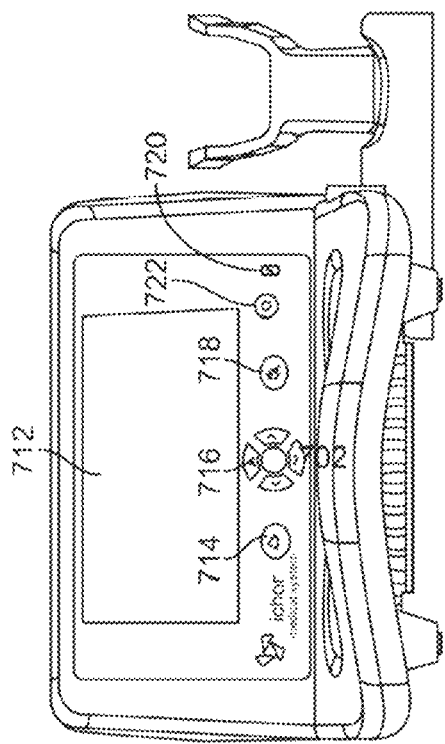
Figure 20D:
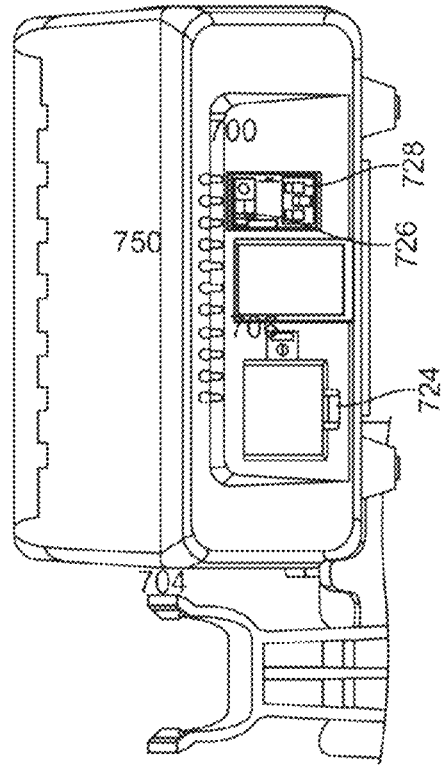
Figure 20A:
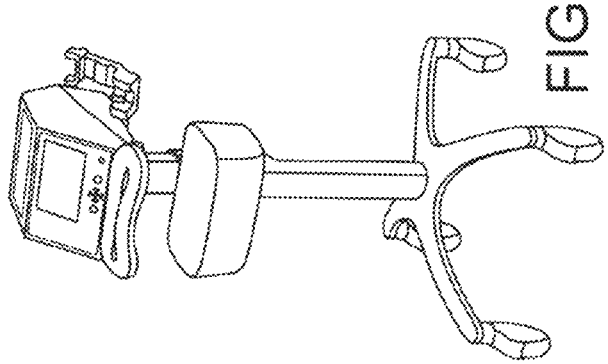
Figure 20B:
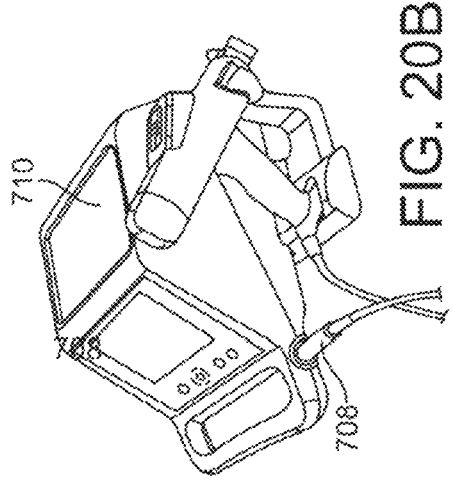

FIGS. 20A-20D show views of a device described herein. FIG. 20A shows various components of a controller system according to present principles. FIG. 20B shows details of an applicator connector port 708 and a tray 710 of a controller system according to present principles. FIG. 20C shows details of a stimulator display screen of a controller system according to present principles. FIG. 20D shows details of a rear view of a controller system according to the present principles.

Figure 21:
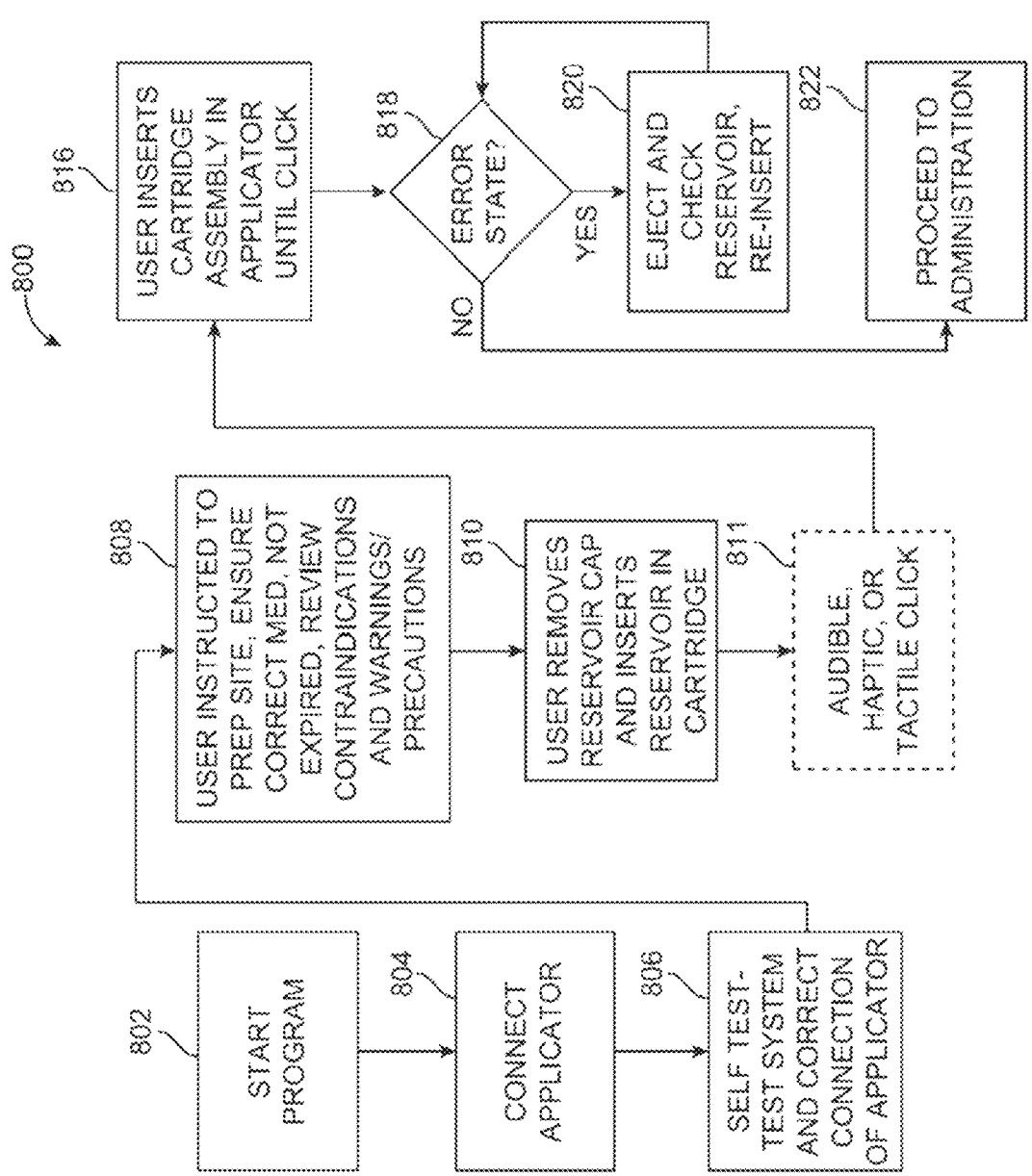

FIG. 21 is a flowchart showing a method of operation according to present principles.

Figure 22:
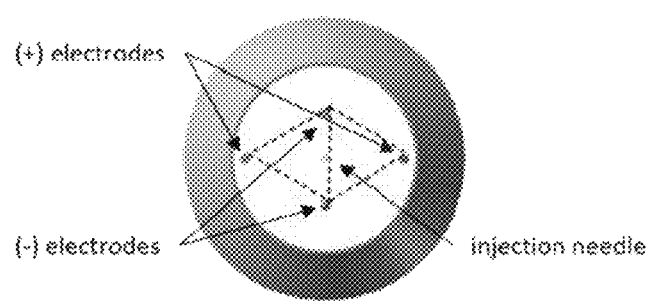

FIG. 22 illustrates TriGrid electrode array (cross-section) for intramuscular (IM) delivery, which is comprised of four electrodes arranged in two equilateral triangles to form a diamond shape surrounding a central injection needle.

Figure 23A:
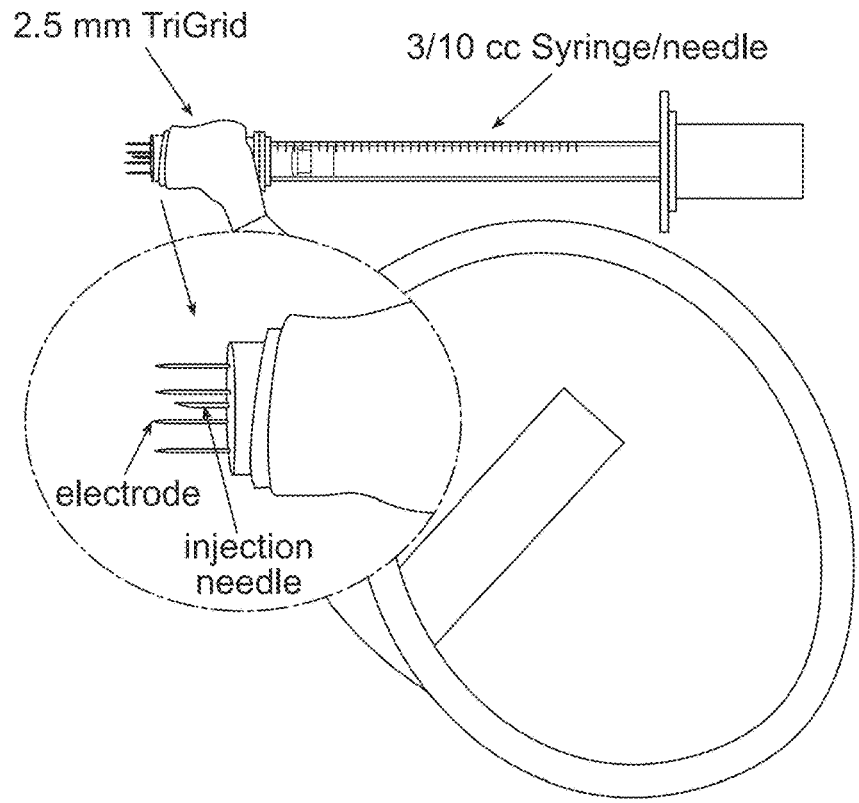
Figure 23B:
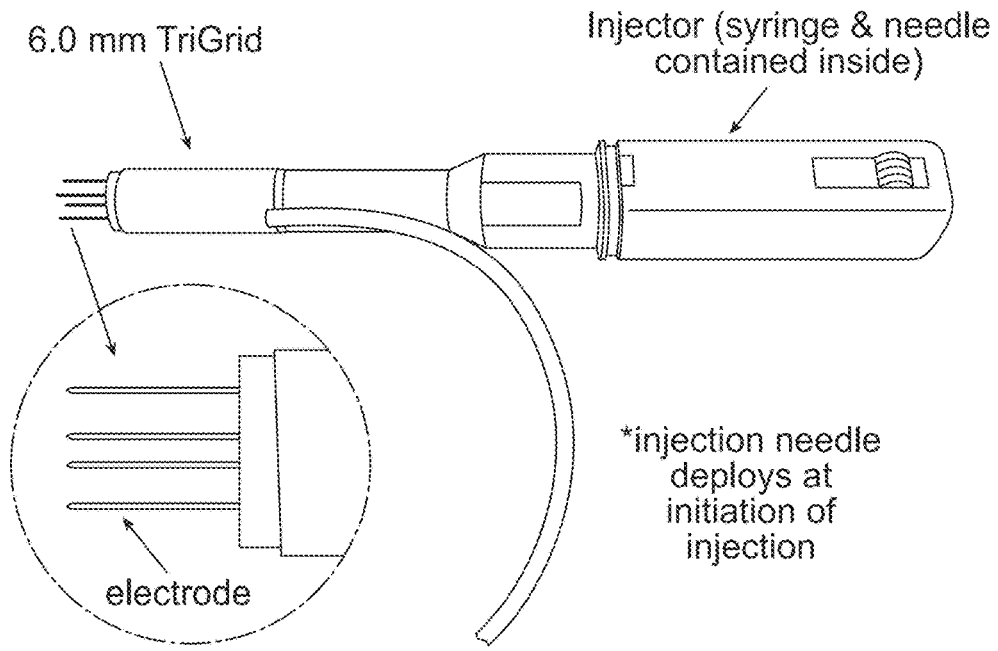

FIGS. 23A-23B depict the TDS-IM v1.0 TriGrid devices adapted for use in the mouse model (FIG. 23A) and the non-human primate (NHP) model (FIG. 23B).

Figure 24:
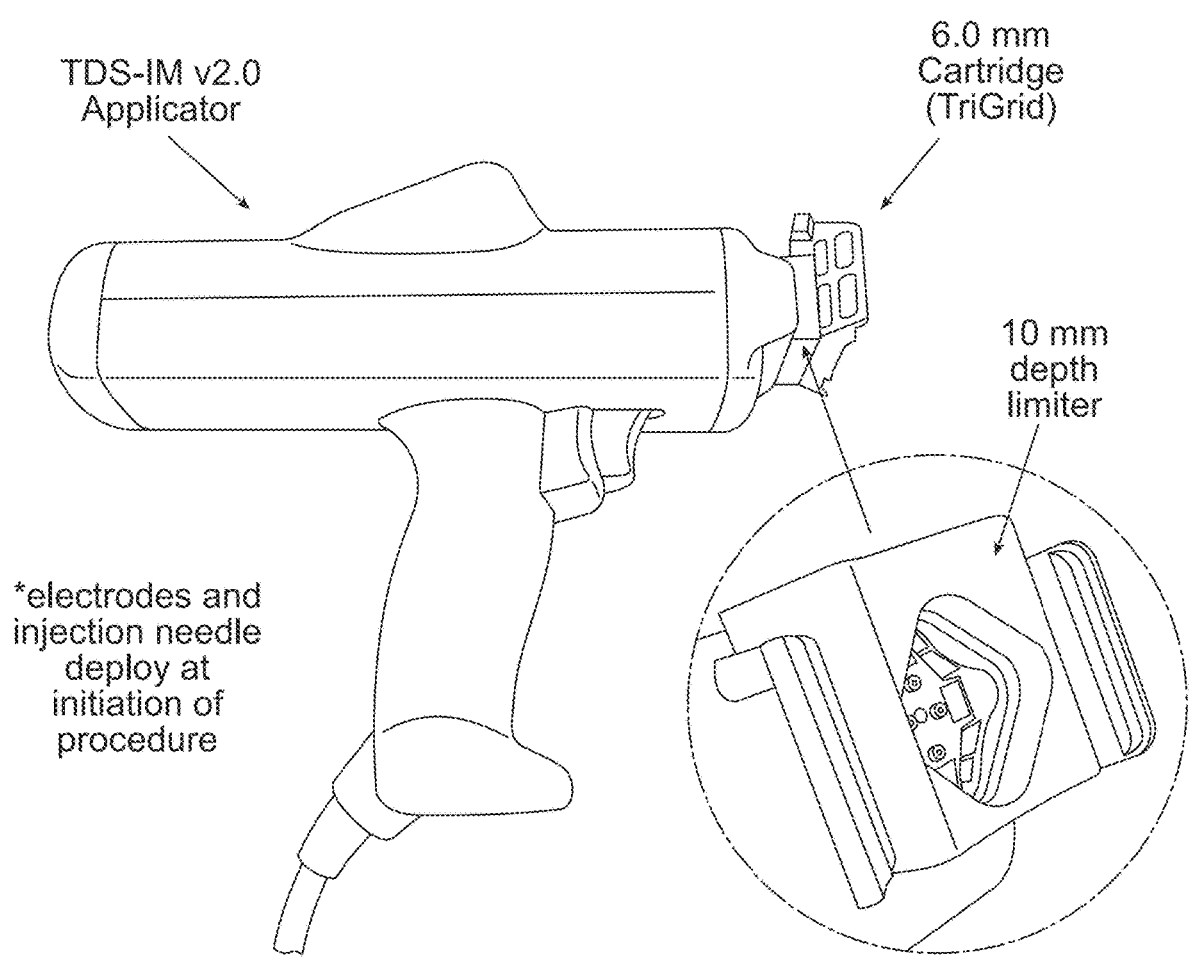

FIG. 24 depicts the TDS-IM v2.0 TriGrid device adapted for use in the non-human primate (NHP) model.

Figure 25:
Figure 25:
Figure 25:
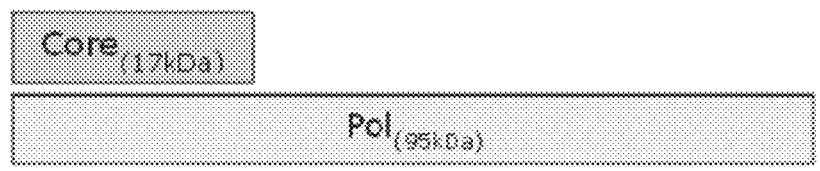
Figure 25:
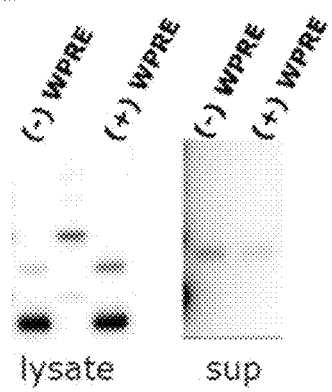
Figure 25:
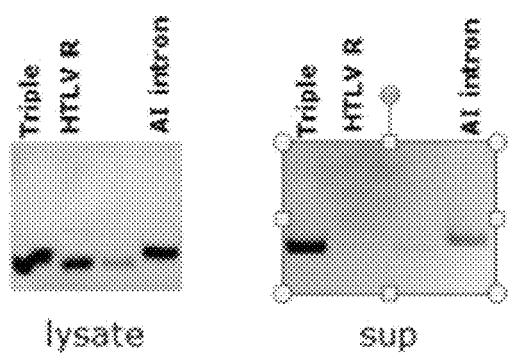
Figure 25:
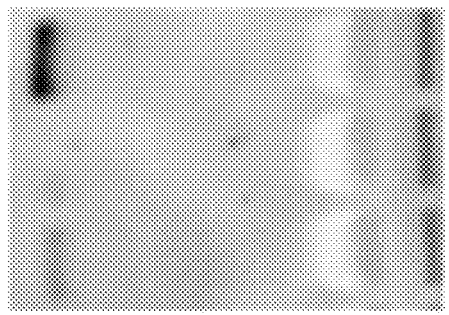
Figure 25:
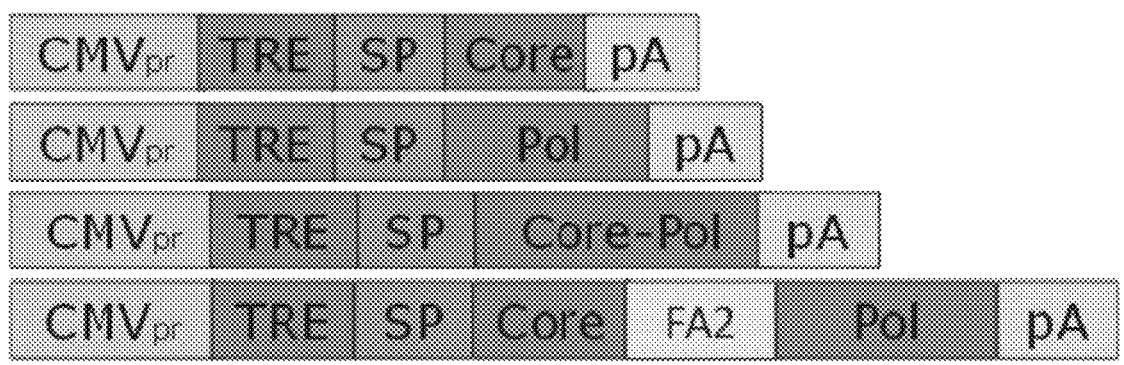
Figure 25:
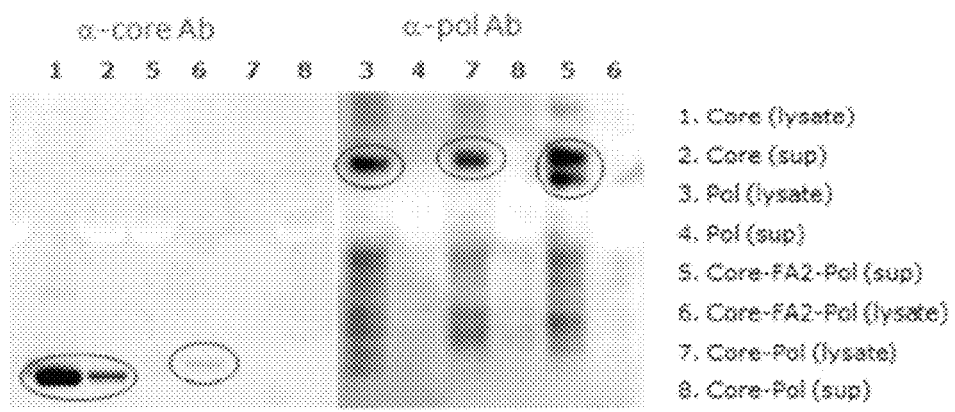
Figure 26A:
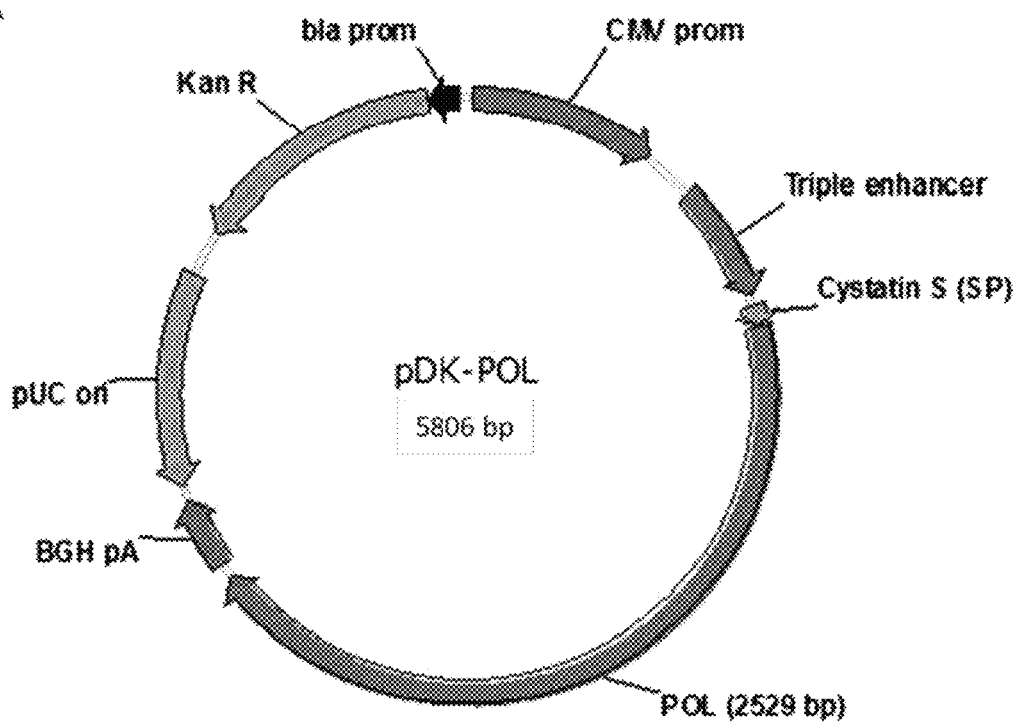
Figure 26B:
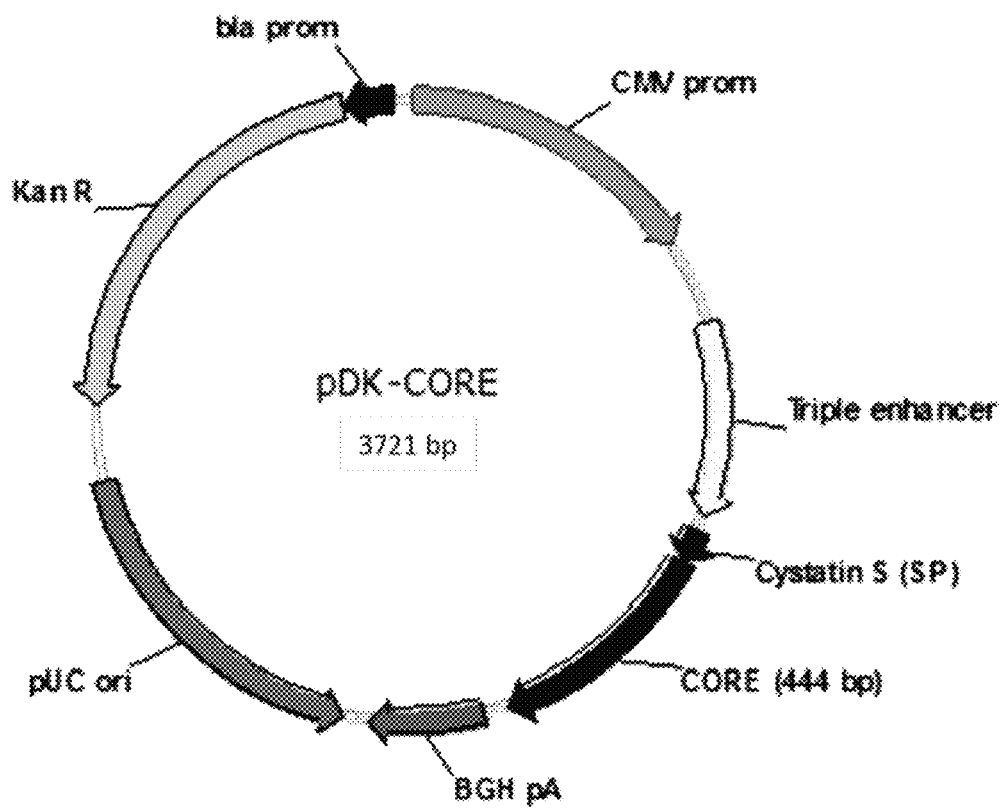

FIGS. 25A-25H show the design and optimization of expression cassettes and DNA plasmids encoding HBV pol and core antigens as described in Example 1; FIG. 25A is a schematic representation of an expression strategy in which coding sequences of the HBV core and pol antigens are fused in frame; FIG. 25B is a schematic representation of an expression strategy in which coding sequences of both the core and pol antigens are expressed from a single plasmid by means of the ribosomal FA2 slippage site; FIG. 25C is a schematic representation of an expression strategy in which the core and pol antigens are expressed from two separate plasmids; FIG. 25D is a Western blot of core antigen expression in HEK293T cells transfected with a plasmid expressing core with and without the post-transcriptional regulatory element WPRE; expression was tested in cell lysate (left) and supernatant (sup; right) using an α-core antibody; FIG. 25E is a Western blot analysis showing a comparison of core expression in HEK293T cells transfected with a core expressing plasmid including the intron/exon sequence derived from human apolipoprotein A1 precursor ("AI intron"), untranslated R-U5 domain of the human T-cell leukemia virus type 1 (HTLV-1) long terminal repeat (LTR) ("HTLV R"), or triple enhancer composite sequence of the HTLV-1 LTR, synthetic rabbit β-globin intron, and a splicing enhancer ("triple"); the unlabeled lane is purified core protein as a size marker; expression was tested in both lysate (left) and supernatant (sup; right); core antigen expression was highest with the triple enhancer composite sequence; FIG. 25F is a Western blot analysis of core antigen secretion using different signal peptides fused to the N-terminus of the HBV core antigen; the most efficient protein secretion was observed with the Cystatin S signal peptide; FIG. 25G is a schematic representation of optimized HBV core/pol antigen expression cassettes for each of the three expression strategies illustrated in FIGS. 25A-25C; CMVpr: human CMV-IE promoter; TRE: triple enhancer sequence; SP: cystatin S signal peptide; FA2: FMDV ribosomal slippage site; pA: BGH polyadenylation signal; FIG. 25H is a Western blot analysis of HBV core and pol antigen expression of pDK vectors containing each of the expression cassettes shown in FIG. 25G; lanes 1 and 2: pDK-core; lanes 3 and 4: pDK-pol; lanes 5 and 6: pDK-coreFA2Pol; lanes 7 and 8: pDK-core-pol fusion: the most consistent expression profile for cellular and secreted core and pol antigens was observed when the antigens were encoded by separate vectors;

FIGS. 26A-26B show schematic representations of DNA plasmids according to embodiments of the application; FIG. 26A shows a DNA plasmid encoding an HBV polymerase (pol) antigen according to an embodiment of the application; FIG. 26B shows a DNA plasmid encoding an HBV core antigen according to an embodiment of the application; the HBV core and pol antigens are expressed under control of a CMV promoter with an N-terminal cystatin S signal peptide that is cleaved from the expressed antigen upon secretion from the cell; transcriptional regulatory elements of the plasmid include an enhancer sequence located between the CMV promoter and the polynucleotide sequence encoding the HBV antigen and a bGH polyadenylation sequence located downstream of the polynucleotide sequence encoding the HBV antigen; a second expression cassette is included in the plasmid in reverse orientation including a kanamycin resistance gene under control of an Amp' (bla) promoter; an origin of replication (pUC) is also included in reverse orientation;

Like reference numerals refer to like elements throughout. Elements are not to scale unless otherwise noted.

DETAILED DESCRIPTION

The following description and examples illustrate embodiments of the invention in detail. It is to be understood that this invention is not limited to the particular embodiments described herein and as such can vary. Those of skill in the art will recognize that there are numerous variations and modifications of this invention, which are encompassed within its scope.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the invention can be described in the context of a single embodiment, the features may also be provided separately or in any suitable combination. Conversely, although the invention can be described herein in the context of separate embodiments for clarity, the invention may also be implemented in a single embodiment.

In an attempt to help the reader of the application, the description has been separated in various paragraphs or sections, or is directed to various embodiments of the application. These separations should not be considered as disconnecting the substance of a paragraph or section or embodiments from the substance of another paragraph or section or embodiments. To the contrary, one skilled in the art will understand that the description has broad application and encompasses all the combinations of the various sections, paragraphs and sentences that can be contemplated. The discussion of any embodiment is meant only to be exemplary and is not intended to suggest that the scope of the disclosure, including the claims, is limited to these examples. For example, while embodiments of HBV vectors that can be used in the application (e.g., plasmid DNA or viral vectors) described herein may contain particular components, including, but not limited to, certain promoter sequences, enhancer or regulatory sequences, signal peptides, coding sequence of an HBV antigen, polyadenylation signal sequences, etc. arranged in a particular order, those having ordinary skill in the art will appreciate that the concepts disclosed herein may equally apply to other components arranged in other orders that can be used in HBV vectors useful for the application. The application contemplates use of any of the applicable components in any combination having any sequence that can be used in HBV vectors useful for the application, whether or not a particular combination is expressly described.

The following definitions supplement those in the art and are directed to the current application and are not to be imputed to any related or unrelated case, e.g., to any commonly owned patent or application. Although any methods and materials similar or equivalent to those described herein can be used in the practice for testing of the disclosure, the preferred materials and methods are described herein. Accordingly, the terminology used herein is for the purpose of describing particular embodiments only, and is not intended to be limiting.

In this application, the use of the singular includes the plural unless specifically stated otherwise. It must be noted that, as used in the specification, the singular forms "a," "an" and "the" include plural references unless the context clearly dictates otherwise. In this application, the use of "or" means "and/or" unless stated otherwise. Furthermore, use of the term "including" as well as other forms, such as "include", "includes," and "included," is not limiting.

Reference in the specification to "some embodiments," "an embodiment," "an embodiment" or "other embodiments" means that a particular feature, structure, or characteristic described in connection with the embodiments is included in at least some embodiments, although not necessarily all embodiments, of the inventions.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the invention, and vice versa. Furthermore, compositions of the invention can be used to achieve methods of the invention.

The term "about" in relation to a reference numerical value and its grammatical equivalents as used herein can include the numerical value itself and a range of values plus or minus 10% from that numerical value. For example, the amount "about 10" includes 10 and any amounts from 9 to 11. For example, the term "about" in relation to a reference numerical value can also include a range of values plus or minus 10%, 9%, 8%, 7%, 6%, 5%, 4%, 3%, 2%, or 1% from that value.

The disclosure provides improved system, kits, methods and apparatus for the reproducible, consistent, and efficacious delivery of HBV vaccines, such as nucleic acids encoding HBV antigens and combinations thereof with Electrically Mediated Therapeutic Agent (e.g., HBV vaccine) Delivery (EMTAD).

In an aspect, the disclosure provides an apparatus for the delivery of an HBV vaccine to a predetermined site within a subject, comprising a cartridge assembly comprising an outer cartridge, an inner cartridge, a reservoir containing the HBV vaccine, wherein a reservoir containment volume is contained within the outer cartridge and configured to receive the reservoir; an applicator comprising a cartridge assembly receiving volume, a needle hub, and an insertion detector, wherein the insertion detector senses loading of the reservoir in the reservoir containment volume; at least one interlock, wherein the interlock facilitates proper execution of the HBV vaccine administration procedure; at least one injection orifice through which the HBV vaccine is administered; a plurality of penetrating electrodes arranged with a predetermined spatial relationship relative to the orifice; an electrical field generator for generating an electrical signal operatively connected to the electrodes; and a controlled source of energy sufficient to transfer a predetermined amount of the HBV vaccine at a predetermined rate from the reservoir through the orifice to the predetermined site within the subject.

In another aspect, the disclosure provides a kit for the delivery of an HBV vaccine to a predetermined site within a subject, comprising the HBV vaccine, and an apparatus comprising a cartridge assembly comprising an outer cartridge, an inner cartridge, a reservoir for the HBV vaccine, wherein a reservoir containment volume is contained within the outer cartridge and configured to receive the reservoir; an applicator comprising a cartridge assembly receiving volume, a needle hub, and an insertion detector, wherein the insertion detector senses loading of the reservoir in the reservoir containment volume; at least one interlock, wherein the interlock facilitates proper execution of the HBV vaccine administration procedure; at least one injection orifice through which the HBV vaccine is administered; a plurality of penetrating electrodes arranged with a predetermined spatial relationship relative to the orifice; an electrical field generator for generating an electrical signal operatively connected to the electrodes; and a controlled source of energy sufficient to transfer a predetermined amount of the HBV vaccine at a predetermined rate from the reservoir through the orifice to the predetermined site within the subject.

An HBV vaccine included in an apparatus or a kit of the present application can comprise:
 a first nucleic acid molecule comprising a first polynucleotide encoding an HBV polymerase antigen having an amino acid sequence that is at least 98% identical to SEQ ID NO: 4, wherein the HBV polymerase antigen does not have reverse transcriptase activity and RNase H activity;
 a second nucleic acid molecule comprising a second polynucleotide encoding a truncated HBV core antigen consisting of the amino acid sequence of SEQ ID NO: 2 or SEQ ID NO: 14; and
 a pharmaceutically acceptable carrier,
 wherein the first nucleic acid molecule and the second nucleic acid molecule are present in the same nucleic acid molecule or in two different nucleic acid molecules.

In certain aspects of the disclosure, EMTAD can be referred to as the administration of an HBV vaccine to a biological tissue of interest and the earlier, concurrent or subsequent application of electrical signals to biological tissue for the purpose of enhancing movement and/or uptake of the HBV vaccine in said tissue. The process of EMTAD is comprised of two elements: 1) Therapeutic Agent (i.e., HBV vaccine) Administration (TAA), and 2) an Electrical Signal Application (ESA) sufficient to induce the desired EMTAD effect. In the disclosure, TAA can be accomplished, for instance, in a controllable fashion, termed Controlled Therapeutic Agent (e.g., HBV vaccine) Administration (CTAA). The term CTAA used herein can refer to methods or apparatus that provide spatial and/or temporal control over administration of an HBV vaccine relative to the induction of an EMTAD effect. Controllable administration techniques can utilize variations on the conventional needle-syringe (e.g. automatic injection device) and/or various needleless methodologies (e.g. jet injector, transdermal/transcutaneous patch, oral, gel, cream, or inhaled administration). The term ESA used herein can refer to the application of electrical signals to facilitate or enhance the delivery of active agents, e.g., HBV vaccines, by improving movement and/or uptake of said agents within tissue, thus inducing an EMTAD effect. When used to facilitate or enhance delivery of an HBV vaccine, ESA processes such as electroporation, iontophoresis, electroosmosis, electropermeabilization, electrostimulation, electromigration, and electroconvection all represent various modes of EMTAD, one or more of which can be included in the methods described herein.

Specific applications for apparatus, kits and systems described herein include, but are not limited to, the delivery of HBV vaccines containing one or more than one nucleic acid molecules. Traditionally with such applications, EMTAD is initiated by HBV vaccine injection using a conventional needle-syringe. After the agent has been administered, a device suitable for ESA is applied to the subject at a designated location. Finally, an appropriate ESA protocol is utilized to provide the desired facilitation or enhancement to HBV vaccine delivery. With traditional EMTAD, however, the desired spatial and temporal relationship between agent administration and ESA may not be realized.

Spatial Parameters

Figure 1:
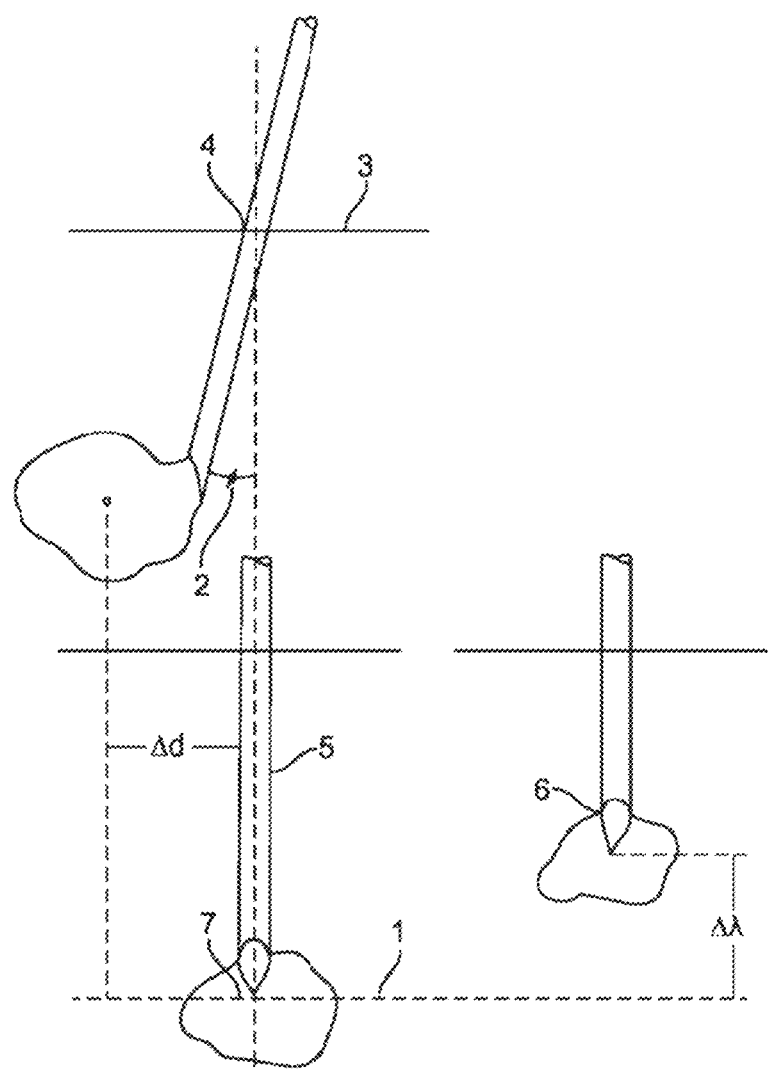

In some embodiments of the systems, kits, methods and apparatus described herein, HBV vaccine administration is performed using a conventional needle syringe. The need to deliver certain agents with EMTAD brings an additional level of complexity to the issue of TAA. As depicted in FIG. 1, in any conventional needle-syringe injection, as the needle 5 is inserted into the tissue, the depth 1 and the angle 2 of insertion relative to the surface of the tissue 3 can be difficult to control. Additionally, the point of needle penetration 4 at the tissue surface 3 may not be representative of the location of the orifice 6 and the region of agent administration 7 within the target tissue. As an illustrative example a transcutaneous intramuscular injection may not correspond to the site of insertion on the skin since the two tissues can often move in relation to one another.

While this conventional approach is generally adequate for the delivery of many different therapeutics that do not require EMTAD, these variables lead to a distribution of the HBV vaccine following injection that is often inconsistent and/or indeterminate and can hamper effective EMTAD. In certain embodiments described herein, the most effective use of EMTAD utilizes a predefined relationship between the HBV vaccine and ESA within the subject. As a result, in the absence of spatial control over TAA in a target tissue, using a conventional needle syringe can result in reduced effectiveness of the EMTAD application, as compared to an apparatus, method or system that provides spatial and temporal control. One illustrative example of this concept is the use of electroporation to facilitate the delivery of an HBV vaccine. Electroporation is typically most effective in enhancing HBV vaccine delivery when TAA and ESA are co-localized within the target region of tissue. In many cases, if the agent to be delivered and the induced electroporation effect are not co-localized within the target region of tissue, the delivery of said agent is suboptimal.

Another example of the need for adequate spatial control of TAA in EMTAD is iontophoresis. This mode of EMTAD uses electrical fields to cause movement of charged molecules. In order to achieve the desired movement of the agent, the proper spatial relationship between the electrodes and the HBV vaccine must be realized. If a negatively charged agent were placed in close proximity to the location of a positive electrode, little or no movement of the agent through the tissue would be observed. In contrast, localization of the said negatively charged agent near the negative electrode would result in significant movement of the agent through the tissue in the direction of the positive electrode.

As illustrated by the preceding examples, it is important to control the precise location of TAA relative to the application of ESA to achieve the desired effect. As such, embodiments of the apparatus and methods described herein provide control of the precise location of TAA relative to the application of ESA, and are useful to achieve reproducible, consistent, and well-characterized distribution of one or more HBV vaccines.

Temporal Parameters

In the case of conventional needle-syringe injection TAA is that the rate of injection may vary from one operator to another, thereby causing inconsistent agent distribution in the tissue. Additional temporal variability is introduced when multiple device placements are required to complete the EMTAD process. For example, one application of EMTAD calls for the administration of plasmid DNA encoding for a therapeutic protein, followed by generation of an electroporation-inducing electrical field. Using the traditional method of EMTAD, the HBV vaccine is injected with a needle-syringe, followed by placement and activation of the electroporation device. By requiring two separate device placements (the initial needle syringe followed by the ESA device), this procedure is susceptible to inter-subject variability arising from inconsistent temporal application of each device by the operator. Additionally, the use of two separate device placements leads to an unavoidable time interval in between the clinician's placement and activation of each device. This is compounded in the case where multiple application sites are necessary to achieve adequate delivery of the agent to a specifiable region within the target tissue.

These issues are especially critical for agents, such as nucleic acids, that can be degraded or inactivated in the extracellular environment. The degradation of nucleic acids in the HBV vaccine can lead to a reduction in efficacy and consistency in the application of the therapy. Also, the inter-subject rate of degradation of nucleic acids in the HBV vaccine is not constant, thus contributing to the overall therapeutic inconsistency of conventional needle-syringe injection combined with ESA, and more specifically with electroporation therapy.

Due to the inherent difficulty of spatial and temporal variability with conventional needle-syringe injection used in conjunction with ESA, the precise location and timing of TAA relative to ESA is often unknown. As a result, the effective administration and dosing of HBV vaccines with EMTAD can be inconsistent and irreproducible. Though conventional needle-syringe injection is sometimes adequate for HBV vaccine administration, reproducible and consistent delivery of HBV vaccines is significantly enhanced by controlling the spatial and temporal relationship between administration of the HBV vaccine and induction of the desired EMTAD effect.

Thus, while the traditional EMTAD procedure can be adequate for certain applications, temporal and spatial control is highly desirable for clinical applications that typically require a high degree of consistency and reproducibility. In contrast to the conventional EMTAD approach, embodiments of methods, systems and apparatus described herein facilitate CTAA and ESA to provide more advantageous methods and apparatus for the clinical application of EMTAD. The disclosure utilizes various aspects of CTAA in conjunction with ESA to provide reproducible, consistent, and efficacious HBV vaccine delivery. The disclosure describes methods and apparatus to provide spatial and temporal control over administration of an HBV vaccine relative to the application of electrical signals, thereby improving the movement and/or uptake of said vaccine in the target tissue.

In some embodiments are provided methods and apparatus wherein there exists a controllable spatial relationship for the administration of the HBV vaccine relative to the application of electrical signals. Prior to treatment, the optimal location for TAA relative to ESA is determined. This spatial relationship between TAA and ESA is dictated by treatment parameters, including the nature of the agent being administered and the properties of the target tissue to which the agent is administered. In an exemplary embodiment, electrical signals are preferentially applied distal to the site of HBV vaccine administration. In certain other embodiments, spatial relationship is to apply the EMTAD-inducing electrical signals proximal to the site of agent administration. In certain cases, co-localization between TAA and ESA is preferable. This is often the case when electroporation and/or iontophoresis are utilized for induction of the desired EMTAD effect.

In another aspect of the disclosure, an apparatus described herein provides a controllable temporal relationship for the sequence and timing of TAA relative to ESA. Prior to treatment, the optimal sequence and timing for a combination of TAA and ESA is determined. As with the spatial relationship, the desired temporal relationship between TAA and ESA is dictated by parameters such as the nature of the agent being administered and the properties of the target tissue to which the agent is administered. In certain applications, exposure to the electrical fields associated with ESA may adversely affect the HBV vaccine. In the practice of such applications, generation of such electrical fields is followed by CTAA. However, the typical temporal relationship is CTAA followed by ESA.

The disclosure provides improved methods and apparatus for the reproducible, consistent, and efficacious delivery of HBV vaccines comprising nucleic acid based constructs with EMTAD. This objective is accomplished by controlling the spatial and temporal administration of an HBV vaccine relative to application of electrical signals. In a certain embodiment, EMTAD is initiated by HBV vaccine injection using a conventional needle-syringe. After the agent has been administered, a device suitable for ESA is applied to the subject at a designated location. An appropriate ESA protocol is utilized to provide the desired facilitation or enhancement to HBV vaccine delivery. An exemplary ESA method that has proven to be effective in virtually all cell types is electroporation. Other exemplary methods of electrically mediated delivery include, but are not limited to, iontophoresis, electroosmosis, electropermeabilization, electrostimulation, electromigration, and electroconvection.

These terms are used for illustrative purposes only and should not be construed as limitations in the disclosure.

The technique of electroporation utilizes the application of electric fields to induce a transient increase in cell membrane permeability and to move charged particles. By permeabilizing the cell membranes within the target tissue, electroporation dramatically improves the intracellular uptake of exogenous substances that have been administered to the target tissue. The increase in cell membrane permeability and molecular movement due to electroporation offers a method for overcoming the cell membrane as a barrier to HBV vaccine delivery. The application of electroporation as a technique for inducing EMTAD is advantageous in that the physical nature of the technique allows electroporation to be applied in virtually all tissue types. Accordingly, various aspects and embodiments of the disclosure discuss, but are not limited to, electroporation as a technique for inducing EMTAD.

HBV Vaccines

The term "HBV vaccine" is used herein in its broadest sense to include any agent capable of providing a desired or beneficial immune response, therapeutic and/or prophylactic effect against an HBV on a living tissue. Thus, the term includes both prophylactic and therapeutic HBV vaccines, as well as any other category of agent having such desired effects. The scope of the disclosure is sufficiently broad to include the controlled delivery of any HBV vaccines, however categorized. HBV vaccines include, but are not limited to pharmaceutical drugs and vaccines, and nucleic acid sequences (such as supercoiled, relaxed, and linear plasmid DNA, RNA, antisense constructs, artificial chromosomes, or any other nucleic acid-based therapeutic), and any formulations thereof. Such agent formulations include, but are not limited to, cationic lipids, cationic and/or nonionic polymers, liposomes, saline, nuclease inhibitors, anesthetics, poloxamers, preservatives, sodium phosphate solutions, or other compounds that can improve the administration, stability, and/or effect of the HBV vaccine. Additional formulations include agents and additives conferring the ability to control viscosity and electrical impedance of the administered agent.

In a preferred aspect of the application, an HBV vaccine to be used in the invention can comprise:

a first nucleic acid molecule, preferably a first plasmid DNA vector, comprising a first polynucleotide encoding an HBV polymerase antigen, preferably the HBV polymerase antigen has an amino acid sequence that is at least 98% identical to SEQ ID NO: 4, such as at least 98%, 98.5%, 99%, 99.1%, 99.2%, 99.3%, 99.4%, 99.5%, 99.6%, 99.7%, 99.8%, 99.9% or 100% identical to SEQ ID NO: 4, wherein the HBV polymerase antigen does not have reverse transcriptase activity and RNase H activity;

a second nucleic acid molecule, preferably a second plasmid DNA vector, comprising a second polynucleotide encoding a truncated HBV core antigen, preferably the truncated HBV core antigen consists of the amino acid sequence of SEQ ID NO: 2 or SEQ ID NO: 14; and a pharmaceutically acceptable carrier, and wherein the first nucleic acid molecule and the second nucleic acid molecule are present in the same nucleic acid molecule, such as the same plasmid DNA vector, or in two different nucleic acid molecules, such as two separate plasmid DNA vectors.

As used herein, each of the terms "HBV core antigen," "HBcAg" and "core antigen" refers to an HBV antigen capable of inducing an immune response, e.g., a humoral and/or cellular mediated response, against an HBV core protein in a subject. Each of the terms "core," "core polypeptide," and "core protein" refers to the HBV viral core protein. Full-length core antigen is typically 183 amino acids in length and includes an assembly domain (amino acids 1 to 149) and a nucleic acid binding domain (amino acids 150 to 183). The 34-residue nucleic acid binding domain is required for pre-genomic RNA encapsidation. This domain also functions as a nuclear import signal. It comprises 17 arginine residues and is highly basic, consistent with its function. HBV core protein is dimeric in solution, with the dimers self-assembling into icosahedral capsids. Each dimer of core protein has four α-helix bundles flanked by an α-helix domain on either side. Truncated HBV core proteins lacking the nucleic acid binding domain are also capable of forming capsids.

In an aspect of the application, an HBV antigen to be used in the invention is a truncated HBV core antigen. As used herein, a "truncated HBV core antigen," refers to an HBV antigen that does not contain the entire length of an HBV core protein but is capable of inducing an immune response against the HBV core protein in a subject. For example, an HBV core antigen can be modified to delete one or more amino acids of the highly positively charged (arginine rich) C-terminal nucleic acid binding domain of the core antigen, which typically contains seventeen arginine (R) residues. A truncated HBV core antigen of the application is preferably a C-terminally truncated HBV core protein which does not comprise the HBV core nuclear import signal and/or a truncated HBV core protein from which the C-terminal HBV core nuclear import signal has been deleted. In an embodiment, a truncated HBV core antigen comprises a deletion in the C-terminal nucleic acid binding domain, such as a deletion of 1 to 34 amino acid residues of the C-terminal nucleic acid binding domain, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34 amino acid residues, preferably a deletion of all 34 amino acid residues. In a preferred embodiment, a truncated HBV core antigen comprises a deletion in the C-terminal nucleic acid binding domain, preferably of all 34 amino acid residues.

An HBV core antigen useful in the application can be a consensus sequence derived from multiple HBV genotypes (e.g., genotypes A, B, C, D, E, F, G, and H). As used herein, "consensus sequence" means an artificial sequence of amino acids based on an alignment of amino acid sequences of homologous proteins, e.g., as determined by an alignment (e.g., using Clustal Omega) of amino acid sequences of homologous proteins. It can be the calculated order of most frequent amino acid residues, found at each position in a sequence alignment, based upon sequences of HBV antigens (e.g., core, pol, etc.) from at least 100 natural HBV isolates. A consensus sequence can be non-naturally occurring and different from the native viral sequences. Consensus sequences can be designed by aligning multiple HBV antigen sequences from different sources using a multiple sequence alignment tool, and at variable alignment positions, selecting the most frequent amino acid. Preferably, a consensus sequence of an HBV antigen is derived from HBV genotypes B, C, and D. The term "consensus antigen" is used to refer to an antigen having a consensus sequence.

An exemplary truncated HBV core antigen useful for the application lacks the nucleic acid binding function, and can be capable of inducing an immune response in a mammal against at least two HBV genotypes. Preferably a truncated HBV core antigen is capable of inducing a T cell response in a mammal against at least HBV genotypes B, C and D. More preferably, a truncated HBV core antigen is capable of inducing a CD8 T cell response in a human subject against at least HBV genotypes A, B, C and D.

Preferably, an HBV core antigen useful for the application is a consensus antigen, preferably a consensus antigen derived from HBV genotypes B, C, and D, more preferably a truncated consensus antigen derived from HBV genotypes B, C, and D. An exemplary truncated HBV core consensus antigen according to the application consists of an amino acid sequence that is at least 90% identical to SEQ ID NO: 2 or SEQ ID NO: 14, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9%, or 100% identical to SEQ ID NO: 2 or SEQ ID NO: 14. SEQ ID NO: 2 and SEQ ID NO: 4 are core consensus antigens derived from HBV genotypes B, C, and D. SEQ ID NO: 2 and SEQ ID NO:14 contain a 34-amino acid C-terminal deletion of the highly positively charged (arginine rich) nucleic acid binding domain of the native core antigen.

In a particular embodiment of the application, an HBV core antigen is a truncated HBV antigen consisting of the amino acid sequence of SEQ ID NO: 2. In another particular embodiment, an HBV core antigen is a truncated HBV antigen consisting of the amino acid sequence of SEQ ID NO: 14.

Examples of polynucleotide sequences encoding a truncated HBV core antigen consisting of the amino acid sequence of SEQ ID NO: 2 include, but are not limited to, a polynucleotide sequence at least 90% identical to SEQ ID NO: 1, such as or at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.1%, at least 99.2%, at least 99.3%, at least 99.4%, at least 99.5%, at least 99.6%, at least 99.7%, at least 99.8%, at least 99.9% or 100% identical to SEQ ID NO: 1, preferably about 98%, about 99% or 100% identical to SEQ ID NO: 1.

Examples of polynucleotide sequences encoding a truncated HBV core antigen consisting of the amino acid sequence of SEQ ID NO: 14 include, but are not limited to, a polynucleotide sequence at least 90% identical to SEQ ID NO: 15, such as or at least 90%, at least 91%, at least 92%, at least 93%, at least 94%, at least 95%, at least 95.5%, at least 96%, at least 96.5%, at least 97%, at least 97.5%, at least 98%, at least 98.5%, at least 99%, at least 99.1%, at least 99.2%, at least 99.3%, at least 99.4%, at least 99.5%, at least 99.6%, at least 99.7%, at least 99.8%, at least 99.9% or 100% identical to SEQ ID NO: 15, preferably about 98%, about 99% or 100% identical to SEQ ID NO: 15.

In particular embodiments of the application, a HBV vaccine to be used in the invention comprises a non-naturally occurring nucleic acid molecule encoding a truncated HBV core antigen, and the non-naturally occurring nucleic acid molecule comprises the polynucleotide sequence of SEQ ID NO: 1 or SEQ ID NO: 15.

As used herein, the term "HBV polymerase antigen," "HBV Pol antigen" or "HBV pol antigen" refers to an HBV antigen capable of inducing an immune response, e.g., a humoral and/or cellular mediated response, against an HBV polymerase in a subject. Each of the terms "polymerase," "polymerase polypeptide," "Pol" and "pol" refers to the HBV viral DNA polymerase. The HBV viral DNA polymerase has four domains, including, from the N terminus to the C terminus, a terminal protein (TP) domain, which acts as a primer for minus-strand DNA synthesis; a spacer that is nonessential for the polymerase functions; a reverse transcriptase (RT) domain for transcription; and a RNase H domain.

In an embodiment of the application, an HBV antigen comprises an HBV Pol antigen, or any immunogenic fragment or combination thereof. An HBV Pol antigen can contain further modifications to improve immunogenicity of the antigen, such as by introducing mutations into the active sites of the polymerase and/or RNase H domains to decrease or substantially eliminate certain enzymatic activities.

Preferably, an HBV Pol antigen useful in the application does not have reverse transcriptase activity and RNase H activity, and is capable of inducing an immune response in a mammal against at least two HBV genotypes. Preferably, an HBV Pol antigen is capable of inducing a T cell response in a mammal against at least HBV genotypes B, C and D. More preferably, a HBV Pol antigen is capable of inducing a CD8 T cell response in a human subject against at least HBV genotypes A, B, C and D.

Thus, in some embodiments, an HBV Pol antigen useful in the application is an inactivated Pol antigen. In an embodiment, an inactivated HBV Pol antigen comprises one or more amino acid mutations in the active site of the polymerase domain. In another embodiment, an inactivated HBV Pol antigen comprises one or more amino acid mutations in the active site of the RNaseH domain. In a preferred embodiment, an inactivated HBV pol antigen comprises one or more amino acid mutations in the active site of both the polymerase domain and the RNaseH domain. For example, the "YXDD" motif in the polymerase domain of an HBV pol antigen that can be required for nucleotide/metal ion binding can be mutated, e.g., by replacing one or more of the aspartate residues (D) with asparagine residues (N), eliminating or reducing metal coordination function, thereby decreasing or substantially eliminating reverse transcriptase function. Alternatively, or in addition to mutation of the "YXDD" motif, the "DEDD" motif in the RNaseH domain of an HBV pol antigen required for $Mg^{2+}$ coordination can be mutated, e.g., by replacing one or more aspartate residues (D) with asparagine residues (N) and/or replacing the glutamate residue (E) with glutamine (Q), thereby decreasing or substantially eliminating RNaseH function. In a particular embodiment, an HBV pol antigen is modified by (1) mutating the aspartate residues (D) to asparagine residues (N) in the "YXDD" motif of the polymerase domain; and (2) mutating the first aspartate residue (D) to an asparagine residue (N) and the first glutamate residue (E) to a glutamine residue (N) in the "DEDD" motif of the RNaseH domain, thereby decreasing or substantially eliminating both the reverse transcriptase and RNaseH functions of the pol antigen.

In a preferred embodiment of the application, an HBV pol antigen is a consensus antigen, preferably a consensus antigen derived from HBV genotypes B, C, and D, more preferably an inactivated consensus antigen derived from HBV genotypes B, C, and D. An exemplary HBV pol consensus antigen according to the application comprises an amino acid sequence that is at least 90% identical to SEQ ID NO: 4, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 4, preferably at least 98% identical to SEQ ID NO: 4, such as at least 98%, 98.5%, 99%, 99.1%, 99.2%, 99.3%, 99.4%, 99.5%, 99.6%, 99.7%, 99.8%, 99.9% or 100% identical to SEQ ID NO: 4. SEQ ID NO: 4 is a pol consensus antigen derived from HBV genotypes B, C, and D comprising four mutations located in the active sites of the polymerase and RNaseH domains. In particular, the four mutations include mutation of the aspartic acid residues (D) to asparagine residues (N) in the "YXDD" motif of the polymerase domain; and mutation of the first aspartate residue (D) to an asparagine residue (N) and mutation of the glutamate residue (E) to a glutamine residue (Q) in the "DEDD" motif of the RNaseH domain.

In a particular embodiment of the application, an HBV pol antigen useful for the application comprises the amino acid sequence of SEQ ID NO: 4. In other embodiments of the application, an HBV core antigen useful in the application consists of the amino acid sequence of SEQ ID NO: 4.

Examples of polynucleotide sequences encoding a HBV pol antigen comprising the amino acid sequence of SEQ ID NO: 4 include, but are not limited to, a polynucleotide sequence at least 90% identical to SEQ ID NO: 3 or SEQ ID NO: 16, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 3 or SEQ ID NO: 16, preferably 98%, 99% or 100% identical to SEQ ID NO: 3 or SEQ ID NO: 16. In particular embodiments of the application, a HBV vaccine useful for the application comprises a non-naturally occurring nucleic acid molecule encoding a HBV pol antigen, and the non-naturally occurring nucleic acid molecule comprises the polynucleotide sequence of SEQ ID NO: 3 or SEQ ID NO: 16.

As used herein the term "fusion protein" or "fusion" refers to a single polypeptide chain having at least two polypeptide domains that are not normally present in a single, natural polypeptide.

In an aspect of the application, an HBV antigen to be used in the invention can comprise a fusion protein comprising a truncated HBV core antigen operably linked to an HBV Pol antigen, or an HBV Pol antigen operably linked to a truncated HBV core antigen, preferably via a linker. As used herein, the term "linker" refers to a compound or moiety that acts as a molecular bridge to operably link two different molecules, wherein one portion of the linker is operably linked to a first molecule, and wherein another portion of the linker is operably linked to a second molecule. As used herein, the term "operably linked" refers to a linkage or a juxtaposition wherein the components so described are in a relationship permitting them to function in their intended manner. For example, a regulatory sequence operably linked to a nucleic acid sequence of interest is capable of directing the transcription of the nucleic acid sequence of interest, or a signal sequence operably linked to an amino acid sequence of interest is capable of secret or translocate the amino acid sequence of interest over a member.

For example, in a fusion protein containing a first polypeptide and a second heterologous polypeptide, a linker serves primarily as a spacer between the first and second polypeptides. In an embodiment, a linker is made up of amino acids linked together by peptide bonds, preferably from 1 to 20 amino acids linked by peptide bonds, wherein the amino acids are selected from the 20 naturally occurring amino acids. In an embodiment, the 1 to 20 amino acids are selected from glycine, alanine, proline, asparagine, glutamine, and lysine. Preferably, a linker is made up of a majority of amino acids that are sterically unhindered, such as glycine and alanine. Exemplary linkers are polyglycines, particularly (Gly)5, (Gly)8; poly(Gly-Ala), and polyalanines. One exemplary suitable linker is (AlaGly)n, wherein n is an integer of 2 to 5.

Preferably, a fusion protein useful in the application is capable of inducing an immune response in a mammal against HBV core and HBV Pol of at least two HBV genotypes. Preferably the fusion protein is capable of inducing a T cell response in a mammal against at least HBV genotypes B, C and D. More preferably, the fusion protein is capable of inducing a CD8 T cell response in a human subject against at least HBV genotypes A, B, C and D.

In an aspect of the application, a fusion protein useful in the application can comprise a truncated HBV core antigen having an amino acid sequence at least 90%, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9%, or 100% identical to SEQ ID NO: 2 or 14, a linker, and a HBV Pol antigen having an amino acid sequence at least 90%, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9%, or 100%, identical to SEQ ID NO: 4.

Preferably, a fusion protein useful in the application comprises a truncated HBV core antigen consisting of the amino acid sequence of SEQ ID NO: 2 or 14, a linker comprising (AlaGly)n, wherein n is an integer of 2 to 5, and a HBV Pol antigen having the amino acid sequence of SEQ ID NO: 4. More preferably, a fusion protein useful in the application comprises the amino acid sequence of SEQ ID NO: 20.

In some embodiments of the application, a fusion protein useful in the application further comprises a signal sequence. Preferably, the signal sequence has the amino acid sequence of SEQ ID NO: 6 or SEQ ID NO: 19. More preferably, the fusion protein comprises the amino acid sequence of SEQ ID NO: 21.

Examples of polynucleotide sequences encoding a fusion protein useful in the application include, but are not limited to, a polynucleotide sequence at least 90% identical to SEQ ID NO: 1 or SEQ ID NO: 15, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 1 or SEQ ID NO: 15, preferably 98%, 99% or 100% identical to SEQ ID NO: 1 or SEQ ID NO: 15, operably linked to a linker coding sequence at least 90% identical to SEQ ID NO: 22, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 22, preferably 98%, 99% or 100% identical to SEQ ID NO: 22, which is further operably linked a polynucleotide sequence at least 90% identical to SEQ ID NO: 3 or SEQ ID NO: 16, such as at least 90%, 91%, 92%, 93%, 94%, 95%, 95.5%, 96%, 96.5%, 97%, 97.5%, 98%, 98.5%, 99%, 99.1%, 99.2%, 99.3%, 99.4%, 99.5%, 99.6%, 99.7%, 99.8%, 99.9% or 100% identical to SEQ ID NO: 3 or SEQ ID NO: 16, preferably 98%, 99% or 100% identical to SEQ ID NO: 3 or SEQ ID NO: 16. In particular embodiments of the application, a HBV vaccine useful in the application comprises a non-naturally occurring nucleic acid molecule encoding a fusion protein, and the non-naturally occurring nucleic acid molecule comprises SEQ ID NO: 1, operably linked to SEQ ID NO: 22, which is further operably linked to SEQ ID NO: 3.

In an aspect of the application, in an HBV vaccine to be used in the application, the first and second nucleic acid molecules are first and second plasmid DNA vectors, respectively, and each of the first and second plasmid DNA vectors comprises an origin of replication, an antibiotic resistance gene, and from 5' end to 3' end, a promoter sequence, an enhancer sequence, a signal peptide coding sequence, the first polynucleotide sequence or the second polynucleotide sequence, and a polyadenylation signal sequence. In a preferred embodiment of the application, a DNA plasmid is an expression vector suitable for protein expression in mammalian host cells. Expression vectors suitable for protein expression in mammalian host cells include, but are not limited to, pcDNA™, pcDNA3™, pVAX, pVAX-1, etc. Preferably, the expression vector is based on pVAX-1, which can be further modified to optimize protein expression in mammalian cells. pVAX-1 is a commonly used plasmid in DNA vaccines, and contains a strong human intermediate early cytomegalovirus (CMV-IE) promoter followed by the bovine growth hormone (bGH)-derived polyadenylation sequence (pA). pVAX-1 further contains a pUC origin of replication and a kanamycin resistance gene driven by a small prokaryotic promoter that allows for bacterial plasmid propagation. Preferably, the plasmid DNA vector comprises a codon optimized kanamycin resistance gene having a polynucleotide sequence at least 90% identical to SEQ ID NO: 12, preferably 100% identical to SEQ ID NO: 12.

In a specific embodiment, an HBV vaccine to be used in the invention comprises:

a) a first plasmid DNA vector comprising, from 3'-end to 5'-end, the promoter sequence comprising the polynucleotide sequence of SEQ ID NO: 7, the enhancer sequence comprising the polynucleotide sequence of SEQ ID NO: 8, the signal peptide coding sequence comprising the polynucleotide sequence of SEQ ID NO: 5, the first polynucleotide sequence comprising the polynucleotide sequence of SEQ ID NO: 3, and the polyadenylation signal sequence comprising the polynucleotide sequence of SEQ ID NO: 11;

b) a second plasmid DNA vector comprising, from 3'-end to 5'-end, the promoter sequence comprising the polynucleotide sequence of SEQ ID NO: 7, the enhancer sequence comprising the polynucleotide sequence of SEQ ID NO: 8, the signal peptide coding sequence comprising the polynucleotide sequence of SEQ ID NO: 5, the second polynucleotide sequence comprising the polynucleotide sequence of SEQ ID NO: 1, and the polyadenylation signal sequence comprising the polynucleotide sequence of SEQ ID NO: 11; and c) a pharmaceutically acceptable carrier, wherein each of the first plasmid DNA vector and the second plasmid DNA vector further comprises a kanamycin resistance gene having the polynucleotide sequence of SEQ ID NO: 12, and an original of replication having the polynucleotide sequence of SEQ ID NO: 10, and wherein the first plasmid DNA vector and the second plasmid DNA vector are in the same composition or two different compositions.

In those embodiments of the application in which an HBV vaccine comprises a first vector, such as a first DNA plasmid, and a second vector, such as a second DNA plasmid, the amount of each of the first and second vectors is not particularly limited. For example, the first DNA plasmid and the second DNA plasmid can be present in a ratio of 10:1 to 1:10, by weight, such as 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10, by weight. Preferably, the first and second DNA plasmids are present in a ratio of 1:1, by weight.

Compositions and immunogenic combinations of the application can comprise additional polynucleotides or vectors encoding additional HBV antigens and/or additional HBV antigens or immunogenic fragments thereof. However, in particular embodiments, the compositions and immunogenic combinations of the application do not comprise certain antigens. In preferred embodiments, an HBV vaccine to be used in the invention does not contain a nucleic acid molecule encoding an HBV antigen selected from the group consisting of a Hepatitis B surface antigen (HBsAg), an HBV envelope (Env) antigen, and an HBV L protein antigen, nor an HBV antigen selected from the group consisting of a Hepatitis B surface antigen (HBsAg), an HBV envelope (Env) antigen, and an HBV L protein antigen.

An HBV vaccine useful in the application can also comprise a pharmaceutically acceptable carrier. A pharmaceutically acceptable carrier is non-toxic and should not interfere with the efficacy of the active ingredient. Pharmaceutically acceptable carriers can include one or more, such as water, glycols, sugar, oils, amino acids, alcohols, preservatives, emollients, stabilizers, coloring agents and the like.

Other examples of HBV vaccines useful in the application are described in International Patent Application entitled "Hepatitis B Virus (HBV) Vaccines and Uses thereof" filed on the same day as this application with the contents of which are hereby incorporated by reference in their entireties.

Kits/Systems

In a general aspect, the invention relates to a kit or system for the controlled delivery of a HBV vaccine to a predetermined tissue site within a subject in need thereof, comprising the HBV vaccine and an apparatus for administering the HBV vaccine to the predetermined tissue site via electroporation. For example, the kit or system can have a prepacked container, such as a syringe, containing a premeasured amount of the HBV vaccine, which can be loaded to an apparatus described here for the subsequent administration of the HBV vaccine.

Methods of Inducing an Immune Response

In another general aspect, the invention relates to a method of inducing an immune response against hepatitis B virus (HBV) in a subject in need thereof, comprising administering to the subject an immunogenically effective amount of an HBV vaccine using an apparatus, kit or system of the application. Any of the apparatus, kit or system of the application described herein can be used in the methods of the application. As used herein, the term "infection" refers to the invasion of a host by a disease causing agent. A disease causing agent is considered to be "infectious" when it is capable of invading a host, and replicating or propagating within the host. Examples of infectious agents include viruses, e.g., HBV and certain species of adenovirus, prions, bacteria, fungi, protozoa and the like. "HBV infection" specifically refers to invasion of a host organism, such as cells and tissues of the host organism, by HBV.

As used herein, "inducing an immune response" when used with reference to the methods described herein encompasses causing a desired immune response or effect in a subject in need thereof against an infection, e.g. HBV infection. "Inducing an immune response" also encompasses providing a therapeutic immunity for treating against a pathogenic agent, e.g., HBV. As used herein, the term "therapeutic immunity" or "therapeutic immune response" means that the vaccinated subject is able to control an infection with the pathogenic agent against which the vaccination was done, for instance immunity against HBV infection conferred by vaccination with HBV vaccine. In an embodiment, "inducing an immune response" means producing an immunity in a subject in need thereof, e.g., to provide a therapeutic effect against a disease, such as HBV infection. In certain embodiments, "inducing an immune response" refers to causing or improving cellular immunity, e.g., T cell response, against HBV. In certain embodiments, "inducing an immune response" refers to causing or improving a humoral immune response against HBV. In certain embodiments, "inducing an immune response" refers to causing or improving a cellular and a humoral immune response against HBV.

As used herein, the term "protective immunity" or "protective immune response" means that the vaccinated subject is able to control an infection with the pathogenic agent against which the vaccination was done. Usually, the subject having developed a "protective immune response" develops only mild to moderate clinical symptoms or no symptoms at all. Usually, a subject having a "protective immune response" or "protective immunity" against a certain agent will not die as a result of the infection with said agent.

Typically, the administration of an HBV vaccine according to embodiments of the application will have a therapeutic aim to generate an immune response against HBV after HBV infection or development of symptoms characteristic of HIV infection, e.g., for therapeutic vaccination.

As used herein, "an immunogenically effective amount" or "immunologically effective amount" means an amount of a composition, polynucleotide, vector, or antigen sufficient to induce a desired immune effect or immune response in a subject in need thereof. In an embodiment, an immunogenically effective amount means an amount sufficient to induce an immune response in a subject in need thereof. In another embodiment, an immunogenically effective amount means an amount sufficient to produce immunity in a subject in need thereof, e.g., provide a therapeutic effect against a disease such as HBV infection. An immunogenically effective amount can vary depending upon a variety of factors, such as the physical condition of the subject, age, weight, health, etc.; the particular application, e.g., providing protective immunity or therapeutic immunity; and the particular disease, e.g., viral infection, for which immunity is desired. An immunogenically effective amount can readily be determined by one of ordinary skill in the art in view of the disclosure.

In particular embodiments of the application, an immunogenically effective amount refers to the amount of a composition or immunogenic combination (such as an HBV vaccine) which is sufficient to achieve one, two, three, four, or more of the following effects: (i) reduce or ameliorate the severity of an HBV infection or a symptom associated therewith; (ii) reduce the duration of an HBV infection or symptom associated therewith; (iii) prevent the progression of an HBV infection or symptom associated therewith; (iv) cause regression of an HBV infection or symptom associated therewith; (v) prevent the development or onset of an HBV infection, or symptom associated therewith; (vi) prevent the recurrence of an HBV infection or symptom associated therewith; (vii) reduce hospitalization of a subject having an HBV infection; (viii) reduce hospitalization length of a subject having an HBV infection; (ix) increase the survival of a subject with an HBV infection; (x) eliminate an HBV infection in a subject; (xi) inhibit or reduce HBV replication in a subject; and/or (xii) enhance or improve the prophylactic or therapeutic effect(s) of another therapy.

In other particular embodiments, an immunogenically effective amount is an amount sufficient to reduce HBsAg levels consistent with evolution to clinical seroconversion; achieve sustained HBsAg clearance associated with reduction of infected hepatocytes by a subject's immune system; induce HBV-antigen specific activated T-cell populations; and/or achieve persistent loss of HBsAg within 12 months. Examples of a target index include lower HBsAg below a threshold of 500 copies of HBsAg International Unit (IU) and/or higher CD8 counts.

As general guidance, an immunogenically effective amount when used with reference to a DNA plasmid can range from about 0.1 mg/mL to 10 mg/mL of DNA plasmid total, such as 0.1 mg/mL, 0.25 mg/mL, 0.5 mg/mL. 0.75 mg/mL 1 mg/mL, 1.5 mg/mL, 2 mg/mL, 3 mg/mL, 4 mg/mL, 5 mg/mL, 6 mg/mL, 7 mg/mL, 8 mg/mL, 9 mg/mL, or 10 mg/mL. Preferably, an immunogenically effective amount of DNA plasmid is less than 8 mg/mL, more preferably less than 6 mg/mL, even more preferably 3-4 mg/mL. An immunogenically effective amount can be from one vector or plasmid, or from multiple vectors or plasmids. An immunogenically effective amount can be administered in a single composition, or in multiple compositions, such as 1, 2, 3, 4, 5, 6, 7, 8, 9, or 10 compositions (e.g., tablets, capsules or injectables), wherein the administration of the multiple capsules or injections collectively provides a subject with an immunogenically effective amount. It is also possible to administer an immunogenically effective amount to a subject, and subsequently administer another dose of an immunogenically effective amount to the same subject, in a so-called prime-boost regimen. This general concept of a prime-boost regimen is well known to the skilled person in the vaccine field. Further booster administrations can optionally be added to the regimen, as needed.

According to embodiments of the application, an immunogenic combination comprising two DNA plasmids, e.g., a first DNA plasmid encoding an HBV core antigen and a second DNA plasmid encoding an HBV pol antigen can be administered to a subject by mixing both plasmids and delivering the mixture to a single anatomic site. Alternatively, two separate immunizations each delivering a single expression plasmid can be performed. In such embodiments, whether both plasmids are administered in a single immunization as a mixture or in two separate immunizations, the first DNA plasmid and the second DNA plasmid can be administered in a ratio of 10:1 to 1:10, by weight, such as 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, or 1:10, by weight. Preferably, the first and second DNA plasmids are administered in a ratio of 1:1, by weight.

In some embodiments, a subject to be treated according to the methods of the application is an HBV-infected subject, particular a subject having chronic HBV infection. Acute HBV infection is characterized by an efficient activation of the innate immune system complemented with a subsequent broad adaptive response (e.g., HBV-specific T-cells, neutralizing antibodies), which usually results in successful suppression of replication or removal of infected hepatocytes. In contrast, such responses are impaired or diminished due to high viral and antigen load, e.g., HBV envelope proteins are produced in abundance and can be released in sub-viral particles in 1,000-fold excess to infectious virus.

Chronic HBV infection is described in phases characterized by viral load, liver enzyme levels (necroinflammatory activity), HBeAg, or HBsAg load or presence of antibodies to these antigens. cccDNA levels stay relatively constant at approximately 10 to 50 copies per cell, even though viremia can vary considerably. The persistence of the cccDNA species leads to chronicity. More specifically, the phases of chronic HBV infection include: (i) the immune-tolerant phase characterized by high viral load and normal or minimally elevated liver enzymes; (ii) the immune activation HBeAg-positive phase in which lower or declining levels of viral replication with significantly elevated liver enzymes are observed; (iii) the inactive HBsAg carrier phase, which is a low replicative state with low viral loads and normal liver enzyme levels in the serum that may follow HBeAg seroconversion; and (iv) the HBeAg-negative phase in which viral replication occurs periodically (reactivation) with concomitant fluctuations in liver enzyme levels, mutations in the pre-core and/or basal core promoter are common, such that HBeAg is not produced by the infected cell.

As used herein, "chronic HBV infection" refers to a subject having the detectable presence of HBV for more than 6 months. A subject having a chronic HBV infection can be in any phase of chronic HBV infection. Chronic HBV infection is understood in accordance with its ordinary meaning in the field. Chronic HBV infection can for example be characterized by the persistence of HBsAg for 6 months or more after acute HBV infection. For example, a chronic HBV infection referred to herein follows the definition published by the Centers for Disease Control and Prevention (CDC), according to which a chronic HBV infection can be characterized by laboratory criteria such as: (i) negative for IgM antibodies to hepatitis B core antigen (IgM anti-HBc) and positive for hepatitis B surface antigen (HBsAg), hepatitis B e antigen (HBeAg), or nucleic acid test for hepatitis B virus DNA, or (ii) positive for HBsAg or nucleic acid test for HBV DNA, or positive for HBeAg two times at least 6 months apart.

According to particular embodiments, an immunogenically effective amount refers to the amount of a composition or immunogenic combination which is sufficient to treat chronic HBV infection.

In some embodiments, a subject having chronic HBV infection is undergoing nucleoside analog (NUC) treatment, and is NUC-suppressed. As used herein, "NUC-suppressed" refers to a subject having an undetectable viral level of HBV and stable alanine aminotransferase (ALT) levels for at least six months. Examples of nucleoside/nucleotide analog treatment include HBV polymerase inhibitors, such as entacavir and tenofovir. Preferably, a subject having chronic HBV infection does not have advanced hepatic fibrosis or cirrhosis. Such subject would typically have a METAVIR score of less than 3 for fibrosis and a fibroscan result of less than 9 kPa. The METAVIR score is a scoring system that is commonly used to assess the extent of inflammation and fibrosis by histopathological evaluation in a liver biopsy of patients with hepatitis B. The scoring system assigns two standardized numbers: one reflecting the degree of inflammation and one reflecting the degree of fibrosis.

It is believed that elimination or reduction of chronic HBV may allow early disease interception of severe liver disease, including virus-induced cirrhosis and hepatocellular carcinoma. Thus, the methods of the application can also be used as therapy to treat HBV-induced diseases. Examples of HBV-induced diseases include, but are not limited to cirrhosis, cancer (e.g., hepatocellular carcinoma), and fibrosis, particularly advanced fibrosis characterized by a METAVIR score of 3 or higher for fibrosis. In such embodiments, an immunogenically effective amount is an amount sufficient to achieve persistent loss of HBsAg within 12 months and significant decrease in clinical disease (e.g., cirrhosis, hepatocellular carcinoma, etc.).

Methods according to embodiments of the application further comprise administering to the subject in need thereof another immunogenic agent (such as another HBV antigen or other antigen) or another anti-HBV agent (such as a nucleoside analog or other anti-HBV agent) in combination with a composition of the application.

The ability to induce or stimulate an anti-HBV immune response upon administration in an animal or human organism can be evaluated either in vitro or in vivo using a variety of assays which are standard in the art. For a general description of techniques available to evaluate the onset and activation of an immune response, see for example Coligan et al. (1992 and 1994, Current Protocols in Immunology; ed. J Wiley & Sons Inc., National Institute of Health). Measurement of cellular immunity can be performed by measurement of cytokine profiles secreted by activated effector cells including those derived from CD4+ and CD8+ T-cells (e.g. quantification of IL-10 or IFN gamma-producing cells by ELISPOT), by determination of the activation status of immune effector cells (e.g. T cell proliferation assays by a classical [3H] thymidine uptake), by assaying for antigen-specific T lymphocytes in a sensitized subject (e.g. peptide-specific lysis in a cytotoxicity assay, etc.).

The ability to stimulate a cellular and/or a humoral response can be determined by antibody binding and/or competition in binding (see for example Harlow, 1989, Antibodies, Cold Spring Harbor Press). For example, titers of antibodies produced in response to administration of a composition providing an immunogen can be measured by enzyme-linked immunosorbent assay (ELISA). The immune responses can also be measured by neutralizing antibody assay, where a neutralization of a virus is defined as the loss of infectivity through reaction/inhibition/neutralization of the virus with specific antibody. The immune response can further be measured by Antibody-Dependent Cellular Phagocytosis (ADCP) Assay.

Target Tissues

Target tissues well suited for EMTAD by use of methods, apparatus and systems described herein include both healthy and diseased cells located in, for instance, the epidermis, dermis, hypodermis, connective, and muscle tissue. The technique can also be utilized for application in healthy or diseased organs that must be accessed via minimally invasive or other surgical methods. Such target tissues include the liver, lungs, heart, blood vessels, lymphatic, brain, kidneys, pancreas, stomach, intestines, colon, bladder, and reproductive organs. In some embodiments, a desired therapeutic effect can be derived by use of a method, or apparatus described herein to deliver an amount of agent to cell types normally located within the target tissues as well as other cell types abnormally found within said tissues (e.g. chemotherapeutic treatment of tumors).

As discussed previously, and depicted in FIG. 1, traditional EMTAD suffers from a lack of precision and reproducibility in the spatial and temporal relationship between the administration of the HBV vaccine and the electrical signal. In contrast to the traditional EMTAD approach, the disclosure describes methods and apparatus for combined CTAA and ESA to provide a more advantageous clinical application of EMTAD. The disclosure utilizes various aspects of CTAA in conjunction with ESA to provide reproducible, consistent, and efficacious HBV vaccine delivery. The methods and apparatus provided herein provide spatial and temporal control over administration of an HBV vaccine relative to the application of electrical signals, thereby improving the movement and/or uptake of said agent in the target tissue.

Methods

In an aspect, the disclosure described herein provides systems, kits and apparatus for use in methods for controlled administration of an HBV vaccine to a subject in need thereof followed by ESA. As used herein, "subject" means any animal, preferably a mammal, most preferably a human, to whom will be or has been treated by a method according to an embodiment of the application. The term "mammal" as used herein, encompasses any mammal. Examples of mammals include, but are not limited to, cows, horses, sheep, pigs, cats, dogs, mice, rats, rabbits, guinea pigs, non-human primates (NHPs) such as monkeys or apes, humans, etc., more preferably a human.

In another aspect, the disclosure described herein provides systems, kits and apparatus for use in methods for controlled administration of an HBV vaccine preceded by ESA. In a further aspect, the disclosure described herein provides systems and apparatus for use in methods for controlled administration of an HBV vaccine accompanied by ESA. These methods include, but are not limited in scope or sequential relationship to, the determination of treatment parameters, subject preparation procedures, CTAA, ESA, and additional measures.

Determination of Treatment Parameters

In some embodiments, treatment parameters are based on the desired amounts and/or duration of dosing of the HBV vaccine. HBV vaccine dosing can depend, for instance, on the particular indication or treatment application (such as the type and location of the target tissue), as well as various subject parameters (such as age and body mass). Dosing of the HBV vaccine can be controlled by parameters pertaining to administration of the HBV vaccine and ESA. Exemplary controllable parameters pertaining to CTAA include, but are not limited to, agent volume, agent viscosity, and injection rate. Exemplary controllable parameters pertaining to ESA include, but are not limited to, the characteristics of the electrical signals, the tissue volume exposed to the electrical signals, and the electrode array format. The relative timing and location of CTAA and ESA are parameters providing further control over HBV vaccine dosing.

Subject Preparation

In embodiments described herein, methods described herein can include a subject preparation step. The subject preparation can include, but is not limited to, antiseptic cleansing and anesthetic administration, including local or regional, nerve block, spinal block, epidural block, or general anesthesia. In an exemplary case of intramuscular (IM) ESA, protocols to minimize the effects of electrical stimulation of the muscle can be included in a method described herein, for instance, including thermal control (e.g. cooling the muscle), administration of anesthetics, and/or alternative stimulation patterns sufficient for mitigation of discomfort. It is to be understood that the selected subject preparation techniques do not adversely affect therapeutic efficacy, if acceptable alternatives exist. For example, it has been shown that in some cases, the intramuscular administration of amide based anesthetics can have an undesirable effect on intramuscular delivery plasmid DNA-based therapies, putatively due to the mild myotoxicity of these agents, which can inhibit the muscle cells ability to express the protein encoded by the administered DNA sequence.

CTAA and ESA

In some embodiments described herein, is a method wherein CTAA and ESA are combined, enabling consistent and reproducible HBV vaccine delivery. In some cases, are provided apparatus or kits suitable for CTAA, including for instance apparatus comprising at least one of automatic injection devices and jet injectors.

Figure 2:
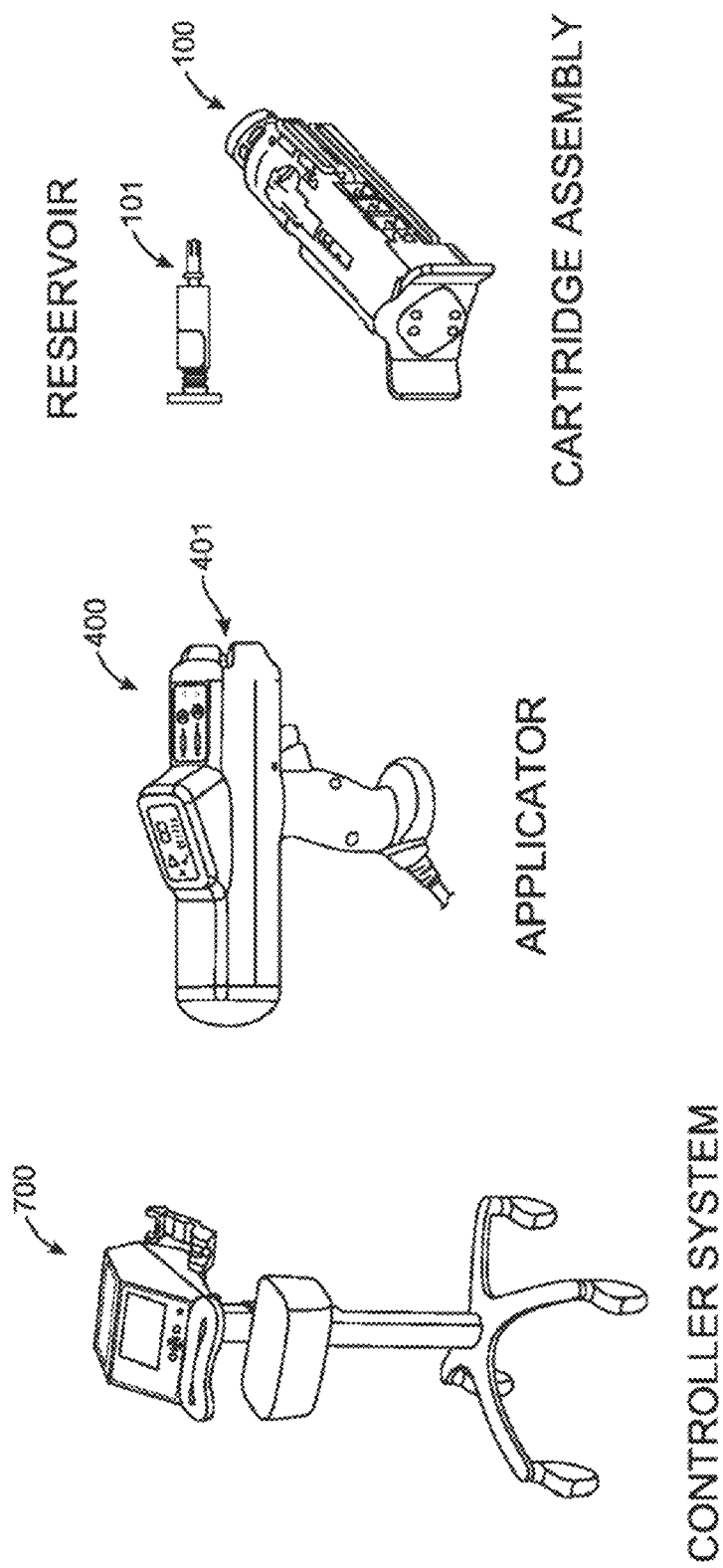

The disclosure provides methods, kits and apparatus enabling the transcutaneous deployment of a plurality of elongate electrodes to a target depth in a safe and consistent manner with respect to a target site of agent distribution in recipients with heterogeneous skin thickness and composition in order to support the application of electrical fields in tissue to enhance the intramuscular, intradermal, and/or subcutaneous administration of therapeutic or prophylactic agents such as nucleic acids, pharmaceuticals, antibodies, peptides, proteins, or combinations thereof.

Systems and methods according to present principles enable the consistent transcutaneous deployment of a plurality of elongate, tissue penetrating electrodes to a predetermined target tissue site in order to propagate electrical fields in the skin, subcutaneous tissue and/or skeletal muscle. The disclosure provided herein is designed to enable a user with minimal training to consistently deploy the electrodes to a target depth while maintaining the proper spatial relationship among the plurality of electrodes, even when the procedure is applied at sites with varying skin characteristics. Such variation can be due either to variation in skin characteristics at different sites within an individual or among heterogeneous recipient populations. In other words, systems and methods according to present principles should allow a consistent profile irrespective of the administrator or the recipient. In certain embodiments, the deployment of the electrodes is accompanied by the insertion of one or more injection needles which are configured for the administration of HBV vaccines to the target region of tissue and arranged in a pre-determined spatial relationship with the electrodes to be used for ESA. In an exemplary embodiment, the electrodes are arranged such that any electrical signals from said electrodes are preferentially applied distal to the site of HBV vaccine administration by the insertion of one or more injection needles. In another embodiment, the electrodes are arranged such that any electrical signals are preferentially applied proximal to the site of HBV vaccine administration by the insertion of one or more injection needles.

Aspects of the disclosure can be used singly or in combination to support the transcutaneous insertion of electrodes for the in vivo application of electrical fields to enhance the intramuscular, intradermal, and/or subcutaneous administration of nucleic acids, small molecule drugs, antibodies, peptides, proteins, and combinations thereof. In some embodiments, the electrode deployment and subsequent electrical field propagation are performed in coordinated fashion with the distribution of the agent of interest to the target tissue site. In an exemplary embodiment, the administration of the agent and the application of one or more electrical fields are performed in a controlled and monitored fashion such that the probability of achieving spatial and temporal co-localization of the distribution of the agent with the site of electric field application is maximized.

In general terms, the disclosure provides methods and apparatus for the transcutaneous deployment of electrodes to a predetermined site within the skin, subcutaneous tissue, and/or skeletal muscle of a recipient in conjunction with the administration of an agent of interest and the local application of electrical fields to improve the delivery, uptake, and/or biological effect of the agent. In some embodiments, the disclosure has been implemented such that set up and usage of the device can be performed effectively and reliably by users with minimal training. In another embodiment, the disclosure also comprises the implementation of numerous interlocks, sensors, and feedback loops to reduce the frequency and/or potential impact of potential user errors committed during the set up and use of the device. Referring to FIG. 2, an embodiment of an apparatus described herein comprises a "cartridge assembly" 100 detachably interfaced to an "applicator" 400 which is configured to connect to a controller 700 which acts as source of electrical energy for electrode activation and subsequent electrical field generation, as well as diagnostics and other control routines. The controller 700 further provides a user interface, tray, holster for the applicator 400, and various other features are described. As seen in FIG. 2, a reservoir 101 of suitable uniform size and general shape can inserted in the cartridge assembly 100 in a method of use.

Details of a cartridge assembly 100 present in some embodiments of an apparatus described herein, are described for instance, in FIGS. 3A-12, along with corresponding cooperating portions of the applicator 400, in FIGS. 13A-18C, followed by, where relevant, portions of the controller 700, in FIGS. 19-20D. Remaining portions of the applicator 400 are described next, followed by remaining portions of the controller 700.

Figure 3A:
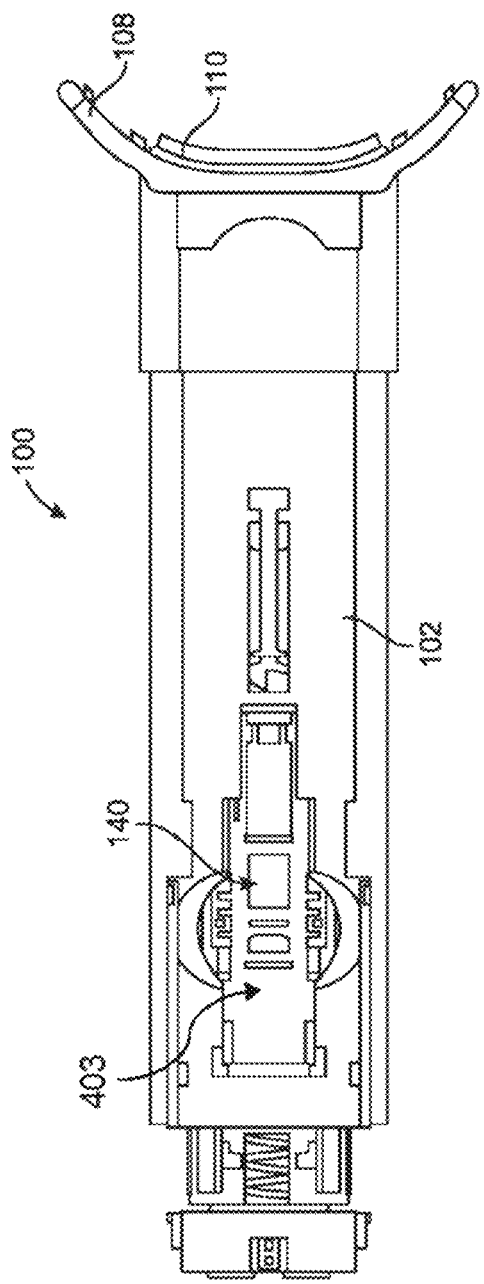
Figure 3B:
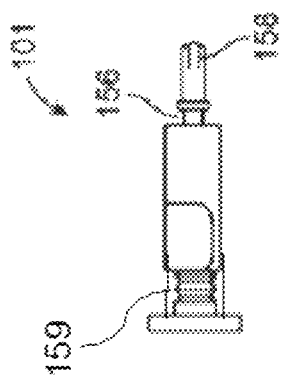
Figure 4:
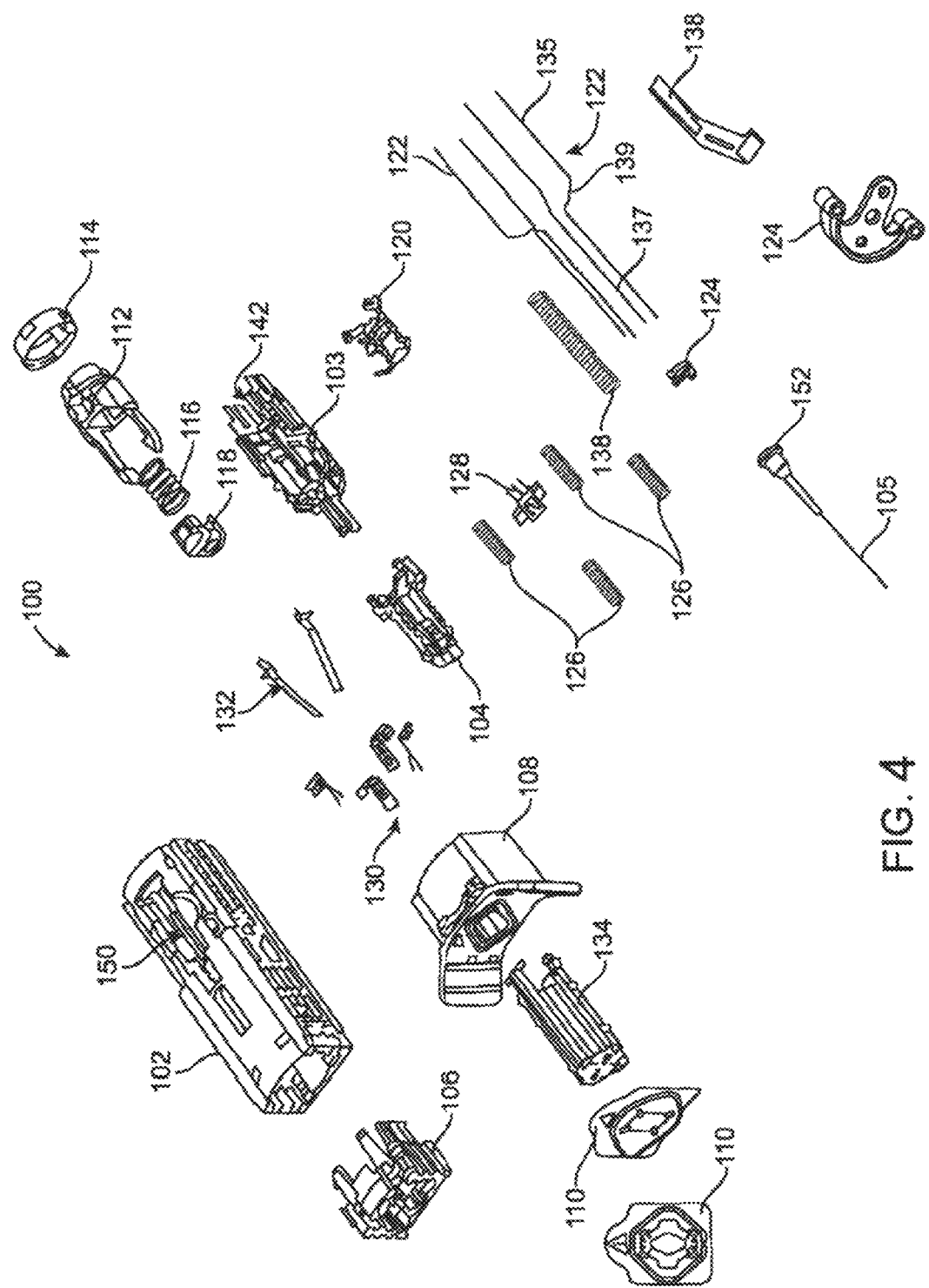

Referring in addition to FIGS. 3A-4, in some embodiments described herein, the cartridge assembly 100 can comprise a support structure configured to interface with the applicator 400 and accommodating two or more elongate electrodes 122 mounted on the structure to form an array. To avoid unwanted propagation of electrical currents within the device, the design and materials of the electrode mounting structure should be specified such that there is an adequate dielectric barrier between electrodes of opposite polarity within the device. The distal region 137 of the elongate electrodes are engaged with the mounting structure using standard mechanical features and/or bonding agents appropriate for the material composition of the electrode mount structure and the electrodes.

In an exemplary embodiment, the cartridge outer housing structure 102 is configured to interface with a fluid reservoir 101 containing the HBV vaccine where the reservoir 101 and cartridge housing structure 102 are configured to operatively connect to at least one injection orifice (needle 105) through which the HBV vaccine is administered into the target tissue. In some embodiments, this configuration facilitates the co-localization of the distribution of the agent of interest with the site of electrical field application. In another embodiment, this configuration facilitates the implementation of a pre-determined spatial relationship between the apparatus for ESA and CTAA. In yet another exemplary embodiment, a syringe 101 is inserted into a cartridge 100, wherein upon loading of the cartridge into an applicator 400, the syringe 101 moves forward to mate with the needle hub 152 and to connect the cartridge to the needle.

Certain embodiments of the disclosure can include the use of syringes, vials, ampoules, cartridges or equivalent structures for storing one or more HBV vaccines. In some embodiments, the reservoirs can comprise at least one of glass and plastic, with the material selected for compatibility with the agent of interest. Coatings can be applied to the reservoir used to provide desirable lubricious or protective properties. As disclosed above, the electrodes 122 can be hollow and in some cases configured with injection orifices that can be operatively connected to the fluid reservoirs. Alternatively, the injection orifice can comprise one or more hypodermic needles and/or needle free injection ports positioned relative to the electrodes. Selection of the type and size of injection orifice can dependent on the desired route of administration, tissue distribution, and physical characteristics of the agent of interest. In a certain embodiment, the cartridge structure is designed to ensure a pre-determined spatial relationship between the injection orifice and electrodes in their deployed state such that the distribution of the agent of interest occurs substantially in the tissue bounded by the conductive regions of the plurality of electrodes. To minimize the need for handling of sharps by the user, in a certain embodiment, a cartridge 100 designed for use with hypodermic needles is configured to allow the hypodermic needle to be mated to the cartridge at the time of manufacture rather than the more common convention of mating the needle to the syringe at the time of use. In certain embodiments, an aspect of the disclosure can incorporate features in the cartridge and/or the needle to ensure retention of the needle during manufacture, distribution, handling, and use as well as features to ensure that proper mating of the reservoir to the needle prior to the use. In some embodiments, such features can minimize the risks of leakage of the agent from the reservoir or the reservoir orifice interface due to breakage or improper mating.

In certain embodiments, the cartridge can include a tissue contact interface located at the distal end of the subassembly. In certain embodiments, the tissue contact interface comprises a substantially planar structure oriented perpendicular to the elongate orientation of the electrodes and having one or more apertures configured to allow passage of the electrodes through the tissue contact interface. For embodiments incorporating an integrated reservoir and injection orifice, the interface also has apertures to accommodate injection orifice or needle free injection. To minimize the risk of contamination of the electrodes and injection needle as well as the occurrence of unintended sharps exposure to the user or recipient, in a certain embodiment, the apertures accommodating passage of the electrodes and injection needle are of a size suitable to prevent accidental contact with the electrodes and injection needle. Most commonly, the tissue contact interface is comprised of one or more plastics suitable for at least short term tissue contact.

To avoid potential cross contamination of biological material between recipients, the cartridge assembly 100 can be configured for single use. In some cases, the cartridge includes one or more mechanical, electrical, and/or identification elements which restrict use of the cartridge to a single administration. Examples of mechanical elements of this nature include for instance, but are not restricted to, lockouts and/or detents which secure the electrode mount structure and/or the stick shield (see below) in the deployed state after use. Examples of electrical elements include for instance, fuses or links configured in series with one or more electrodes which are deactivated by the source of electrical energy at the conclusion of the first use of the cartridge. Examples of identification elements include, for instance, serialized radio frequency identification devices, bar codes, or quick response codes configured to be read by the applicator and/or the source of electrical energy. The identification information for a specific cartridge can then be used to prevent accidental or intentional re-use of that cartridge by the applicator and/or the source of energy. In an embodiment, one or more redundant features are incorporated to minimize the potential for re-use of the cartridges.

In an embodiment of an apparatus described herein, as shown in FIG. 2, the applicator 400 comprises a support structure configured to interface with the cartridge assembly 100, a user interface 410-418 (FIG. 13B), electrically conductive electrical connections configured to provide operative connection between the conductive contact region located on the distal region of the elongate electrodes and the source of electrical energy when the electrodes are deployed into the target tissue of the recipient. In some cases, the user interface comprises a handle, one or more display features designed to convey information to the user, and one or more features capable of accepting user input. In certain embodiments, the display features are configured to convey the operating status of the device during its set up and use as well as relevant warning/error messages. Such displays can comprise mechanical features, lights, alphanumeric displays, and/or electronic display screens. In some cases, the features capable of accepting user input are configured to allow the user, at the appropriate stage of the procedure, to de-activate safety features within the device preventing accidental discharge, make selections regarding particular parameters of the procedure (e.g., the intended depth of injection), and to initiate procedure administration and can include buttons, triggers, mechanical slides, and/or levers.

In certain embodiments, the applicator 400 also includes actuation mechanisms which interface with the cartridge assembly and which are configured for transcutaneous deployment of the electrodes, positioning of the injection orifice relative to the target tissues, discharge of the agent of interest from the reservoir through the orifice and into the target tissue site, and/or conveying electrical signals from an electric field generator such as a controller 700 to the cartridge 100. The applicator 400 can be configured such that the energy to actuate the mechanisms is supplied by the user, or more preferably, the apparatus may incorporate one or more inanimate sources of energy operatively connected to the actuation mechanisms within the applicator. Such inanimate sources of energy include for instance, electro-mechanical devices (solenoids, motors, lead screws), mechanical components (springs and related devices), and compressed gases.

An exemplary implementation of a cartridge assembly 100 is as described in FIG. 3A, a cartridge assembly 100 includes a reservoir loading port 140 and a reservoir containment volume 142 to receive and contain a reservoir 101 of a medicament. A cartridge assembly 100 is required because, for a device in which an electrical field is to be generated and used as part of a therapy, an electric field generator such as a controller 700 is required to electrically interface with the device containing the electrodes configured to contact the target tissue. As the controller can be configured for multiple uses, and the reservoir 101 can be intended for single use, the cartridge assembly 100 can be present to hold the electrodes 122 and, the reservoir 101, to interface with the re-usable device, and for the cartridge assembly 100 to be configured for single use. Thus, the applicator 400 can be a reusable component and the cartridge assembly 100 can be configured for single use. The cartridge assembly 100 can also be rendered in a condition to prevent subsequent use if errors or tampering occur in the insertion of a reservoir 101, or if defects are present.

The term reservoir 101 can refer to a syringe, vial, or any other device which can contain a medicament or HBV vaccine and which can interface with a device having an orifice, such as a needle, shown in FIG. 4 as a needle 105 having a needle hub 152. The reservoir 101, for a given type of cartridge assembly 100, generally has a common shape and size. Various components within the cartridge assembly 100 allow for a leeway in exact sizing and/or manufacturing tolerances, but generally a common shape and size are required to reduce the risk that drugs not labeled for use with cartridge 100 are erroneously delivered with the device. If an appropriately sized reservoir 101 is not provided by the user, one or more interlocks within the cartridge assembly 100 can be unable to deactivate, and the system can be rendered unusable until a proper-sized reservoir 101 is inserted.

As seen in FIG. 3B, the reservoir 101 generally can be equipped with a plunger and a port 156 for drug egress. A removable cap 158 can also be provided to maintain the sterility and integrity of the agent until such time as the reservoir is to be inserted and used. The port for drug egress can be proximal to the needle hub 152 in use, and the plunger can be opposite this port for drug egress. As an alternative to an open port for drug egress, in some embodiments, the reservoir can be configured with a septum component which covers and seals the end of the container opposite the plunger. The septum can be made of elastomeric compounds such as silicone or butyl rubber, with the specific formulation and coating of the material selected for stability and compatibility with the agent contained within the reservoir. The septum component is typically held in place by a crimp seal or other fastening mechanism. This septum seal configuration obviates the need for a removable cap, but requires that needle 105 be equipped with a suitable piercing member such as a needle, spike, or other features to access the fluid contained in the reservoir. Specific implementations for this configuration include dual sided needle configurations and spike vial adapters.

The cartridge assembly 100 is not only configured for receiving the reservoir 101 but also for being received by an applicator 400 in an applicator cartridge assembly receiving port 401 (FIG. 2). Thus, the cartridge assembly 100 includes a device allowing the applicator 400 to pull and retain the same within an interior volume, at least partially. In certain embodiments, the device is one or more racks on the surface(s) of the cartridge assembly 100 that engage a corresponding motorized pinion assembly in the applicator 400. In other implementations, the applicator 400 can interface with the cartridge assembly 100 without the need to pull the same into an interior volume. In yet other implementations, other techniques can be employed to cause the cartridge assembly 100 to engage the applicator 400, e.g., motorized tracks or brackets and the like onto which the cartridge assembly 100 can interface.

The applicator 400 is further provided with interface elements allowing the same to control certain actions within the cartridge assembly 100. In particular, the applicator 400 can be configured to control needle insertion, medicament delivery, electrode insertion, and electrode activation using various subsystems. In some cases these steps are linked, so that a single action of applicator 400 initiates multiple of these steps. In some implementations, all of these steps but the medicament delivery and electrode activation are caused by a single action, as described in the exemplary implementation below.

Upon appropriate activation, such as the use of electrical or optical signals conveyed to mechanical, electrical, or optical elements of the cartridge assembly 100, the applicator 400 can be enabled to test subsystems within the cartridge assembly 100, ensuring that the same are operating properly and are properly configured for medicament delivery with electric field application. For example, such subsystems include that the applicator 400 can test to ensure that the cartridge assembly 100 has not been previously used, that the reservoir has been properly placed within the cartridge assembly, that appropriate force applied against the body of a subject as applied through an alignment guide/splay shield 108, a test that a depth has been affirmatively selected by the user, and that an exterior cartridge cap 110 has been removed. Moreover, the applicator 400 can be configured to monitor the status of the cartridge functions during execution of the procedure. For example, such subsystems include that the applicator 400 can test to ensure that that electrodes 122 are properly deployed within a subject prior to commencing with administration of the medicament, that the plunger in the reservoir has been appropriately actuated prior to application of the electrical fields, that the user has maintained appropriate force applied against the body of the subject during the administration procedure, and so on.

In addition to the subsystems that are operated by the applicator 400, the cartridge assembly 100 can incorporate appropriate subsystems, including those that interact with the applicator 400 and those that do not so interact, so as to accomplish the goals of the medicament delivery and electric field application therapy. These include a subsystem for causing needle and electrode insertion, a subsystem for protecting users from sharps following therapy administration, a subsystem for providing different depths of needle/electrodes insertion, a subsystem for ensuring that adequate force has been applied against the tissue of the recipient prior to allowing initiation of the procedure and subsequently during application of the administration procedure and so on. While often described in the context of deployable needles and electrodes, it is noted here that such are not strictly required, and that systems with non-deployable or fixed needles and electrodes also benefits from systems and methods according to present principles, including the subsystems described.

In one exemplary implementation, as shown in FIG. 4, the cartridge assembly 100 includes an outer cartridge 102, in some cases termed a housing. The outer cartridge 102 is terminated at a distal end by an outer cartridge cap 106. The outer cartridge 102 includes an inner cartridge containment volume 150, for receiving an inner cartridge 103, which is received and moves in a slidable manner in relationship to the outer cartridge 102. The inner cartridge 103 includes a reservoir containment volume 142 in which the reservoir 101 can be situated. The inner cartridge 103 engages with an inner cartridge cap 104 at a distal end. The inner cartridge cap 104 has a number of functions, including to lock electrodes 122 in place (the inner cartridge 103 itself has seams that the electrodes 122 are placed into) and to provide a bearing surface for a stick shield 134. The inner cartridge cap 104 locks onto the inner cartridge 103.

A cartridge breech 112 is received in a portion of the reservoir containment volume 142 in the inner cartridge 103, in a portion opposite that of the inner cartridge cap 104. A reservoir detection cap 118 engages the cartridge breech 112 through a reservoir detection spring 116. A cartridge lock ring 114 locks the system in place, including the cartridge breech 112 to the inner cartridge 103. The reservoir detection spring 116 also serves to push the reservoir 101 into engagement with the needle hub 152, and also serves to accommodate tolerances in the size of reservoir 101.

A reservoir interlock 120 provides a mechanical interlock to prevent inadvertent or unwanted actuation of cartridge functions. In particular, the reservoir interlock 120, also termed a first reservoir insertion trigger, is placed below the inner cartridge 103 and has fingers that extend through slots or holes defined in the inner cartridge 103 (see FIG. 5B). The fingers prevent the cartridge breech 112 from slidably moving relative to the inner cartridge 103, and in particular from moving within the inner cartridge 103 towards the inner cartridge cap 104 before a reservoir has been inserted into a reservoir containment volume 142.

When a reservoir 101 is properly inserted in the reservoir containment volume 142, the reservoir interlock 120 is pushed down and the fingers are pushed down, no longer extending into the reservoir containment volume 142. This pushing down or depression of the reservoir interlock 120 may also be configured to provide an audible, tactile, or haptic "click" that can inform the user of proper insertion. Once depressed, the cartridge breech 112, no longer blocked by the fingers of reservoir interlock 120, is then permitted to move, and in particular is permitted to move in the direction towards the inner cartridge cap 104.

The cartridge breech 112 is caused to move such by the action of the spring cap/cartridge interface 470 when the cartridge assembly 100 is inserted in the applicator 400 in a fashion described below. When the cartridge breech 112 moves far enough forward, it locks in place, securing the reservoir 101 in the reservoir containment volume 142 and ensuring that it is properly positioned relative to the needle hub 152 to ensure an intact fluid pathway from the reservoir 101 to the orifice of needle 105.

For embodiments of the device where the injection needle is incorporated into the cartridge 100, the use of standard "off the shelf" single use hypodermic injection needles can be employed within the device. However, the operational and reliability characteristics of the device can be improved through the incorporation of customized design elements that are not present in hypodermic needles intended for conventional parenteral administration procedures. Specific aspects of the needle hub 152 can include the material from which it is comprised, the inclusion of retention features to prevent the needle hub 152 from becoming dislodged from inner cartridge 103 during distribution and use, and the orientation of any bevel features in the needle relative to the hub.

Conventional single use disposable injection needles are commonly comprised of injection molded polypropylene thermoplastic. However, for many applications, the impact strength, tensile strength, and flexural strength of polypropylene may not be adequate to ensure integrity of the hub when subjected to the forces characteristic of needle deployment and injection with this device. Specific failures of concern include failure in the hub wall due to impact or injection forces as well as failure of the hub needle joint due to same. While adjustments in the design of the hub, including its geometry and wall thickness can be utilized to address prevent these failures, it is not always feasible to modify the design sufficiently to prevent hub failure while ensuring that the hub retains the dimensional properties required for proper mating to a conical male luer slip connectors as described in the relevant standard published by the International Standards Organization (ISO) ISO 80369-7:2016 Small-bore connectors for liquids and gases in healthcare applications—Part 7: Connectors for intravascular or hypodermic application. Specifically, given the forces that the syringe needle and hub are subjected to during deployment, in certain embodiments, a material with improved impact strength, tensile strength, and flexural strength is used. One example is the use of injection molded polycarbonate plastics (such as ZELUX® GS, Makrolon, or Lexan) or copolyesters (such as Eastman Tritan™ Copolyester MX731, MX711, and MX 730). When assessed according to ISO 180:2000 Plastics—Determination of Izod impact strength, a notched impact strength of at least 70 kJ/m2 is considered suitable for this application. When assessed according to the ISO 527-1:2012 Plastics—Determination of tensile properties—Part 1: General principles, a tensile strength of at least 30 MPa is considered suitable for this application. When assessed according to ISO 178:2010 Plastics—Determination of flexural properties, a flexural strength of at least 50 MPa is considered suitable for this application. In some embodiments, the specific resin selected exhibits compatibility with the intended method of sterilization (e.g., gamma radiation) without exhibiting detrimental changes in its physical properties that could compromise its function.

For embodiments where a custom injection needle is utilized, one or more mechanical features are included which are not ordinarily present on conventional syringe hubs that enable the device to be inserted into inner cartridge 103. Such features can include tabs, snaps, or ridges with corresponding mechanical features located on inner cartridge 103. In some cases, the features are implemented such that the hub mates with the inner cartridge 103 in a consistent orientation. Combined with a needle manufacturing process that is capable of consistently orienting the bevel or other needle orifice feature, this insures that biases in injection location or medicament distribution due to the location and design of the orifice can be accounted for in the design of the device. For example, needles with asymmetrical penetrating tip features (e.g., a bevel cut) can exhibit a directional bias during deployment into tissue due to interaction between the tissue and the asymmetrical penetration feature on the needle. If the electrodes have a symmetrical penetrating tip feature (e.g., a trocar tip) then the electrodes would not exhibit a corresponding bias in their deployment characteristics. Therefore, mounting feature for needle hub 152 on inner cartridge 103 can include an offset in the position of the injection orifice on needle 105 relative the electrodes 122 prior to deployment to account for the expected deployment characteristics of the asymmetrical bevel of the needle. The precise dimension of the offset can depend on the nature of the target tissue and the expected range of penetration depths, but in certain embodiments the needle is offset by 0.5-1 mm for each 10 mm of penetration depth. When using electrodes and injection needles with differing tip profiles or where the tip profiles must be consistently oriented with one another, such features are advantageous for insuring co-localization of the medicament distribution with the application of the electrical fields.

The incorporation of a syringe detection cap 118 mounted to a syringe detection spring 116 ensures that the cartridge assembly 100 can accept and properly position the syringe 101 relative to needle hub 152 across the range of manufacturing tolerances expected for syringe 101. The applicator 400 causes the cartridge breech 112 to move forward during the loading procedure when the spring cap/cartridge interface 470 within the applicator 400 moves distally, relative to the cartridge assembly 100. This action occurs when the cartridge assembly 100 is loaded into the applicator 400 and the cartridge assembly 100 is pulled into the applicator 400, e.g., by the action of a loading mechanism, e.g., a rack-and-pinion mechanism described below.

Figure 5C:
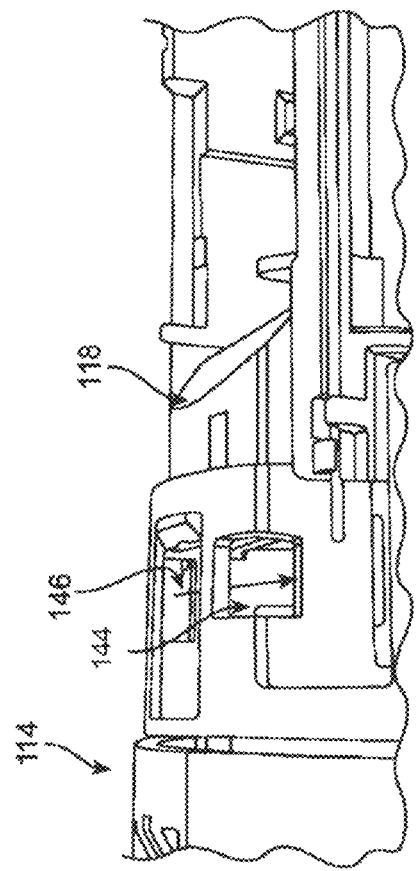
Figure 5D:
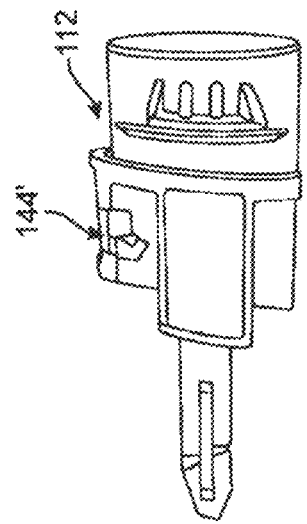
Figure 5A:
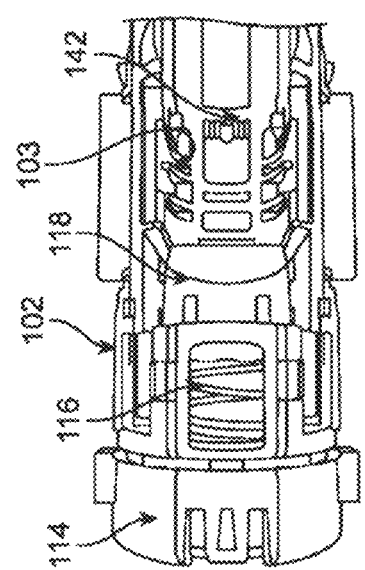
Figure 5B:
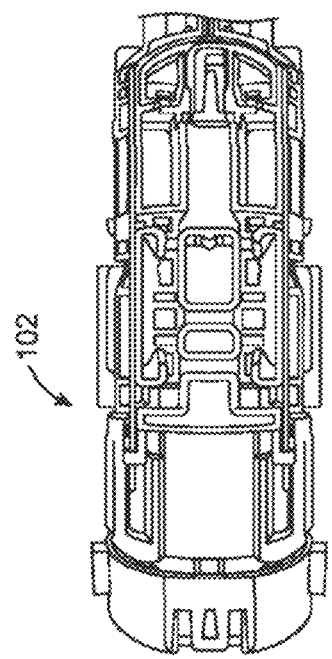
Figure 5E:
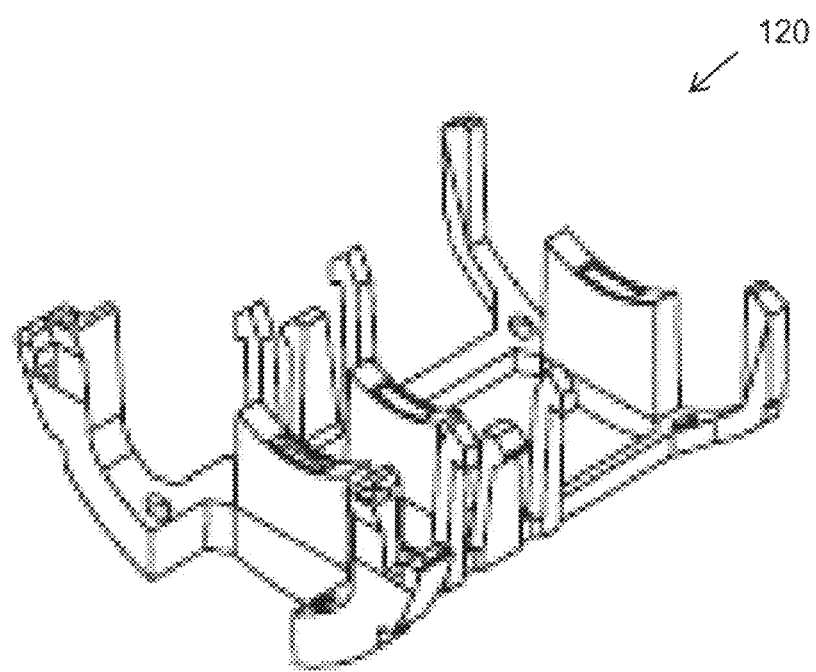
Figure 6:
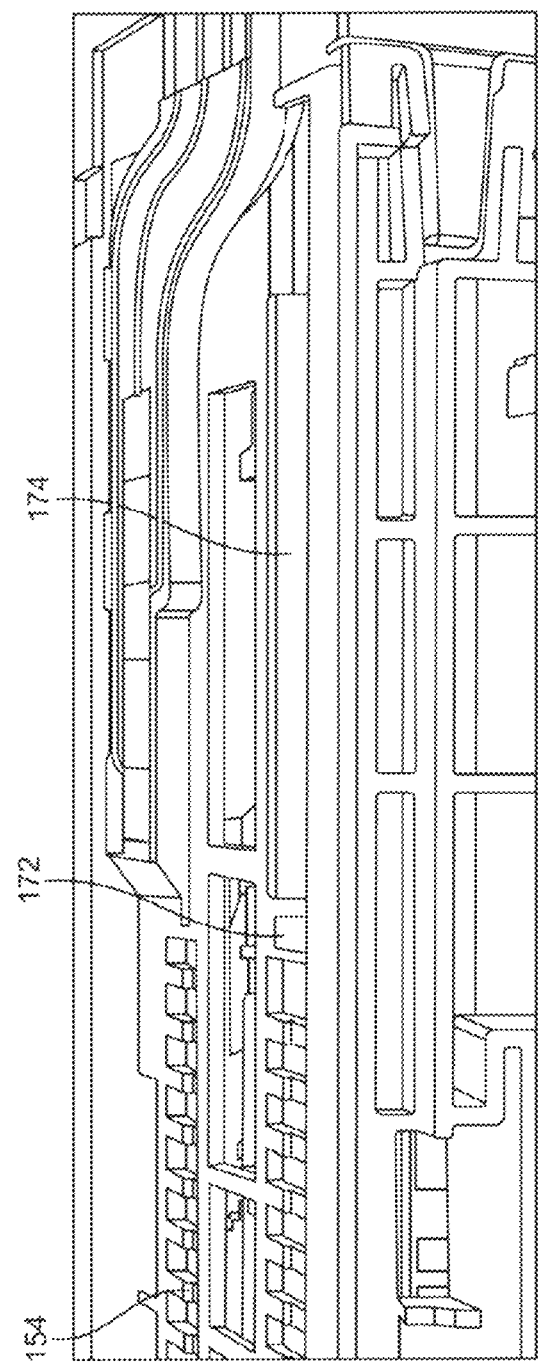

The movement of the cartridge breech 112 can act as a second interlock. In particular, in one implementation, as seen in FIGS. 5C-5D, a line of sight is visible and detectable, by an appropriately configured sensor, within the cartridge assembly receiving volume 403, through a set of reservoir locking holes 144' (FIG. 5D). This line of sight is visible when the cartridge assembly 100 is loaded into the applicator 400. The visible light of sight, or occlusion of the same, can act as part of a second interlock that must be deactivated for the controller 700 to allow activation and triggering of the device, including needle and electrode insertion, medicament delivery, and electrode activation.

For example, in one implementation, the reservoir locking holes 144' (FIG. 5D) must be occluded for the device to operate. If a visible line of sight is present, e.g., as detected by an IR or visible light emitter and detector paired within the cartridge assembly receiving volume 403 of the applicator, the device can be rendered inoperable and generate and display an error message on the applicator display 404 and/or controller 700, including the controller display 712, to notify the user of the state of the device as well as the recommended steps to be performed to address the error.

Thus, in this implementation, one error state can be that no reservoir 101 was loaded into the cartridge 100 or that the syringe was not properly seated into the inner cartridge 103. In this case, the reservoir interlock 120 cannot be depressed as there is no reservoir 101 to perform this action. In this case, the cartridge breech 112 cannot be moved forward, in the distal direction, towards the inner cartridge cap 104. The construction of these components can be such that an open breech state results in an open line of sight 146 through first reservoir locking holes 144' (FIG. 5D). An ancillary check is that the cartridge breech 112 cannot be closed, and this can manifest itself as an inability of the cartridge to move the required distance backward or distally into the cartridge assembly receiving volume 403. As these conditions are defined by the system to be an error state, the same can be identified and used in the generation of an error message, e.g., with an appropriate message to the user on a user interface on the applicator display 404 and/or controller 700, including the controller display 712. A similar error state may occur if the reservoir 101 is improperly loaded, or if the reservoir interlock 120 is damaged. Generally in this case, an appropriate error message can be accompanied by instructions to the user to remove the cartridge, reinstall a new reservoir, and attempt to reintroduce the cartridge assembly 100 into the applicator 400.

Another error state can be that the cartridge breech 112 is moved forward manually by the user without a reservoir 101 present, such occurring by the user manually pushing the reservoir interlock 120 out of the reservoir containment volume 142. This situation can also be defined as an error state, and the same can be detected because another (second) set of reservoir locking holes 144 (FIG. 5C) are placed on a portion of the outer cartridge 102. If no reservoir is in place, but the cartridge breech 112 is moved forward by the action of the reservoir interlock 120 being depressed, then the reservoir locking holes 144' (FIG. 5D) align with the reservoir locking holes 144 (FIG. 5C), again creating an open line of sight 146 and a subsequent error state. This error state may also occur if the reservoir interlock 120 is damaged and its fingers are no longer within the reservoir containment volume 142. In a certain embodiment, this error state need not be not remediable by attempting to reinstall a reservoir, as a reservoir may not fit in the reservoir containment volume 142 with the cartridge breech 112 locked. In a certain embodiment, a new cartridge assembly 100 is required.

In contrast, if an appropriately sized reservoir 101 is positioned properly in place, then the reservoir detection cap 118 is pushed back against the reservoir detection spring 116, and the movement of the reservoir detection cap 118 occludes the reservoir locking holes 144 (FIG. 5C) and the reservoir locking holes 144' (FIG. 5D). In this case there is no error state, allowing the device to operate. The occlusion, and detection of the occlusion, occurs within the body of the applicator 400, after the cartridge assembly 100 is inserted, and thus is unsusceptible to user attempts to defeat this interlock, whether intentional, accidental, or caused by a defect. It is noted that this "no error" state still occurs even if the user intentionally or inadvertently closes the cartridge breech 112 themselves during handling of the cartridge 100.

Depending on which error state occurs, the cartridge assembly 100 can remain usable or not. If the cartridge breech 112 has been locked into place, the cartridge assembly 100 is rendered unusable. If, however, the cartridge breech 112 has not been locked into place, then the cartridge assembly 100 can be removed from the applicator 400 and a new reservoir 101 inserted.

While the above-noted set of two interlocks (one mechanical using reservoir interlock 120 and one using a light emitter and collector and reservoir lockout holes 144 and 144') have been found particularly useful in some implementations, it is to be understood that other types of interlocks can also be employed (FIGS. 5C-5D). For example, instead of having an error state occur when the reservoir locking holes 144 are not occluded, the error state can be configured to occur (via a change in reservoir locking hole location and program logic) when the reservoir locking holes 144 are occluded (and the clear line of sight 146 then corresponding to the non-error state). The reservoir interlock 120 can incorporate additional mechanical flag features that are recessed in the cartridge when the interlock is active, but become visible to an appropriately configured sensor when the syringe 101 has been properly inserted and the reservoir interlock 120 is depressed into its released position. In other variations, other ways can be employed to determine if a line of sight is present, e.g., optical, acoustic, electrical, or the like, so long as a suitable emitter and collector can be positioned within the applicator 400. Other ways may also be employed to determine if the reservoir 101 is properly loaded, e.g., mechanical techniques, as it is to be understood by one of ordinary skill in the art given this teaching. Depending on implementation, if an error state is detected, the applicator 400 can be prevented from operating either with the cartridge assembly 100 in place, or the applicator 400 can be prevented from even accepting the cartridge assembly 100 in the first place. For example, the cartridge can be designed such that the reservoir interlock 120 includes mechanical tab or locking features which extend from one or more of the cartridge surfaces until a syringe 101 is properly inserted into the cartridge 100. The mechanical tabs are designed to interact with a corresponding detent feature located in the applicator 400 such that loading of the cartridge 100 into the applicator 400 is physically blocked unless the reservoir interlock 120 is released. This mechanical interaction would provide feedback to the user or the system that an error condition must be resolved before proceeding with the loading of the cartridge 100 into applicator 400. In other variations, more or less than two interlocks can be provided, although the same can be correspondingly associated with a different safety profile.

In certain implementations, other features can also be employed in the above determinations, or to enhance the above determinations. For example, where a motor is employed to pull the cartridge assembly 100 into the applicator 400, sensors can be employed as described below to detect the spatial position of the cartridge assembly 100 during the insertion process. Put another way, the applicator 400 may detect where the cartridge assembly 100 is within the cartridge assembly receiving volume 403. In some cases, such may allow determination of additional error states either directly, or by prompting the activation of additional sensors to assess the state of the device. For example, in a used cartridge, the cartridge breech 112 is locked into position. If the used cartridge assembly 100 is attempted to be re-used, the optical detector detects the cartridge assembly 100 at a different point than it would for an unused cartridge assembly 100. The use of an electrical motor for one or more system functions also provides the opportunity to monitor its operational status including the voltage and current levels supplied to the motor as well as the number of revolutions that the motor has performed during a specific operation. Measurement of these quantities during system operation can be used as a primary or secondary method for detecting potential or actual fault conditions. For example, the use of mechanical interlocks designed to block the loading procedure when the cartridge 100 is not properly configured can be coupled with sensors and logical circuits monitoring the motor to ensure proper loading of the cartridge 100 into applicator 400. For example, the interaction of the mechanical features described above that are designed to prevent the loading of cartridge 100 without a properly inserted reservoir 102 would result in increased load on the motor drive mechanism, resulting in a higher current draw. Detection of the elevated current draw by the motor would prompt the loading procedure to be halted and a fault condition displayed to the user, for example on stimulator display 712 and/or applicator display 404.

Since it is possible that medicaments not intended for administration by this method could be contained within reservoirs of similar size and configuration as that intended for use by this delivery method. Therefore, an additional aspect of the system is the incorporation of one or more methods to ensure that the reservoir 101 inserted into the cartridge 100 by the user is specifically, intended for use with the device. The implementation of such features would reduce the risk that an incorrect medicament is administered to a given subject. Customarily, specific information in the user instructions and labeling of the medicament includes the route and method of administration. However, to further reduce the potential for user errors, the incorporation of mechanical, optical, and/or electrical features within the reservoir and device can be desirable. In an embodiment, the syringe can be designed to incorporate one or more unique mechanical features that are not present in other reservoirs which can be similar to those designed for use with this delivery method. For example, the reservoir can be specified to incorporate a rib or other elongate feature on the flange or barrel of the reservoir. In this embodiment, a corresponding mating feature would be included on the reservoir interlock 120 such that the reservoir interlock would be deactivated only if a reservoir with the appropriate mating feature were properly inserted into the device. In the event that it is not feasible to directly implement the feature in the design of the reservoir, an alternative embodiment would include the placement of a secondary mechanical component on the reservoir that would be unique to reservoirs intended for use with the device. For example, a ring or other appropriately configured feature designed to slide over the barrel of the reservoir can be used to "key" the reservoir for use with the device by mating with a corresponding feature in the outer cartridge 102, inner cartridge 103, reservoir interlock 120, reservoir detection cap 118, or other suitable feature within the cartridge 100. An additional embodiment a custom label of suitable size, color, and/or electrical conductivity applied to a pre-determined location on the outer surface of reservoirs that are intended for use with the device. Corresponding optical or electrical sensors in applicator 400 would be configured to assess the presence or absence of the label on the surface of the reservoir in order to verify that the medicament inserted into the cartridge is intended for use with the device. The detection method would comprise the use of optical or electrical signals applied to the surface of the label in order to assess its presence or absence. In this way, reservoirs containing medicaments not intended for use with the device (and therefore missing the relevant label) could be detected and excluded from potential misuse.

A configuration of sensors is now described to perform the cartridge loading and syringe detection determination described above, such sensors further forming a portion of a cartridge loading subassembly within the application 400. In more detail, and referring in addition to FIGS. 6, 17B, and 18C, an exemplary way of detecting where the cartridge assembly 100 is located is by use of a cartridge loading sensor 436 and a cartridge loaded sensor 438, which forms a portion of a loading drive subassembly 454, the subassembly 454 further including cartridge guide rails 442 and a loading motor 444 which has a connection to a pinion gear assembly 448 that pulls the cartridge assembly 100 into the cartridge assembly receiving volume 403 via racks 154 on the base of the outer cartridge 102. In more detail, when the cartridge loading sensor 436 detects an initiating flag 172 on the cartridge assembly 100 (see FIG. 6), the motor can be caused to initiate loading. When the cartridge loaded sensor 438 detects the same flag, loading can be caused to cease. A continuing flag 174 can be employed that is required to be present for loading to continue.

The first "teeth" of the rack 154 can be configured to provide a tactile sensation (or audible or haptic) for the user when they are inserting the cartridge assembly 100 into the cartridge assembly receiving volume 403. Such configuration may include the shape and/or size of the rack teeth 154 as well as the amount of flexion permitted by their positioning in the outer cartridge. By adapting the rack teeth implementation, the desired degree of tactile feedback can be achieved while ensuring that it does not provide a significant force against the loading motor 444 from receiving and loading the cartridge assembly 100.

Referring in addition to FIG. 17A, and as noted above, the cartridge assembly 100 is inserted into a cartridge assembly receiving volume 403 within the applicator 400. While various ways can be employed to perform this insertion, one way that has been found particularly useful is by way of a pinion gear assembly 448 engaging racks 154 on the outer cartridge 102. The use of more than one rack provides additional stability, particularly torsional stability during the loading phase. Referring also to the insertion/injection drive assembly 456 of FIG. 18A, in addition to drawing the cartridge assembly 100 within the cartridge assembly receiving volume 403, the insertion action further compresses an electrode/needle insertion spring 472 through a spring cap/cartridge interface 470. The electrode/needle insertion spring 472 is used as the primary driving force for the needle and electrode insertion during medicament delivery.

This hybrid motor/spring action provides numerous benefits. The motor drive is beneficial as it is highly controllable and allows the cartridge 100 to be loaded into the applicator 400 in a semi-automated fashion with minimal input of mechanical force required by the user. As described above, the implementation of motor drive based mechanisms provides monitoring of the operational status of the system. For instance, conveying the current draw and revolution count to the logical and control circuitry in the system provides a supplementary method for detection and diagnosis of potential fault conditions. Despite these advantages, in certain cases electric motors can be poorly adapted to exerting the necessary linear force over sufficiently brief time scales that is most desirable for effective transcutaneous deployment of arrays comprising a plurality of elongate electrodes and, in selected embodiments, hypodermic injection needles. In particular, the penetration of dermal tissues is most consistently achieved by the application of a large linear force over a brief time scale. In some embodiments, the most favorable insertion characteristics are achieved when the penetrating electrodes, and when present, injection needle contact the skin at higher velocity. This is because sharps travelling at increased velocity at the point of skin contact result in less tissue deformation as they cut or penetrate the tissue. Therefore, in some embodiments, rapidly accelerating the sharps prior to contact with the skin is desired. In some embodiments, multiple electrodes and an injection needle are frequently utilized. In another embodiment, the velocity of the electrodes is at least 50 mm/second prior to contact with the skin. In yet another embodiment, the velocity of the electrode is at least 500 mm/second prior to contact with the skin. This deployment approach minimizes the discomfort perceived by the subject during the electrode penetration and is most favorable for maintaining a consistent spatial relationship between the plurality of electrodes. In contrast to electromechanical motors, spring driven mechanisms exhibit a more favorable discharge profile that is capable of imparting the rapid impulse force to the electrodes and injection needle that is desirable for transcutaneous electrode implantation. In particular, the force exerted by a compression spring is at its peak at initial discharge. This is favorable for transcutaneous deployment where a high velocity at the point of skin contact is favorable and, due to the viscoelasticity of skin tissue, the greatest force is required for penetration of the skin, particularly when contacting the skin with a plurality of electrodes and/or injection needles. In addition, a spring based mechanism is capable of generating this force from a simple, durable, and compact form factor that can be readily integrated into a handheld device format. However, a disadvantage of spring based mechanisms is that they typically require the input of substantial mechanical force by the user in order to prime them for operation, especially for springs with high force constants and/or large displacements. The use of a hybrid motor and spring mechanism, as described in the disclosure, achieves the desired deployment force characteristics while being simple for the user to operate. While the hybrid motor and spring mechanism is a preferred embodiment, depending on implementation, other hybrid mechanisms incorporating two or more drive mechanisms wherein one is capable of generating a rapid impulse force and the other is capable of priming the impulse force mechanism, e.g., a pump capable of compressing gas into a chamber and then discharging the compressed gas in order to apply an impulse force for deployment of the electrodes and, where applicable, hypodermic needle(s) can also be used.

In any case, once loaded, the desired depth electrode deployment and/or agent administration is affirmatively selected by the physician or other medicament administrator and the same transmitted to the applicator 400. Referring in addition to FIG. 13B, the depth can be selected by depth selection buttons 409 (or other equivalent interface such as a toggle switch or sliding switch) and the result displayed on injection depth selection indicators 408 (or, again, other equivalent interface). The available injection depths are conveyed to the user by appropriate labeling of the applicator 400 and/or the cartridge 100. In some embodiments, any labeling regarding the injection depth is located on the cartridge 100 and remains visible to the user following installation in the applicator 400. For example, the available injection depths can be labeled on the upper surface of the alignment guide/splay shield 108. In order to avoid circumstances in which the user forgets or neglects to select a depth of injection, it is preferable that the device does not allow the user to proceed with the administration procedure until such affirmative selection is made. This can be accomplished by the implementation of appropriate control logic within the system such that subsequent elements of the device set up or usage are not accessible until a valid depth selection has been entered by the user. In certain embodiments, when the user is prompted to affirmatively select the injection depth, the controller display may convey to the user information regarding the proper methods for assessing the subject and determining the appropriate injection depth for the selected administration site.

Referring in addition to FIGS. 18A-18B, upon proper cartridge assembly insertion, the spring cap/cartridge interface 470 engages and also presses against the spring cover hole 471 and tabs 491. While a large spring force presses against the inner cartridge 103, the same is prevented from moving forward by engagement of a set of retaining posts 488 against walls 494 of the outer cartridge 102. However, the force exerted by 470 splays apart tabs 491 (which prevent inadvertent rotation of the lock ring during handling) thereby allowing rotation of the cartridge lock ring 114 by the motor drive mechanism. The rotation of the cartridge lock ring 114 causes rotation of the retaining posts 488. The retaining posts 488 can be rotated into either the channels for first depth 490 or the channels for second depth 492. The length of the channels for first depth 490 correspond to one of the choices of depths, and the length of the channels for second depth 492 corresponds to the other, with one or the other depths being selected by the user using buttons 409. For example, the length of channels 490 can be in the range of 20-30 mm and the length of the channels 492 can be in the range of 12-20 mm. The requirement of a user to affirmatively select a depth provides yet another interlock. Without an affirmative selection, the applicator may not allow activation/needle insertion. The rotation of the cartridge lock ring 114 is thus caused by a clockwise or a counterclockwise rotation directed by the applicator 400 according to the dictates of the user. Requiring rotational motion of a set of posts into such channels to achieve deployment of the electrodes and, if present, injection needle greatly reduces the chances for accidental discharge, even upon violent jarring or falling.

In more detail, the rotation of the cartridge lock ring 114 is transmitted to the cartridge assembly 100 by the retaining posts 488, which are disposed upon proper cartridge assembly 100 insertion into slots on an insertion mechanism gear drive ring 478. In FIG. 18A, the slots on the insertion mechanism gear drive ring 478 are disposed at 3 o'clock and 9 o'clock positions. The insertion mechanism gear drive ring 478 is mounted to a partial insertion gear ring 479, which is driven by an insertion mechanism drive motor 482. Driving the partial insertion gear ring 479 causes the insertion mechanism gear drive ring 478 to rotate either clockwise or counterclockwise. A flag 481 on a ring 480 and accompanying insertion mechanism position sensor 483 are employed to determine the position of the insertion mechanism gear drive ring 478, and is further used to accurately return the same to the 3 o'clock and 9 o'clock positions when the applicator 400 is to be re-used with another cartridge.

The above implementation provides various advantages. For example, the user has to actively perform a step of selecting the depth before proceeding with the administration procedure. In so doing, the user has to assess the proper depth of injection for the selected injection site and prepare the site as noted in a guide or instructions for use document. As noted, the insertion mechanism, requiring rotational motion to deploy, is significantly hardened against accidental deployment due to falling, dropping, jarring, and so on.

Variations are to be understood by a person skilled in the art. For example, while two channels and two retaining posts are employed for each depth, one channel and one retaining post may also be used. Various types of motors and mechanisms can be employed for conveying the rotational motion necessary to rotate the posts into the channels. Other variations are also to be understood, including the use of solenoids and the like. In lieu of the use of channels, motor driven deployment can be used to provide variable depths, which depths can be controlled simply by how far the motor is controlled to drive the deployment. Preferably, in this context, the hybrid drive mechanism described would be configured such that the impulse discharge mechanism (e.g., the spring) is used for initial deployment through the dermis and then the motor drive mechanism is used to advance the electrodes to their desired depth.

One or more interlocks can be in place which must be deactivated before the insertion mechanism gear drive ring 478 is caused to rotate, rotating retaining posts 488 into the channels.

First, a force detection interlock subsystem can be in place that requires the device to be applied to the subject at a force of greater than a predetermined amount prior to allowing the administration procedure to be initiated. This force can be measured by an appropriate mechanical or electromechanical system and the result fed back into the controller 700 and used as an interlock to prevent activation of the device where insufficient force is provided. In some embodiments, the controller 700 is capable of conveying the state of the force detection interlock to the user through visual, haptic, or auditory signals so that a state of inadequate force can be corrected and the user may proceed with administration. In the event that the user attempts to proceed with the administration in a state of inadequate force contact (e.g., by depressing a trigger 407 or other activation button), additional visual, haptic, or auditory signals can be provided by the applicator 400 or controller 700 to notify the user that the interlock must be deactivated prior to proceeding with administration.

The detection of the force applied to the subject can be accomplished in a number of ways. Referring to the particular implementation of FIGS. 4 and 8A-8B, the alignment guide/splay shield 108 is equipped with a force contact pickup 128. The alignment guide/splay shield 108 can be mechanically biased in a distal direction (towards the subject) using one or more force contact springs 126, of which four are shown in FIG. 4. The force contact pickup 128 changes its position by virtue of the force applied to the alignment guide/splay shield 108. In so doing, it also changes the state of an electrical circuit formed by the force contact pickup 128, a set of first pads 162, a set of second pads 164, and a flexible circuit 160. In particular, by testing for continuity between one or more pads 162 and one or more respective pads 164, it can be determined how far backward or proximal the alignment guide/splay shield 108 has been moved by applied force, and thus if sufficient force exists for proper delivery. The state of the circuit is read by the applicator 400 using sensor contacts 434 (see FIG. 16). If sufficient force is indicated, the force contact interlock is deactivated, allowing the user to operate the device.

In one implementation, at the first contact point, the system may not register that any particular force has been applied. At the second contact point, the system may register that it is at partial (but not sufficient) pressure. At the third contact point, the system may register that the prescribed level of pressure required to proceed with procedure administration has been achieved, and the interlock may deactivate. Preferably, the status of the force contact circuit is provided to the user via the applicator display 404.

Variations are to be understood by a skilled person in the art. For example, the force contact interlock may form an electrical lock that is deactivated either within the controller 700 or within the applicator 400 itself. In another variation the force contact circuit can be configured to provide information regarding the status of the device throughout the procedure administration. In particular, the system may include a feedback loop between the force contact circuit and the controller 700 wherein a reduction in the force applied by the user precipitates the generation of a visual, haptic, or auditory signal by the controller 700 and/or applicator 400 so that a state of reduced force can be corrected. In a certain embodiment, a feedback loop exists between the force contact circuit and the controller 700 such that the detection of a change in the applied force prompts the system to initiate a check as to whether the electrodes remain properly deployed into the tissue of the subject, e.g., via an impedance or resistance check between the electrodes. If the check is passed, then the procedure proceeds normally. In the event that the position of the electrodes is no longer acceptable, then the procedure can be aborted and the user notified of the state of the device through the generation of a visual, haptic, or auditory signal by the controller 700 and/or applicator 400. This feedback loop is of particular significance during the injection of the medicament. By monitoring the position of the device and the state of the electrodes, the feedback loop between the force contact circuit and electrode resistance/impedance monitor, the system may detect if the electrodes (and therefore the injection needle) are no longer in the subject, allowing system halt operation of the injection drive mechanism 456 to cease depressing the reservoir plunger 484 and terminating the injection of the medicament. While this embodiment is most readily implemented with a motor driven injection drive 456, other variations can be implemented in the case of manually operated or spring drive mechanisms, wherein the activation of mechanical interlocks can be used to halt actuation of the reservoir plunger following detection of a fault condition. This feature can be particularly useful in stopping the HBV vaccine from inadvertently spraying out into the environment when the applicator 400 is removed from the tissue of the subject prior to completion of a medicament delivery. For medicaments or therapeutic agents that are potentially hazardous for exposure to users or the environment, such a design may avoid inadvertent discharges/exposures.

Since the quantity of the dose delivered to the subject in a partial dose situation can be critical to inform the decision making of the clinician regarding further treatment, it is preferable that the injection drive mechanism 456 include appropriate sensor and control features to determine the position of the injection drive plunger 484 at the time the injection stroke was halted due to the detection of a fault condition or other circumstance in which halting the injection stroke is necessary. Preferably this is achieved through monitoring of the revolution count of the motor used to drive the injection drive plunger 484, but other methods for monitoring the position of the injection drive plunger 484 including optical or electrical sensors can be employed. Based on the known dimensions of the injection drive plunger 484, the depth of insertion, and the reservoir 101, the use of appropriate logic and control circuits can translate the position of the injection drive plunger into an estimate of the volume of medicament remaining in the syringe at the point at which the injection stroke was terminated. Such information can be conveyed to the user via the display 712.

In addition to providing a termination feature to terminate the injection stroke in the event that a fault condition is detected, the use of a motor injection drive 456 can also provide a supplementary detector for detection of a fault condition or other operational issue. Specifically, the incorporation of appropriate measurement and logic circuits to monitor the circuit drawn by the motor during the injection stroke can be used to confirm that the injection has been administered within defined specifications. Expected ranges for the current drawn by the motor can be established for the various stages of the injection stroke including the initial run up of the injection drive plunger 484 before it contacts the plunger stopper 159, the initial interface between the injection drive plunger 484 and the plunger stopper 159, actuation of plunger stopper 159 forward in the barrel of the reservoir 101, and conclusion of the injection stroke as the plunger stopper 159 contacts the end of the barrel of reservoir 101. By correlating the position of the injection drive plunger 484 with the measured current drawn by the motor to the expected values during each phase of the injection of the agent, the system is capable of identifying potential fault conditions and conveying them to the user. For example, if the user inadvertently inserted a reservoir 101 in which the plunger stopper 159 had been partially actuated (and therefore did not contain the full intended dose of medicament) into cartridge 100, the system could detect that the expected increase in current drawn by the motor injection drive 456 did not occur when the injection drive plunger 484 reached the outer tolerance for plunger positioning. Under this circumstance the system could terminate the administration procedure and notify the user of the detected fault. Additional fault conditions including (but not limited to) faulty components in the applicator 400, breakage of the reservoir 101, and/or a defective cartridge 100 would be potentially detectable via this method.

Another ‘interlock’ to facilitate proper execution of the administration procedure is provided by the alignment guide/splay shield 108, which is illustrated in FIG. 9C. In this figure, the alignment guide/splay shield 108 is shown with splay features 168 and a hole 170 defined therein for slidable movement of a stick shield 134. The stick shield 134 is illustrated in FIG. 9B, and electrode holes 167 are also illustrated. For transcutaneous insertion of electrodes and, where relevant, injection needles, having a consistent skin interface facilitates deployment of electrodes into the target tissue while maintaining the desired spatial relationship between the members of the plurality. In particular, proper deployment is most consistently achieved when the skin is positioned perpendicularly to the direction of deployment. In addition, misalignment of the electrodes and injection needle are reduced when the skin is placed into tension in the orientation perpendicular to the direction of deployment. As can be seen, the splay shield 108 includes mechanical features including ribs and edges to engage with the skin and place it into tension perpendicular to the direction of deployment. Combined with the force contact circuit pick up system described above which ensures a consistent force applied to the skin, the alignment guide/splay shield 108 ensures that the skin is oriented and placed under tension in the direction perpendicular to the direction of electrode deployment. While this embodiment utilizes mechanical rib features to engage the skin at the device interface, numerous other designs and features could be utilized for engagement including the use of alternative materials with a high coefficient of friction when placed in contact with skin (e.g., rubber insets, adhesive patches, and the like) or alternative mechanical features including molded textures, cut outs, and sawtooth features capable of placing the skin into tension.

As can be seen, the alignment guide/splay shield 108 has a preferential direction defined. As described above, spatial and temporal co-localization of the medicament distribution and electric field application are desirable. Notably, the inherent structural properties of skeletal muscle lead to a characteristic ellipsoid distribution pattern of intramuscular injections where the major axis of the ellipsoid aligns with the striations of the muscle fibers. For applications involving intramuscular injections, it is therefore favorable to arrange the electrodes to generate an ellipsoid electric field profile. In order to ensure that the electrode array and resultant electric field profile are properly oriented relative to the striations of the target skeletal muscle, the use of an alignment guiding feature is of particular utility for intramuscular administration. The objective of the alignment guiding feature is to facilitate placement of the device such that the orientation of the electrode array is most favorable relative to the muscle striations and the resulting medicament distribution following injection. For an arm injection, the alignment guide/splay shield 108 would desirably wrap around the arm horizontally like an arm band. A similar orientation would be desired for the leg with the splay shield wrapping around the leg horizontally. It has been found that having the alignment guide/splay shield 108 configured in this manner results in >98% accurate medicament deliveries by users even in the absence of verbal instructions. The preferred direction shown and resulting skin placement is particularly useful for intramuscular injections, because the diamond shaped array of electrodes (see the array of distal ends of electrodes 137 in FIG. 9A, which roughly matches the shape of the stick shield 134 and its associated holes 167) is then oriented properly to deliver a medicament and to cause electroporation of the medicament along the preferred muscular striation direction. A primary feature is that, when aligned properly, the skin should be flush with the skin interface where the orifice is located, e.g., where the needle emerges. In this way, a consistent interface to the skin is obtained.

Where the alignment relative to the target muscle is improper, the arc generally causes a visually evident gap, e.g., 2-5 mm, to occur between the alignment guide/splay shield 108 and the skin. The visually evident gap can be employed as a reminder to the user to reorient the applicator 400. The applicator 400 can be less stable against the skin of the subject. Alignment guide features wherein the distance between edges of the "wings" of the feature are at least 1.3 times the vertical height of the feature are preferable for facilitating proper placement. In addition, in some cases the design of the feature is such that the tissue interface can be placed flush against the skin in the desired orientation while exhibiting at least a 2 mm air gap when placed at a 90 degree angle relative to the desired orientation.

Variations on the design of the alignment guide are to be understood by a skilled person in the art. For example, instead of an arc shaped alignment guide/splay shield 108, a "V" shaped one can be used. Other variations are also to be understood with the key characteristic being that the device can be placed directly against the skin in the desired orientation whereas a visually apparent gap between the tissue interface and the skin of the recipient of 2 mm or greater is present when the device is misaligned relative to the striations of the target muscle.

Figure 9D:
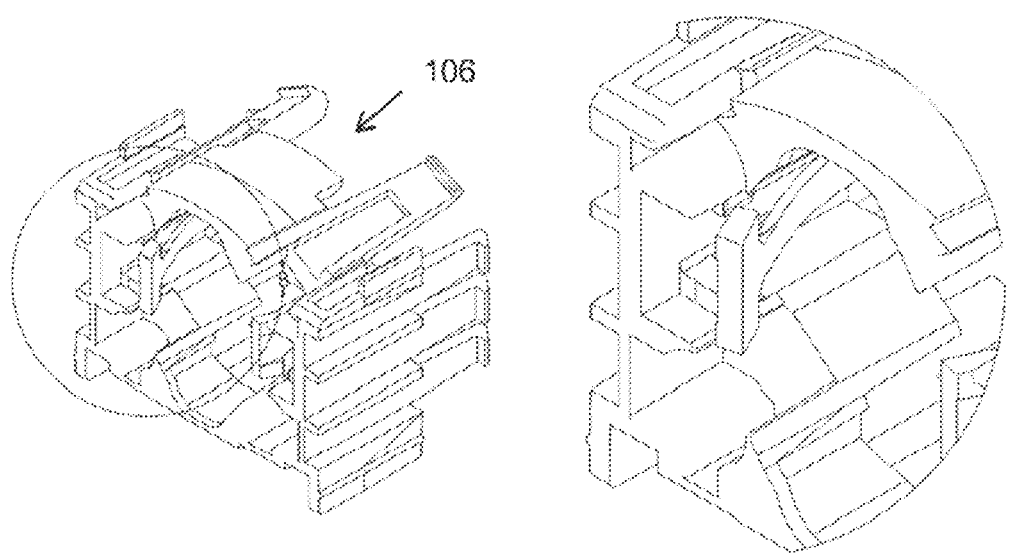

As noted above, the orientation of the alignment guide/splay shield 108 is related in some implementations to the shape of the electrode array, because the diamond symmetry of the electrode array has a certain distribution associated with it, and this distribution should bear a certain predetermined relationship to the shape of the alignment guide/splay shield 108. Referring to FIGS. 9A-9B, the electrodes, and more particularly the distal portions 137, are shown, which are four in number. The electrodes are positioned in a diamond shaped array, which can mean they have second order symmetry, i.e., are twofold symmetric, in that they can be rotated and at two different positions appear the same. The electrodes extend in this array from holes 167 defined in the stick shield 134. The use of a diamond shaped array is particularly useful because it is generally desired for intramuscular injections as discussed above. To reiterate, the second order symmetric array leads to a second order symmetric applied electric field. This type of applied electric field can have a preferred direction along the striations of the muscles if the alignment guide/splay shield 108 is oriented properly. Thus the alignment guide/splay shield 108 and the second order electric field orientation work together in a synergistic fashion to accomplish medicament propagation along the direction of muscle striation.

Broadly speaking, in a diamond shape, or other second-order symmetric shape, there is generally a major (long) axis and a minor (short) axis. The axes can bear a predetermined relationship with a preferred axis of the alignment guide/splay shield 108. For example, if the alignment guide/splay shield 108 is thought of as having wings, with the arcuate shape of the wings encircling the arm, then a line segment connecting the center of the wings can be perpendicular to the major axis of the diamond shaped array.

Variations are to be understood by a skilled person in the art. For example, while a diamond is one possible shape for an electrode array, another exemplary shape is a rectangle, which is also second-order symmetric. The electrodes can be placed into the appropriate positions but can be moved to within a predetermined or desired tolerance, e.g., within 5%, 10%, and so on. Electrodes can be in various other shapes so long as they create a second order rotationally symmetrical electric field.

In another variation, for non-intramuscular injections, other order symmetries can be used. For example, for skin, there is generally no preferred direction of medicament propagation and so even a circular array of electrodes can be employed for intradermal injections.

Other considerations of electrode arrays are as follows. The simplest array configuration comprises two electrodes connected to the opposite poles of the electrical energy source. As disclosed in U.S. Pat. Nos. 5,873,549 and 6,041,252 (incorporated herein by reference in their entirety), utilization of three or more simultaneously active electrodes arranged in a multi-element array can be used to increase target volumes of tissue and improve the uniformity in electrical field propagation within the target tissue. A wide range of geometrical electrode arrangements and activation patterns have been developed for electric field application in tissue. These include electrodes arranged in linear, rectangular, circular, or triangular configurations capable of propagating electrical fields in a volume of tissue of roughly ellipsoid, cuboid, cylindroid, or spheroid shape. Most commonly, the electrodes are arranged parallel to one another and configured for transcutaneous insertion in an orientation substantially perpendicular to the skin surface. In order to ensure that the target volume and shape of tissue is affected by the application of electrical field, it is desirable that the intended spatial relationship between each of the electrodes within the array is achieved following transcutaneous insertion. Specifically, unintended changes in the inter-electrode spacing should be avoided as they can cause changes in the magnitude of the electrical fields propagated within the target tissue, potentially leading to negative consequences for the safety and/or efficacy of the procedure.

Another interlock involves use of an exterior cartridge cap 110. In particular, the alignment guide/splay shield 108 is covered while stored with an exterior cartridge cap 110. The exterior cartridge cap 110 is configured to not just generally protect the distal end of the device until use but also to serve as an interlock feature itself. While protection of the distal end of the cartridge assembly 100 serves the purpose of protecting the needle and electrodes from the environment, a commonly-encountered problem is that users often forget to remove such caps. One solution is to make the cap a bright color that is different from the color(s) of the other components in cartridge 100, so as to notify the user of its presence and thus remind the user to remove it. Another part of this solution is to include an extension or reminder tab 190, as shown by the arcuate section adjacent a rectangular section, the arcuate section visible even when the cartridge assembly 100 is placed up against a subject. As this reminder tab 190 is visible, it can serve as a reminder to remove the exterior cartridge cap 110 even when the remainder of the exterior cartridge cap 110 is not visible.

Figure 10C:
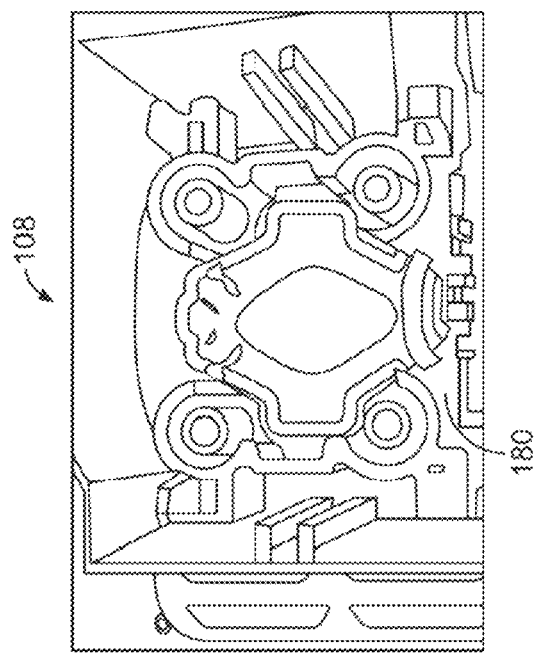
Figure 10B:
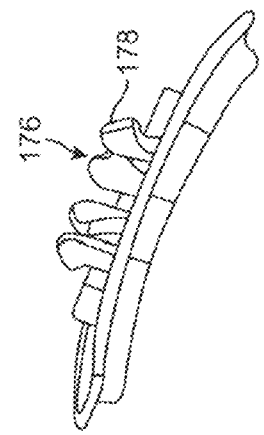
Figure 10A:
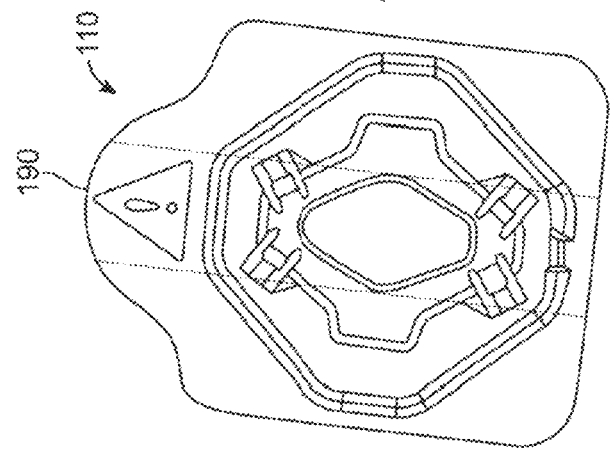
Figure 10D:
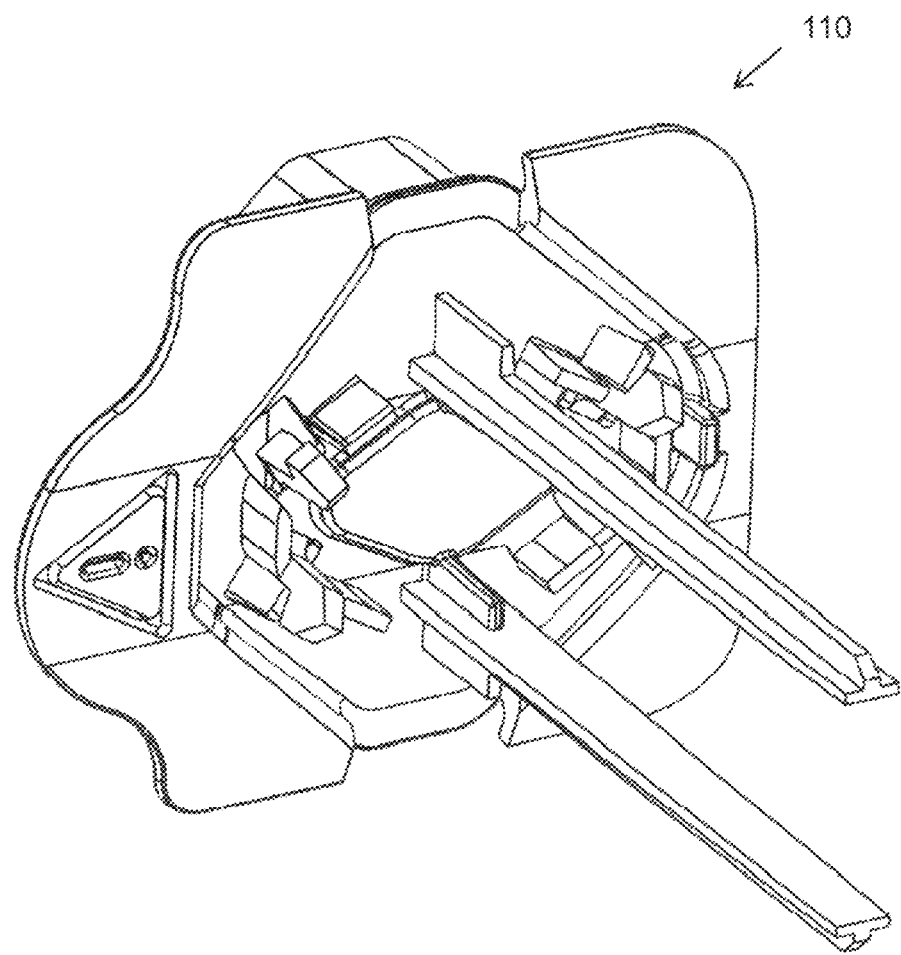
Figure 12:
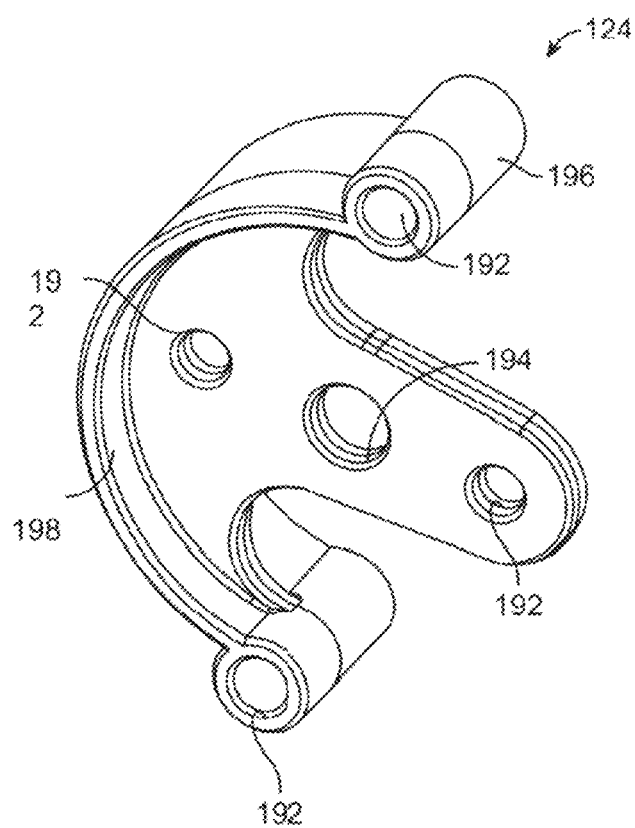
Figure 13:
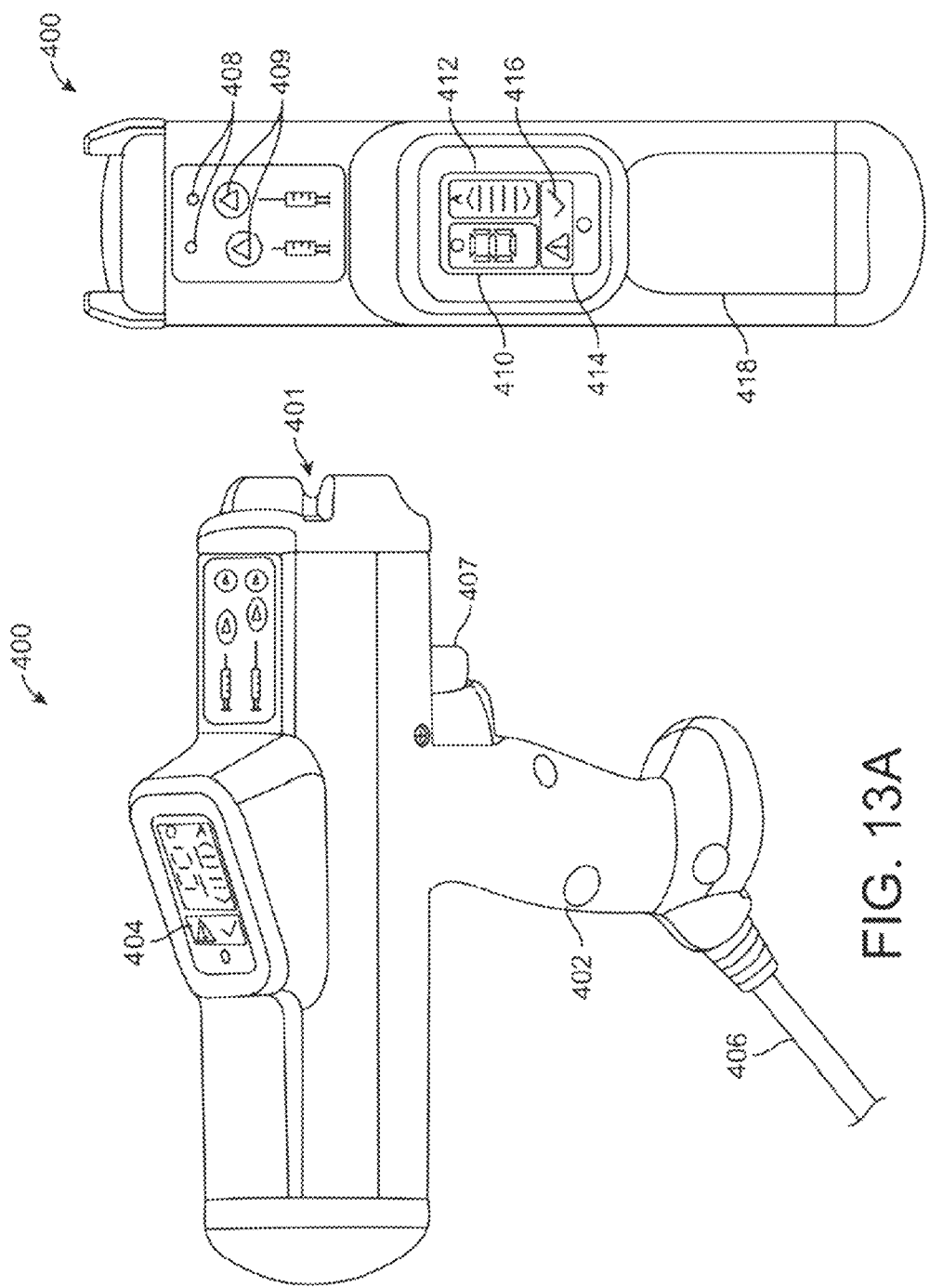

Referring in more detail to FIGS. 10A-10B, the exterior cartridge cap 110 includes an outer surface facing distally, towards the subject, and an inner surface facing the alignment guide/splay shield 108. On the inner surface are provided a number of hooks 176 which engage a corresponding wall 180 defined on the alignment guide/splay shield 108. The hooks hold the exterior cartridge cap 110 in place.

However, if the exterior cartridge cap 110 were inadvertently left in place, and the applicator 400 pressed up against an insertion site with force, the force of the alignment guide/splay shield 108 against the exterior cartridge cap 110 may tend to cause the exterior cartridge cap 110 to "pop off" by being pushed away from its hooked position by the alignment guide/splay shield 108. However, chamfered surfaces 178 are provided on the hooks 176 which tend to act against the stick shield 134 when pressure is applied, causing the hooks 176 to splay outward, increasing their retaining force against the alignment guide/splay shield 108, and preventing the exterior cartridge cap 110 from popping off. In addition, the chamfered surface acts further against the stick shield, preventing the alignment guide/splay shield 108 from moving relative to the stick shield 134. If the alignment guide/splay shield 108 cannot move relative to the stick shield 134, the force detection interlock cannot be deactivated, as the force contact pickup 128 cannot move to the third force contact point discussed above, where full pressure is detected (or for that matter even to the second force contact point). The controller can provide a report when this happens to the controller. For example, a user interface indication such as "You need to remove outer cartridge cap." can be displayed, the same caused by detection of a trigger pull performed in the absence of adequate force.

While certain interlocks have been described above, more or less interlocks can be provided in any given implementation. For example, other ways can be employed for force detection and use as triggering signals for interlocks. Other types of interlocks may also be employed, including trigger locks, safety switches, and the like. Yet other types are to be understood by one of ordinary skill in the art, given this teaching.

Once a depth of insertion is affirmatively selected by the user, and the exterior cartridge cap 110 is removed, and the proper force is detected by the force interlock, activation of the trigger causes clockwise or counterclockwise rotation of the cartridge lock ring 114, with the direction of rotation dependent on the depth of insertion selected by the user. The rotation causes the retaining posts 488 to move into the channels of selected depth, which in turn causes the needle and electrodes to deploy. In particular, the inner cartridge 103, cartridge breech 112, reservoir 101, inner cartridge cap 104, needle hub 152, needle 105, electrodes 122, and associated elements to move forward under the influence of the electrode/needle insertion spring 472. In the present embodiment, these elements are rigidly connected to each other and thus move forward as a unit.

To further minimize the risk of sharps injuries to the user, it is preferable that the cartridge assembly also incorporates a mechanism for sheathing the electrodes and any injection needles following their removal from the recipients' tissue. This can be accomplished through the incorporation of a stick shield feature that houses the electrodes and injection needle (if present) prior to their use and then extends over the electrodes and injection needle (if present) following their deployment and removal from the tissue of the subject. Commonly, the tissue contact interface comprises the distal surface of the shield feature. Although the use of manually operated shield features can be considered, preferably, the device incorporates a mechanism to automatically extend the shield feature over the electrodes and further to engage a locking feature to maintain the shield feature in the extended state once it has been removed from the tissue of the recipient. Examples include a shield feature slidably engaged with the cartridge outer housing and operatively connected to a source of stored energy, such as a spring, which slides the shield forward upon withdrawal of the electrodes from the recipients' tissue. Alternatively, the mechanism can be contained within the applicator and configured to reverse the electrode deployment step, thereby retracting the electrodes and any associated injection needles behind the tissue contact interface. This can be accomplished using simple electromechanical mechanisms for linear motion such as motors or solenoids.

In a particular implementation, and referring back to FIG. 4 as well as to FIGS. 11A and 11C, the stick shield 134 is configured to stay in position while the medicament delivery happens, but the movement forward of the inner cartridge 103 and other associated components during medicament delivery causes compression of a stick shield spring 138. This compressed stick shield spring 138 then relaxes as the applicator is removed from the subject, as the stick shield 134 is caused to move forward when the applicator 400 is removed from the subject, covering the needle and electrodes, and protecting the subject and others against the uncovered sharps. Notably, this feature also prevents the visualization of the sharps features during withdrawal, which can facilitate acceptance from subjects experiencing anxiety related to needles.

While the relaxed spring would otherwise be capable of recompressing, and in particular if the user moved the stick shield 134 proximally, it is prevented from doing so by the action of stick shield support arm 132, which are mounted to the interior of the outer cartridge 102 and which serve a ratcheting function as the stick shield 134 moves forward. In particular, and referring to FIGS. 11A and 11C, stick shield support arms 132 move over various sequential retaining walls, and can do so easily when the stick shield 134 is moving distally. However, in the proximal direction, the stick shield 134 is prevented from moving because the stick shield support arms 132 abut the retaining walls in this direction, in a ratcheting fashion, and do not allow passage.

An initial set of retaining walls 188 prevent proximal movement of the stick shield 134 prior to use of the cartridge assembly 100. A set of first depth retaining walls 184 prevent proximal movement of the stick shield 134 after discharge at a first selected depth. A set of second depth retaining walls 186 prevent proximal movement of the stick shield 134 after discharge at a second selected depth. The stick shield 134 is prevented from complete removal from the cartridge assembly 100 by the action of the stick shield retaining hooks 182 acting against the inner cartridge 103.

Variations are to be understood by a skilled person in the art. For example, in one implementation the stick shield support arms 132 can be provided by stamped metal support arms that interface with the outer cartridge 102. In some embodiments, the support arm features are directly integrated as injection molded plastic features in the outer cartridge cap 106 and/or alignment guide/splay shield 108. The specific material should be selected to achieve sufficient rigidity to provide support to the elongate electrodes while retaining sufficient elasticity to prevent fracture of the component under load. Material selection should also consider the intended method of sterilization for the electrode array (e.g., gamma radiation, steam sterilization, ethylene oxide, or e-beam) to ensure that the features retain adequate material properties following sterilization. In an exemplary embodiment, the features, as implemented, should be capable of holding the stick shield 134 against proximal movement when at least 5 N, but more preferably at least 15 N of force applied. Other ways of providing a ratcheted function to prevent proximal movement of the stick shield may also be employed including a gear rack implemented on stick shield 134 and a corresponding ratchet feature implemented in outer cartridge cap 106.

Referring to FIG. 4, each elongate electrode 122 within the array comprises a distal portion 137 and a proximal portion 135 that are in conductive communication. The distal portion is configured for tissue penetration and electric field propagation in tissue and the proximal portion is configured with a conductive contact region capable of reliably achieving conductive communication with the electrical connections contained within the applicator with a suitable source of electrical energy. The source of electrical energy can, by temporal variation in the power applied to individual electrodes, cause a spatially and temporally varying electric field within the body of the subject, generally confined to a volume around the region of medicament distribution, and the same can be used to advantage in electroporation therapy.

The relevant characteristics of the electrodes include shape, diameter, tip profile, length, material composition, and conductivity, the specifics of which are selected based on the intended application. Most commonly, the electrodes comprise electrically conductive elongate rods with a curvilinear cross section with diameter 0.1-1.5 mm. The electrodes can be solid core or hollow. Most commonly hollow electrodes incorporate one or more orifices and an operative connection to a fluid reservoir, thereby allowing for the administration of the agent of interest or other associated medicaments including anesthetics, surfactants, proteins, adjuvants, or enhancers from the electrode itself. Depending on the application, appropriate metallic electrode materials include, but are not limited to titanium, gold, silver, aluminum, copper, tantalum, tungsten, molybdenum, tungsten, stainless steel, MP35N and alloys thereof. Electrodes may also be comprised of electrically conductive ceramics or plastics. To minimize unwanted electrochemical reactions at the tissue electrode interface, it is often desirable that one or more of the electrodes are coated in a conductive material providing improved electrochemical stability compared to the electrode material itself. Such coating materials include, but are not limited to, platinum, iridium, palladium, osmium, gold, silver, titanium, and alloys thereof.

As described above, the tip of the distal portion is configured for tissue penetration. Common tip profiles include, but are not limited to, trocar, bevel, cone, blade, lance, and taper. For transcutaneous electrode deployment, tip profiles with one or more cutting edges are preferred. For certain applications where the penetrating tip profile can be undesirable for generating the required electrical fields, the tip can be comprised of a non-conductive material fixed to the distal tip of the electrode or the penetrating tip can be covered in an adherent coating or tubing comprised of a biocompatible electrically insulating material such aspoly(p-xylylene) polymer, polyolefin, polyvinyl chloride, polyurethane, polyester, polyimide, silicone rubber, thermoplastic elastomer/rubber, ethylene tetrafluoroethylene, fluorinated ethylene propylene, and/or perfluoroalkoxy plastic.

Proximal to the penetrating tip are one or more conductive regions configured for the propagation of electrical fields in tissue. In order to confine the propagation of electrical fields to the target region of tissue, commonly, especially for subcutaneous and intramuscular administration, at least a portion of the electrode length configured for penetration in the tissue is covered in an adherent coating or tubing comprised of an biocompatible electrically insulating material such aspoly(p-xylylene) polymer, polyolefin, polyvinyl chloride, polyurethane, polyester, polyimide, silicone rubber, thermoplastic elastomer/rubber, ethylene tetrafluoroethylene, fluorinated ethylene propylene, and/or perfluoroalkoxy plastic. In this way, electrodes can be configured to only activate at a particular depth within the tissue.

Collectively, the number of electrodes and their inter-electrode distance as well as the penetration depth of the electrodes and the length of their conductive region define the volume of tissue in which the electric fields is applied. These parameters are selected based on the specific objectives for the administration procedure, including target tissue site as well as the volume, dose, and viscosity of the agent to be delivered as well as the variation in skin and subcutaneous tissue thickness in the intended recipient population. Generally, for intradermal administration in human recipients, arrays comprise 2-16 electrodes of diameter 0.2-0.7 mm, an inter-electrode distance of 2-8 mm, a depth of electrode penetration of 0.5-4 mm, and a conductive length of 0.5-4 mm. Generally, for subcutaneous administration in human recipients, arrays comprise 2-8 electrodes of diameter 0.3-0.8 mm, an inter-electrode distance of 4-10 mm, a depth of electrode penetration of 5-15 mm, and a conductive length of 2-8 mm. Generally for intramuscular administration in human recipients, arrays comprise 2-8 electrodes of diameter 0.3-1.2 mm, with an inter-electrode distance of 4-12 mm, a depth of electrode penetration of 10-60 mm, and a conductive length of 2-20 mm.

In order to avoid undesirable visualization and exposure to the electrodes during the usage of the device, the cartridge assembly 100 is preferably configured such that the electrodes 122 are recessed within the device prior to their insertion into the tissue of the recipient. Most commonly, this is accomplished by providing the outer housing structure 102 slidably engaged with the electrode mount support, which in one implementation comprises an inner cartridge 103 having seems formed therein in which the electrodes are disposed. Prior to use, the electrodes are recessed within the outer housing 102. During use, the sliding engagement of the electrode mount structure, e.g., the inner cartridge 103, with the outer housing allows the electrodes 122 to slide forward relative to the distal tip of the outer housing 102, thereby deploying the electrodes 122 from the outer housing 102. The length of the sliding engagement between the electrode mount structure and the outer housing corresponds to the maximum desired depth of electrode penetration for the given application.

As can be seen in FIG. 4, and the electrodes 122 have a proximal portion 135 and a distal portion 137. The proximal portion is separated from the distal portion by a shoulder or bend 139. The shoulder or bend 139 is secured by and between the inner cartridge cap 104 and the inner cartridge 103. The shoulder or bend 139 provides a number of functions. First, while the electrodes at the distal end of the cartridge assembly 100 are required to form an array of a certain size and shape as described above, putting the electrodes 122 in the desired array size and shape at the proximal end of the cartridge assembly 100 is impractical due to the presence of the reservoir 101. In other words, the electrodes 122 have to bend "out-of-the-way" to make room for the reservoir 101. In addition, having the bend, particularly when the bend is locked in place frictionally between the inner cartridge 103 and the inner cartridge cap 104, provides a surface for the electrodes 122 to abut against when the force of the needle and electrodes insertion recoils in the distal direction as the electrodes 122 interact with the tissue during their deployment. The bend, can resistant to axial rotations, which is beneficial so that the electrodes do not exhibit significant torsional movement and rotate away from their electrical contact pads 130 (described below). In addition, in contrast to prior art techniques in which multiple electrodes interfaced with axially separated coaxial rings, requiring a different configuration for each electrode, the present system allows a common electrode type to be used for all four electrodes.

Systems and methods according to present principles provide for the propagation of an electrical field in the skin, subcutaneous tissue, and/or skeletal muscle of a recipient which facilitates the intracellular delivery of an HBV vaccine within said recipient's tissue. In this aspect, the apparatus includes two or more elongate electrodes 122 arranged in a predetermined spatial relationship and configured for deployment into the target tissue in which the agent of interest has been or is to be distributed. The desired enhancement in agent activity is contingent on achieving co-localization of the site of agent distribution with the propagation of electrical fields of sufficient magnitude to induce the desired physiological effects. Therefore it is desirable that the apparatus consistently achieve electrode deployment to the target depth and with specified intraelectrode spacing. Specifically, this ensures that the electrical fields are propagated at the proper tissue site, and, since the magnitude of the electrical fields propagated within the tissue is a function of the intraelectrode spacing, a safe and effective electric field intensity. However, the variation in the thickness, density, and composition of skin and subcutaneous tissue between sites in a given recipient and across recipient populations can lead to significant variation in electrode deployment characteristics. For example, recipients with increased thickness of skin are at increased susceptibility for electrode distortion and/or insufficient depth of penetration which can affect co-localization with the site of agent distribution.

Systems and methods according to present principles further facilitate consistent transcutaneous insertion of electrode arrays comprising 2-16 electrodes of diameter 0.2-1.3 mm with an inter-electrode distance of 2-12 mm, and a depth of electrode penetration of 0.5-60 mm in recipients with skin of heterogeneous thickness, composition, and condition. In order to permit transcutaneous insertion, tissue penetrating electrodes are most commonly elongate and configured with a tissue penetrating tip and a tissue contact region in the distal portion and an electrical contact region in the proximal portion. Given their elongate configuration, they are susceptible to bowing, bending, and/or buckling (collectively termed distortion) when subjected to the compression forces generated during transcutaneous insertion into the recipient. Such distortions during electrode insertion are undesirable as they can lead to improper electrode insertion characterized by insufficient depth of penetration and/or excessive changes in intraelectrode spacing. Of note, humans and animals exhibit significant intra- and inter-species differences in the thickness, composition, and condition of skin, any of which can have significant impact on the forces which the electrodes are subjected to during transcutaneous insertion. In some embodiments, devices for transcutaneous insertion of elongate electrodes are designed to withstand the forces present under the most stringent conditions of electrode insertion that is to be encountered in the target population of recipients. The occurrence of electrode distortion can be partially mitigated by electrode material selection as well as reducing the length and increasing the diameter of the electrodes within the array. However, material selection can be constrained by issues of performance, cost, manufacturability, and biocompatibility. In addition, electrodes of reduced length may preclude adequate coverage of a target population with heterogeneous tissue thickness while larger diameter electrodes are associated with increased discomfort and tissue trauma. Thus, the disclosure is designed to provide methods and apparatus to facilitate the transcutaneous insertion of electrodes independent of these variables.

In a first embodiment of the disclosure the subassembly cartridge housing the electrode array incorporates one or more support dynamic support members in physical contact with one of the electrodes during tissue insertion and configured to constrain movement of the electrodes perpendicular to the direction of insertion and maintain the desired spatial relationship between the electrodes. For example, and referring to FIG. 12, an electrode support feature 124 is illustrated in which holes 192 are provided for electrodes and a hole 194 is provided for passage of the needle. The tendency of the elongate electrodes to distort or buckle under load is exacerbated by any bending, eccentricity, or bowing of the electrode that may have been introduced during manufacture or assembly. Thus, it is advantageous to employ a device such as the electrode support feature 124 to constrain the electrodes to prevent, or correct, any bending, eccentricity, or bowing they might exhibit at rest, and to prevent unwanted perpendicular motion of the electrode as a result of the loading that occurs during deployment into tissue.

In the context of the disclosure, a dynamic support member is defined as a structural element which provides sliding engagement with the elongate electrodes during insertion into the tissue of the recipient and which is configured to undergo a change in position, size, and/or conformation during electrode insertion in order to maintain the desired spatial relationship of the electrodes as they are deployed to the target tissue depth. Since the electrodes are subjected to the largest loading forces at the initial contact with the skin, the engagement of the dynamic support member with the electrodes comprising the array is preferably affected prior to initial contact with the tissue of the recipient and to continue to provide support as the electrodes deploy to the full depth of penetration. It is also favorable that the dynamic support member be designed to provide support to the electrodes and injection needle while minimizing losses in electrode penetration force due to friction.

While the primary function of the dynamic support member is to maintain the desired spatial relationship of the plurality of the electrodes within the array relative to one another and to the injection needle, it is also desirable for the design of the dynamic support member to include features capable of stabilizing the array as a whole. This is preferably accomplished by providing additional structural support features which constrain lateral movement of the support member. In a certain embodiment, these support features are integrated into a sharps protection shield, which also serves to protect the user against accidental exposure to the electrodes and/or injection needle. Disclosed below are various embodiments of dynamic support members consistent with the disclosure.

An embodiment of the disclosure, described above as electrode support feature 124, involves the use of a planar support structure 124 positioned perpendicularly relative to the elongate orientation of the electrodes. The planar support structure is configured with one or more apertures 192 which correspond to the positions of said electrodes in their specified spatial relationship. The size, shape, and position of the apertures are configured to allow the support structure to slide smoothly along the elongate length of the electrodes within the array while constraining unwanted motion perpendicular to the direction of electrode deployment. Commonly, the apertures can be configured as holes or slots 192 in the planar structure with adequate clearance for the electrode (at least 10% larger than the largest cross section of the electrode, including any coatings or other adherent materials). However, if more substantial support is required for specific electrodes, one or more of the apertures may comprise tubular structures 196 arranged perpendicularly to the planar support structure. Apertures comprising such tubular structures increase the surface area contacting the electrode and thereby increase the support provided to the elongate electrodes. The planar support structure can be made from any material with appropriate structural characteristics including metal, polymer, ceramic, or composite materials and can be formed, machined, molded, or produced with other methods. To avoid unwanted electrical interactions with the electrodes, it is preferable that the interface between the electrodes and the planar support structure is not electrically conductive. The material and manufacturing method should also be selected to minimize the amount of friction at the interface between the electrodes and the dynamic support member. Due to a number of factors including their low cost, ease of manufacturability, and favorable electrical properties, the electrode support structure is commonly made of a thermoplastic such as polycarbonate, polystyrene, polypropylene, acrylic, or polyethylene. The specific material should be selected to achieve sufficient rigidity to provide support to the elongate electrodes while retaining sufficient elasticity to prevent fracture of the component under load. Material selection should also consider the intended method of sterilization for the electrode array (e.g., gamma radiation, steam sterilization, ethylene oxide, or e-beam) to ensure that the dynamic support member is compatible. The specific dimensions and design of the support structure depend on the properties of the selected material. However, it is desirable to minimize the dimensions of the support structure so that it does not excessively limit the distance that the electrodes can be deployed or to interfere with other functional properties of the device. Rigid planar structures of 0.5 mm-2 mm thickness are typically sufficient Another embodiment of a dynamic support member is the use of a compression spring with apertures accommodating the electrodes and constraining their lateral movement. The compression spring can be made from metal, polymer, or elastomeric materials, and can be formed, machined, molded, or produced with other methods. At rest, the spring is uncompressed or minimally compressed with the electrodes inserted into the apertures along the spring's length. As the electrodes are deployed, the spring compresses in the direction of deployment, with the apertures accommodating the sliding movement of the electrodes perpendicular to the spring coils. This embodiment is of particular utility when combined with a shield or sheath used to house the penetrating electrodes/needles following removal from the tissue site. In these embodiments, the force imparted to the spring by the forward deployment of the electrodes can be used to deploy a sheath or shield over the electrodes as the device is removed from the tissue.

In the implementation of FIG. 4, the stick shield spring 138 can be used to partially support the electrode support 124, and in particular the radius of the spring can be configured to match (or be just slightly greater than) the radius of the wall 198 of the electrode support 124. In this way, the electrode support 124 can be inserted into the middle of the stick shield spring 138 during use. The electrode support 124 may then slide within the interior of the stick shield 134. By being placed in the center of the spring, the electrode support 124 naturally maintains a position in the center of the spring, which provides a desired "halfway point" for support of the electrodes, roughly halfway between their point of support at the inner cartridge cap 104 and their point of penetration at the tissue interface.

Other spring-based electrode supports are contemplated. For example, a formed compression spring is positioned in the region of the electrodes, to provide adaptive electrode support. Formed compression springs can be shaped and proportioned to conform closely to the relative positions of the electrodes, in order to restrict their lateral motion. An optional biasing element can be positioned in conjunction with a formed compression spring, and may serve to bias the electrodes outward against formed compression spring. Formed compression springs can be made from metal, polymer, or elastomer materials, and can be formed, machined, molded, or produced with other methods. The biasing element can be made from metal, polymer, or elastomer materials, and can be formed, machined, molded, or produced with other methods.

Electrode supports based on other mechanisms are also contemplated, for example telescoping tubes. Telescoping tubes serve to support electrodes during insertion into the subject. The telescoping tubes can be sized to move freely relative to each other, or can be sized to move only when an axial force is applied to them.

Other support structures are contemplated, for example support structures based on movable, flexible, or pivoting support members. Lateral support members can attach to the electrodes at optional hinge features. Lateral support members can be formed integrally with the structure housing the electrodes or can be separate components attached by conventional methods (snaps, welding, adhesives, fasteners, etc.).

Another embodiment is the use of a compressible matrix material in which the electrodes are embedded. As the electrodes are deployed, the material compresses in the direction of deployment, providing lateral support along the direction of travel. Examples of compressible matrix materials include cellulose, foamed plastic or rubber polymers such as microcellular plastics, foamed silicone or foamed polychloroprene, or carbon foam matrices. Since the materials are designed to contact the electrodes and/or injection needle (if applicable), the materials should be selected to be compatible with indirect tissue contact.

The above described structures thus support transcutaneous deployment of a plurality of elongate electrodes at tissue depths of up to 60 mm while maintaining the desired spatial relationship among the plurality of electrodes and, in specific embodiments, the orifice of a hypodermic injection needle. Such support members engage the plurality of elongate electrodes during transcutaneous insertion, and constraining deflection of the electrodes in one or more directions perpendicular to their elongate orientation. Another aspect of the disclosure provides methods and apparatus for utilizing the application of biocompatible lubricious compounds to the surfaces of the plurality of electrodes in order to reduce the applied force required to achieve consistent transcutaneous deployment of a plurality of elongate electrodes to depths of up to 60 mm. In an exemplary embodiment, biocompatible silicone compounds such as Dow Corning 360 Medical Fluid or Dow Corning MDX4-4159 can be applied by conventional spray or dip coating to the plurality of electrodes comprising the array in order to improve the insertion characteristics of the electrodes. The specific selection of the coating and application conditions, such as coating method and thickness depends on the number, size, composition, and tip configuration of the electrodes as well as the target tissue in which the electrodes are deployed.

Figure 7A:
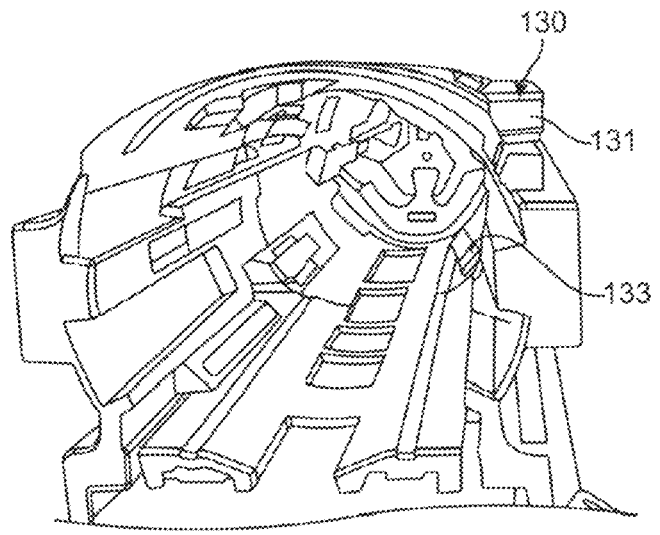
Figure 7B:
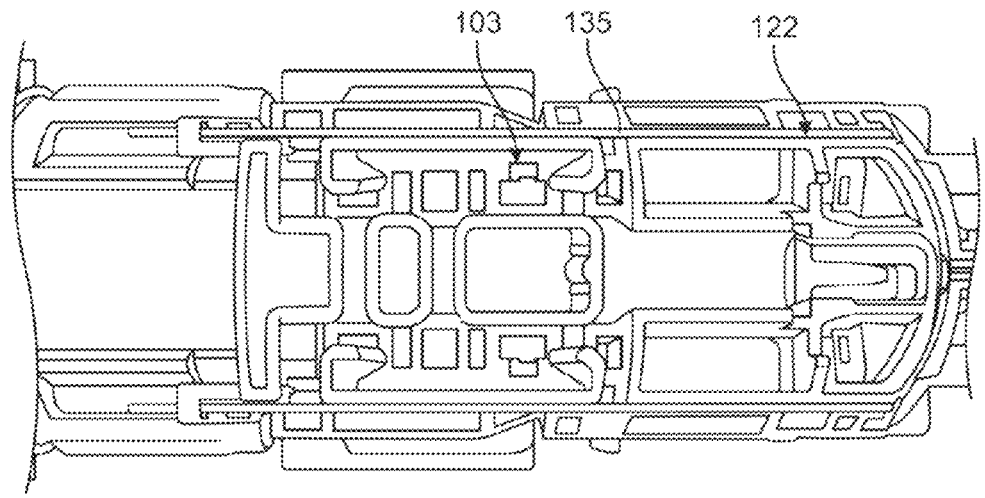
Figure 8A:
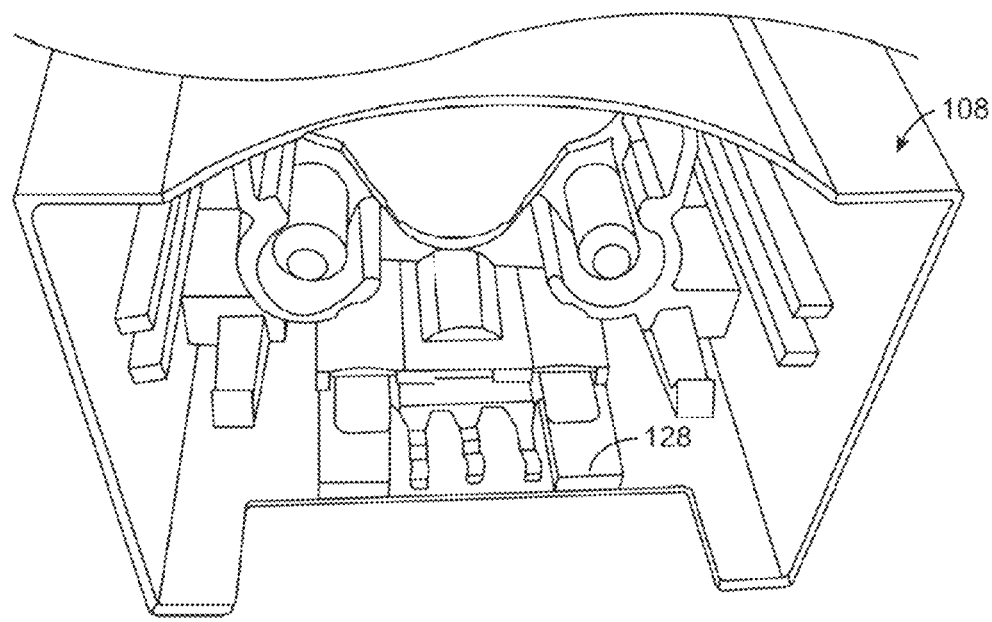
Figure 8B:
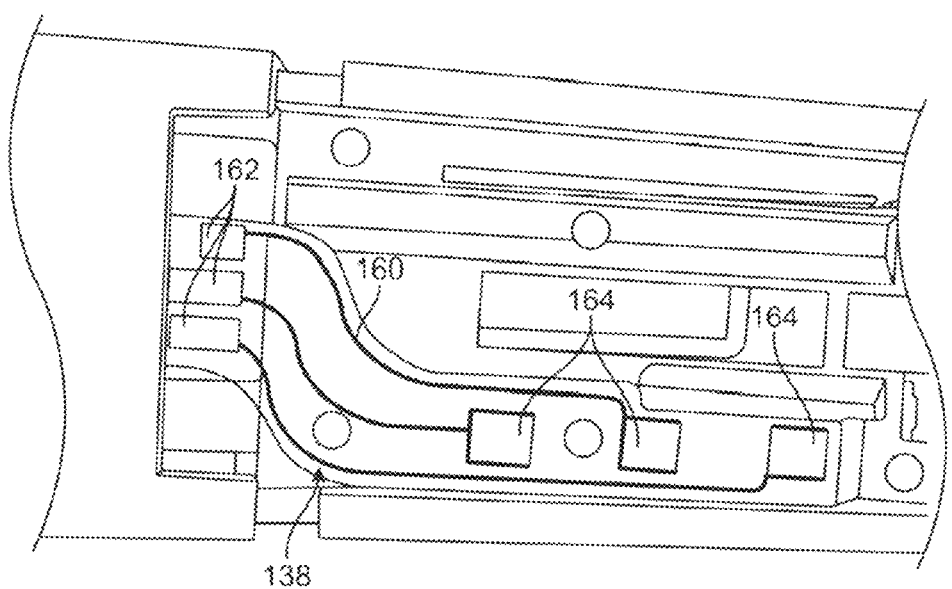

Referring to FIGS. 4 and 7A-7B, the proximal portions 135 of the electrodes 122 can be positioned on the exterior of the inner cartridge 103 of the cartridge assembly 100 (FIG. 7B). In this way, when the inner cartridge 103 is slidably disposed within the outer cartridge 102 (FIG. 7A), the proximal portions 135 contact corresponding electrode contacts 130, and in particular outer cartridge interior portions 133 of the electrode contacts 130, these interior portions 133 configured for power communication with the proximal portions 135. Due to the length of the proximal portions 135, and the length of the outer cartridge interior portions 133, the electrical communication can be made at a number of locations along their continuous interface, no matter the longitudinal position of the inner cartridge with respect to the outer cartridge. The electrode contacts 130 further include outer cartridge exterior contacts 131, configured for power communication with corresponding connections 496 on the applicator 400 (see FIG. 18C). The electrode contacts 130 are comprised of a conductive material sufficient to convey an electrical signal. In certain embodiments, the design and material selection ensure that the contact provide for adequate engagement to ensure an electrically conductive interface with the corresponding electrode over the range of expected manufacturing variation in electrode and contact position while not inhibiting or interfering with the forward travel of the electrodes 122 mounted on the inner cartridge 103. The design must also permit this engagement to persist when exposed to the expected storage conditions over the labeled shelf life of the product. In a certain embodiment, electrical contacts 130 are made of stamped or formed metal with appropriate temper to faciliate engagement with the electrode and may include coatings such as gold or copper to ensure the integrity of the electrical contacts and avoid corrosion. In addition to ensuring that electrical contact can be maintained with the electrodes at a number of locations along their continuous interface, the incorporation of the electrode contacts into outer cartridge 102 in this configuration ensures that any wear due to the sliding interaction between the electrodes 122 and the electrode contacts 130 occurs within the cartridge 100 designed for single use, thereby allowing for a static interface between the outer cartridge contacts 131 and applicator electrical contacts 496 which minimizes potential mechanical wear on the electrode connections 496 of the applicator designed for multiple uses. This configuration has the benefit of extending the useful functional life of the multi-use applicator.

Remaining portions of the applicator 400 are now described. These portions are generally those that are independent of operation with the cartridge assembly 100. Referring first to FIG. 13A, the applicator 400 includes a handle 402 and a multi-conductor cable 406 designed to carry power and control signals as well as the electrical signals to be applied to the tissue. The cable 406 is generally terminated in a connector with a corresponding connector interface in the controller 700. The applicator 400 further includes a user interface 404, in which aspects of the procedure can be viewed by the user, and in which the user can direct the applicator to perform various functions, in particular, depth selection. The applicator 400 further includes a procedure activation trigger 407, which is used by the subject to initiate the procedure.

Referring in addition to FIG. 13B, the applicator 400 includes a procedure countdown timer 410, which informs the user of the remaining duration of the procedure, and further impliedly indicates to the user that they should not remove the applicator 400 from the subject until such time as the countdown trigger has counted down to zero. A power indicator 418 is provided to indicate a satisfactory and powered connection with the controller 700. A procedure fault indicator 414 is provided to indicate to the user if a fault has occurred, e.g., one of the interlocks described above has not been deactivated. An application placement indicator 412 is provided to inform the user if a proper pressure has been obtained against the tissue of the subject, allowing the procedure to commence.

Figure 14:
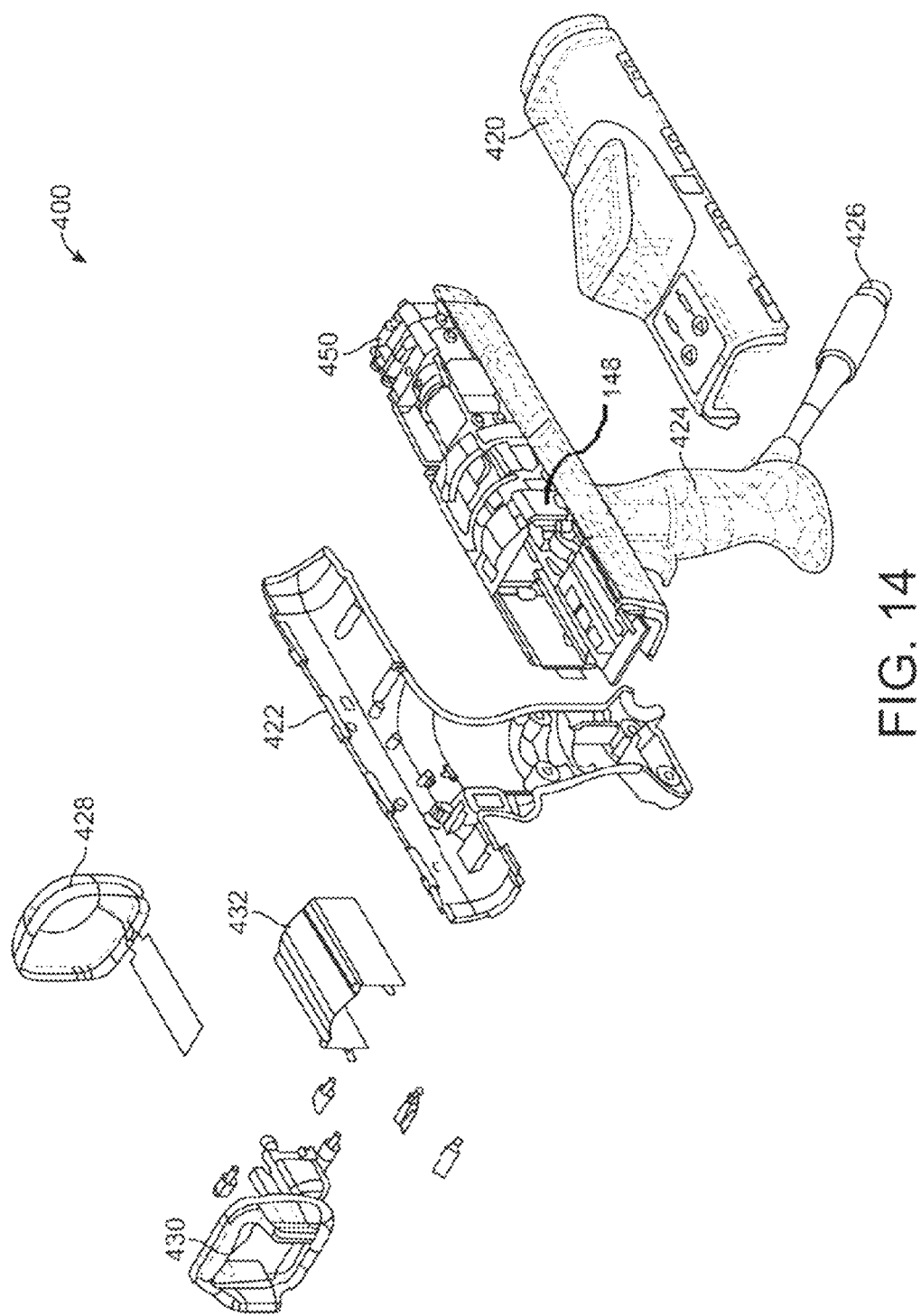
FIG. 14 is an exploded view of an applicator 400 according to present principles.

FIG. 14 indicates a number of structural components of the applicator 400, including a connector 426 (not to scale) for connection to the controller 700, a top housing 420, side housings 422 and 424, and an inner protective shell 432. A front cap 430 is provided, along with an end cap 428. Various electromechanical subassemblies 450 are also provided, several of which have been described above.

Figure 15:
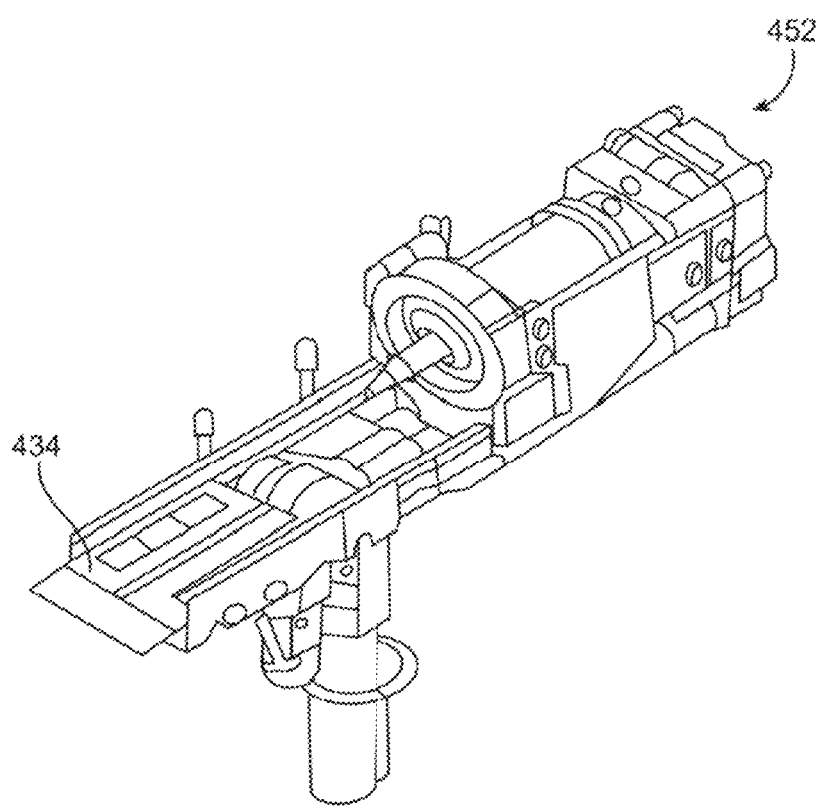
FIG. 15 shows details of a side housing and electroporation electrode connection 496 of an applicator 400 according to present principles.

FIG. 15 illustrates a more detailed view of the applicator 400, indicating cartridge pressure sensor contacts 434 and subassemblies 452 corresponding to the cartridge loading, electrode insertion, and injection functions as well as the associated sensors.

Figure 16:
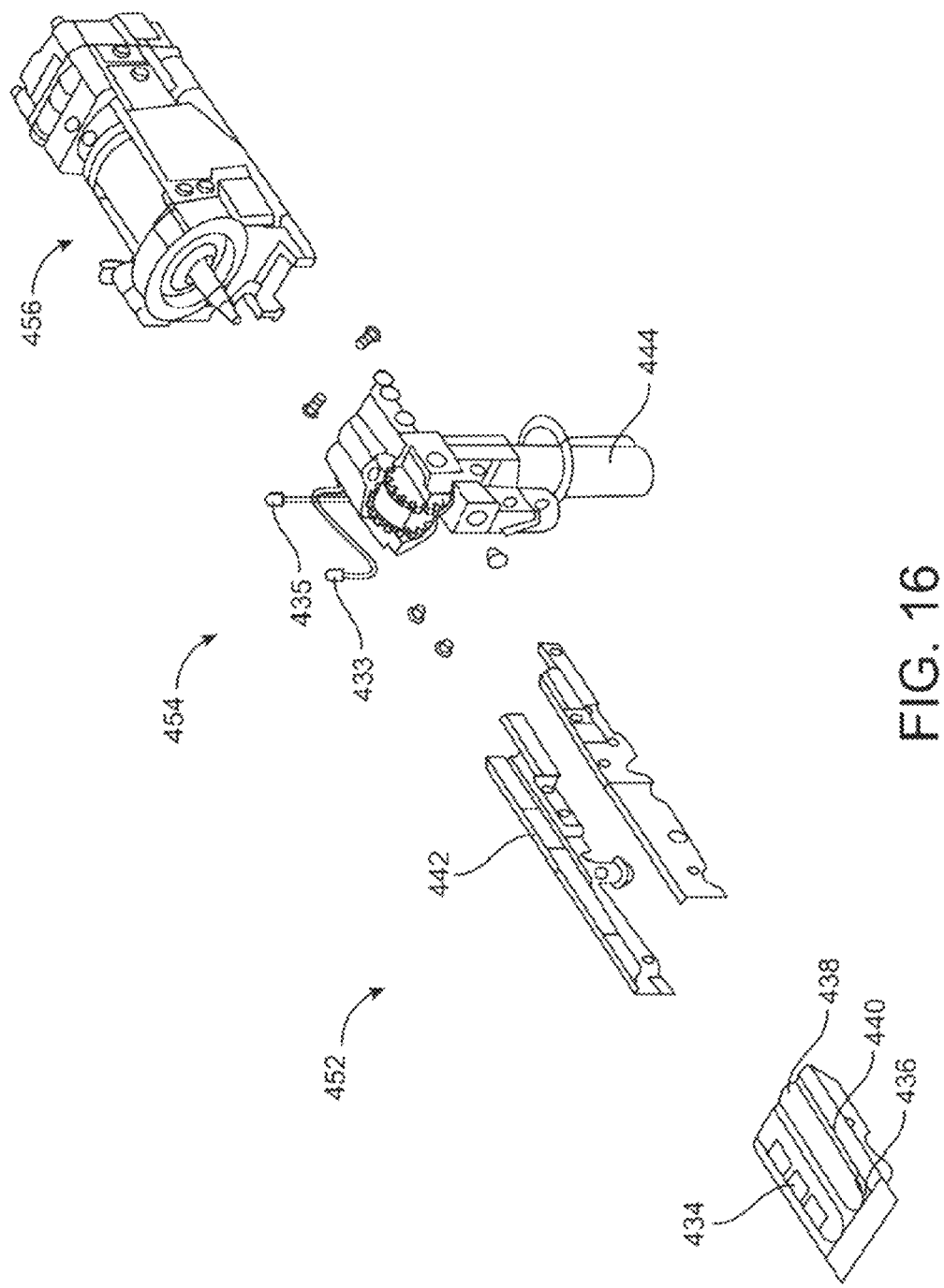
FIG. 16 is an exploded view of an applicator according to present principles, showing a cartridge loading subassembly 456.

FIG. 16 illustrates a more detailed view of the group of subassemblies 452, including the loading drives subassemblies 454 and the cartridge loading subassembly 456. The operation of the subassemblies has been described above.

FIG. 17A illustrates a more detailed view of the loading drive subassembly 454, the general to operation of which has been described above. Here it is noted that the loading is triggered by a flag on the cartridge assembly 100, and that detection of the flag leads to the system being triggered at switch 464. The loading drives subassembly is mounted to the applicator housing using brackets 466 and 468. The action of the motor 444 is transmitted to the pinion gear assembly 448 by the motor drive shaft 462.

FIG. 17B illustrates a more detailed view of the insertion/injection drive assembly 456. Many of these components have been described above. Here it is noted that the operative components are mounted to the applicator housing by a mounting bracket 476. Following insertion of the electrodes 122 and the needle 105, the plunger of the needle 105 is depressed by the injection drive plunger 484, whose action ejects the medicament from the orifice of the needle. The injection drive plunger is driven by an injection drive motor and gear assembly 486.

Generally the injection drive plunger, driven by the injection drive assembly 486, moves forward until such point at which it can no longer move forward, i.e., distally, indicating that it has reached the end of each stroke. This indication is generally given by the current used in the injection drive motor 486 rising substantially, indicating that the reservoir plunger has reached the end of the reservoir and that the injection has been completed. However, in some cases, the number of turns of the motor can be employed to determine how much medicament has been delivered. Such a feature could be used to support metered dosing of medicament or in order to notify the user in cases where the volume of delivery was not within the expected total, e.g., where the full volume of reservoir 101 was expected to be injection, but based on the position of the plunger rod, it was not emptied. These situations may arise where the user failed to hold the applicator 400 against the body of the subject until the procedure was completed, e.g., until the countdown timer had counted down to zero. As noted above, in a mid-procedure timeframe, where the force against the subject is no longer being detected, an impedance check can be performed to determine if the electrodes are still within the subject. If they are not, then it can be presumed that the applicator was prematurely removed, and a signal can be sent to the injection drive motor 486 to cease injection, limiting the amount of medicament ejected outside of the subject.

Referring to FIG. 19, the controller system/assembly 700 can be seen including an electrical field controller/generator 750 and a handle 702 and an applicator cradle 706. The controller can be configured for both table top as well as cart mounted use. In the cart mounted configuration it is the inclusion of a storage bin 704 is favorable. Details of the controller in the cart mounted configuration are shown in FIGS. 20A-20D, including wheel locks to secure the controller assembly against movement in an operational setting, a tray 710 for placing supplies including subject preparation supplies, reservoirs/vials/syringes, and so on. An applicator connector port 708 is illustrated to connect the applicator 400 to the controller assembly 700. A display 712 displays status of an administration procedure, particularly with regard to the IFU attached.

A cartridge eject button 714 is provided to cause ejection of the cartridge assembly 100 from the applicator 400. Menu navigation buttons 716 allow navigation and manipulation of components as seen on the display 712. A mute button 718 is provided to mute alerts or other audible indicators if desired. A power button 722 is provided to power the unit, and the same is activatable if the main power switch 726 (FIG. 20D) has been turned on.

The display also includes a battery indicator 720, which provides an indication of battery level where a battery backup system is provided. Such a battery backup system can be included in the controller/generator 750 to accommodate situations in which power loss prevents a main power source from powering the unit. Such may also be employed as a backup where a procedure has been started under main power, but where a main power loss has been encountered. In this case, logic and control circuitry is implemented to provide for essentially seamless transition from mains to battery power so that the procedure can be finished using the battery backup. It is favorable for the controller to include battery monitoring circuitry that is capable of monitoring whether the battery has sufficient charge to complete the procedure following loss of mains power. In some embodiments, the controller also includes display to notify the user in the event that the current charge status of the battery is not sufficient to complete the procedure in the event of mains power loss.

Referring to FIG. 20D, in which a rear view of the controller 750 is illustrated, the same can be seen to include a USB port 724, a main power switch 726, and a main power input 728.

Referring to FIG. 21, in one method of use, as illustrated by the flowchart 800, the controller/generator 750 is powered and its program automatically started (step 802). The applicator is connected (step 804), and an indication or instruction to the user to perform this action can be displayed on the display screen 712, if the applicator has not already been connected. The system may perform a self test (step 806), the self test not only ensuring proper operation of the controller/generator 750 but also ensuring correct connection of the applicator 400 to the controller/generator 750.

The program may cause the display screen to provide instructions to the user on preparation of the site of administration (step 808). This step may include ensuring that the correct medicament agent is being delivered, that the same is not expired, that contraindications have been reviewed, and that warnings/precautions have been followed.

The user then removes the reservoir cap and inserts the reservoir 101 in the cartridge assembly 100 (step 810). In some embodiments, the user experiences an audible, tactile, or haptic click (step 811) indicating proper placement of the reservoir in the cartridge assembly.

The user then inserts the cartridge assembly 100 into the applicator 400 (step 816). An error status is then tested for (step 818), e.g., for proper reservoir placement, and if one is detected, the procedure is stopped, an error message is displayed, and the user is instructed to take remedial action. If the error state can be corrected, e.g., the user has inserted the reservoir improperly but not engaged or closed the cartridge breech, then the user can be instructed to remove the cartridge and reinsert the reservoir properly (state 820). In some cases, the cartridge is automatically ejected, and in other cases the user may have to push the "cartridge eject" button to accomplish the same. In other error states, e.g., where the cartridge breech has been closed, the user can be instructed to use a new cartridge.

In any case, once the device set up is completed and a "no error" state has been achieved, the user can proceed to administration of the medicament and electroporation therapy (step 822).

The primary function of the controller is to generate the electrical fields required to achieve the desired delivery of the medicament, to control the operation of the system during set up and use, to monitor the state of the system during set up and use, and to convey the state of the system to the user during set up and use. In some embodiments, the controller is capable of providing recommendations and instructions for use of the device both in the context of user training as well as during resolution of fault conditions during ordinary usage.

The controller system and controller method of operation can be fully implemented utilizing any number of computing devices including microprocessors, microcontrollers, programmable logic controllers. Typically, instructions are laid out on computer readable media, generally non-transitory, and these instructions are sufficient to allow a processor in the computing device to implement the method of the disclosure. The computer readable medium can be a hard drive or solid state storage having instructions that, when run, are loaded into random access memory. Inputs to the application, e.g., from the plurality of users or from any one user, can be by any number of appropriate computer input devices. For example, users may employ a keypad, keyboard, mouse, touchscreen, joystick, trackpad, other pointing device, or any other such computer input device to input data relevant to the calculations. Data may also be input by way of an inserted memory chip, hard drive, flash drives, flash memory, optical media, magnetic media, or any other type of file—storing medium. The outputs can be delivered to a user by way of a video graphics card or integrated graphics chipset coupled to a display that maybe seen by a user. Alternatively, the system may output one or more formats of electronic document or a printer can be employed to output hard copies of the results. Given this teaching, any number of other tangible outputs is also be understood to be contemplated by the disclosure. For example, outputs can be stored on a memory chip, hard drive, flash drives, flash memory, optical media, magnetic media, or any other type of output. It should also be noted that the disclosure can be implemented on any number of different types of computing devices, e.g., personal computers, laptop computers, notebook computers, net book computers, handheld computers, personal digital assistants, mobile phones, smart phones, tablet computers, and also on devices specifically designed for these purpose. In one implementation, a user of a smart phone or wi-fi—connected device downloads a copy of the application to their device from a server using a wireless Internet connection. An appropriate authentication procedure and secure transaction process may provide for payment to be made to the seller. The application may download over the mobile connection, or over the WiFi or other wireless network connection. The application may then be run by the user. Such a networked system may provide a suitable computing environment for an implementation in which a plurality of users provide separate inputs to the system and method. In the below system where control of an applicator is contemplated, the plural inputs may allow plural users to input relevant data at the same time.

TABLE OF ELEMENTS

| REF # | PART |
|---|---|
| 100 | Cartridge assembly |
| 101 | Reservoir |
| 102 | Outer cartridge, aka housing |
| 103 | Inner cartridge |
| 104 | Inner cartridge cap |
| 105 | Needle |
| 106 | Outer cartridge cap |
| 108 | Alignment guide/splay feature |
| 110 | Exterior (safety) cartridge cap |

-continued

TABLE OF ELEMENTS

| REF # | PART |
|---|---|
| 112 | Cartridge breech |
| 114 | Cartridge lock ring |
| 116 | Reservoir detection spring |
| 118 | Reservoir detection cap |
| 120 | Reservoir interlock, aka reservoir insertion trigger |
| 122 | Electrodes |
| 124 | Electrodes support |
| 126 | Force contact springs |
| 128 | Force contact pickup |
| 130 | Electrode contacts |
| 131 | Exterior Outer cartridge electrode portions for coupling to applicator |
| 132 | Stick shield supports |
| 133 | Interior Outer cartridge electrode portions for coupling to inner cartridge |
| 134 | Stick shield |
| 135 | Proximal Inner cartridge electrode portions for coupling to outer cartridge |
| 137 | Distal Inner cartridge electrode portions for tissue insertion |
| 138 | Force contact flexible circuit |
| 139 | Electrode shoulder or bend |
| 140 | Reservoir loading port |
| 142 | Reservoir containment volume |
| 144 & 144' | Reservoir lockout holes ($1^{st}$ or $2^{nd}$ set) |
| 146 | Optical line of sight |
| 148 | Insertion detector, e.g., emitter/collector IR sensor within applicator |
| 150 | Inner cartridge containment volume |
| 152 | Needle hub |
| 154 | Rack |
| 156 | Egress port |
| 158 | Reservoir cap |
| 159 | Plunger stopper |
| 160 | Flexible circuit |
| 162 | First set of pads |
| 164 | second set of pads |
| 166 | Stick Shield nubs |
| 167 | Stick shield holes |
| 168 | Splay feature |
| 170 | Alignment guide hole for stick shield |
| 172 | Initiating flag |
| 174 | Continuing flag |
| 176 | Exterior cartridge cap hooks |
| 178 | Exterior cartridge cap chamfer surfaces |
| 180 | Hook engaging wall of alignment guide/splay shield 108 |
| 182 | Stick shield retaining hooks |
| 184 | First depth retaining wall |
| 186 | Second depth retaining wall |
| 188 | Initial or rest retaining wall |
| 190 | Reminder tab |
| 192 | Electrode support feature electrode holes |
| 194 | Electrode support feature needle hole |
| 196 | Electrode support feature electrode hole support structure |
| 198 | Electrode support feature wall |
| 400 | Applicator |
| 401 | Applicator cartridge assembly receiving port |
| 402 | Handle |
| 403 | Cartridge assembly receiving volume, which is defined by a housing |
| 404 | User interface |
| 406 | Multi-conductor cable |
| 407 | Trigger |
| 408 | Injection depth selection indicator(s) |
| 409 | Injection depth selection button(s) (could be toggle or other forms in another implementation) |
| 410 | Procedure countdown timer |
| 412 | Application placement indicator |
| 414 | Procedure fault indicator |
| 416 | Procedure complete indicator |
| 418 | Power indicator |
| 420 | top housing |
| 422 | First side housing |
| 424 | Second side housing |
| 426 | Electrical connector |
| 428 | End cap |

-continued

TABLE OF ELEMENTS

| REF # | PART |
|---|---|
| 430 | Front cap |
| 432 | Inner protective shell |
| 433 | Electrical contacts for motor drive 444 |
| 434 | Cartridge force sensor contacts |
| 435 | Connectors for switch |
| 436 | Cartridge loading sensor |
| 438 | Cartridge loaded sensor |
| 440 | Guide or track |
| 442 | Cartridge guide rails |
| 444 | Loading drive motor |
| 446 | Motor trigger connector |
| 448 | Pinion gear assembly |
| 450 | Electromechanical subassemblies |
| 452 | Cartridge loading, electrode insertion, and injection subassemblies |
| 454 | Loading drive subassembly |
| 456 | Cartridge loading subassembly |
| 462 | Motor drive shaft |
| 464 | System trigger switch |
| 466 | gear cover bracket |
| 468 | Mounting bracket |
| 470 | Spring cover/cartridge interface |
| 471 | Spring cover hole |
| 472 | Electrodes/needle insertion spring |
| 474 | Insertion gear bushing |
| 476 | Mounting bracket |
| 478 | Insertion mechanism gear drive ring |
| 479 | Insertion gear ring |
| 480 | Flag holder |
| 481 | Insertion mechanism flag |
| 482 | Insertion mechanism drive motor |
| 483 | Insertion mechanism position sensor |
| 484 | Injection drive plunger |
| 486 | Injection drive motor and gearing |
| 488 | Retaining posts (retaining feature) |
| 490 | Channels for first depth |
| 491 | Lock tabs |
| 492 | Channels for second depth |
| 494 | Abutment wall |
| 496 | Applicator electroporation electrode contacts |
| 700 | Controller Assembly |
| 702 | Handle |
| 704 | Storage bin |
| 706 | Applicator cradle |
| 708 | Applicator connector port |
| 710 | Tray |
| 712 | Display screen |
| 714 | Eject cartridge button |
| 716 | Menu navigation buttons |
| 718 | Mute button |
| 720 | Battery indicator |
| 722 | Power button |
| 724 | USB port |
| 726 | Main power switch |
| 728 | Main power port |
| 750 | Electrical Field Generator |

EXAMPLES

The following examples of the invention are to further illustrate the nature of the invention. It should be understood that the following examples do not limit the invention and the scope of the invention is to be determined by the appended claims.

Example 1: Generation of HBV Core and Pol Antigen Sequences and Plasmid Optimization T-cell epitopes on the hepatitis core protein are considered important for elimination of hepatitis B infection and hepatitis B viral proteins, such as polymerase, may serve to improve the breadth of the response. Thus, hepatitis B core and polymerase proteins were selected as antigens for the design of a therapeutic hepatitis B virus (HBV) vaccine.

Derivation of HBV Core and Polymerase Antigen Consensus Sequences

HBV pol and core antigen consensus sequences were generated based on HBV genotypes B, C, and D. Different HBV sequences were obtained from different sources and aligned separately for core and polymerase proteins. Original sequence alignments for all subtypes (A to H) were subsequently limited to HBV genotypes, B, C, and D. Consensus sequences were defined for each protein alignment in each subtype separately and in all joint BCD sequences. In variable alignment positions, the most frequent amino acid was used in the consensus sequence.

Optimization of HBV Core Antigen

The HBV core antigen consensus sequence was optimized by a deletion in the native viral protein. In particular, a deletion of thirty-four amino acids corresponding to the C-terminal highly positively charged segment was made, which is required for pre-genomic RNA encapsidation.

Optimization of the HBV Pol Antigen

The HBV pol antigen consensus sequence was optimized by changing four residues to remove reverse transcriptase and RNAseH enzymatic activities. In particular, the asparate residues (D) were changed to asparagine residues (N) in the "YXDD" motif of the reverse transcriptase domain to eliminate any coordination function, and thus nucleotide/metal ion binding. Additionally, the first aspartate residue (D) was changed to an asparagine residue (N) and the first glutamate residue (E) was changed to a glutamine residue (A) in the "DEDD" motif of the RNAseH domain to eliminate Mg2+ coordination. Additionally, the sequence of the HBV pol antigen was codon optimized to scramble the internal open reading frames for the envelope proteins, including the S protein and versions of the S protein with the N-terminal extensions pre-S1 and pre-S2. As a result, open reading frames for the envelope proteins (pre-S1, pre-S2, and S protein) and the X protein were removed.

Optimization of HBV Core and Pol Antigen Expression Strategies

Three different strategies were tested to obtain maximum and equal expression of both core and pol antigens from plasmid vectors: (1) fusion of HBV core and pol antigens in frame with a small AGAG inserted between the coding sequences to produce a single Core-Pol fusion protein (FIG. 25A); (2) expression of both core and pol antigens from one plasmid by means of a ribosomal slippage site, particularly the FA2 slippage site from foot-and-mouth disease (FMDV) to produce a biscistronic expression vector expressing individual core and pol proteins from a single mRNA (FIG. 25B); and (3) two separate plasmids encoding for HBV core and pol antigens, respectively (FIG. 25C).

In Vitro Expression Analysis

The coding sequences of consensus HBV core and pol antigens according to each of the above three expression strategies were cloned into the commercially available expression plasmid pcDNA3.1. HEK-293T cells were transfected with the vectors and protein expression was evaluated by Western blot using a HBV core-specific antigen.

Optimization of Post-Transcriptional Regulatory Elements

Four different post-transcriptional regulatory elements were evaluated for enhancement of protein expression by stabilizing the primary transcript, facilitating its nuclear export, and/or improving transcriptional-translational coupling: (1) Woodchuck HBV post-transcriptional regulatory element (WPRE) (GenBank: J04514.1); (2) intron/exon sequence derived from human apolipoprotein A1 precursor (GenBank: X01038.1); (3) untranslated R-U5 domain of the human T-cell leukemia virus type 1 (HTLV-1) long terminal repeat (LTR) (GenBank: KM023768.1); and (4) composite sequence of the HTLV-1 LTR, synthetic rabbit β-globin intron (GenBank: V00882.1), and a splicing enhancer (triple composite sequence). The enhancer sequences were introduced between a CMV promoter and the HBV antigen coding sequences in the plasmids. No significant difference was observed by Western blot in the expression of the core antigen when expressed from a plasmid in the presence and absence of the WPRE element (FIG. 25D). However, when core antigen expression in HEK293T transfected cells from plasmids having the other three post-transcriptional regulatory sequences was evaluated by Western blot, the triple enhancer sequence resulted in the strongest core antigen expression (FIG. 25E).

Selection of Signal Peptide for Efficient Protein Secretion

Three different signal peptides introduced in frame at the N-terminus of the HBV core antigen were evaluated: (1) Ig heavy chain gamma signal peptide SPIgG (BAA75024.1); (2) the Ig heavy chain epsilon signal peptide SPIgE (AAB59424.1); and (3) the Cystatin S precursor signal peptide SPCS (NP_0018901.1). Signal peptide cleavage sites were optimized in silico for core fusion using the Signal P prediction program. Secretion efficiency was determined by analyzing core protein levels in the supernatant. Western blot analysis of core antigen secretion using the three different signal peptides fused at the N-terminus demonstrated that the Cystatin S signal peptide resulted in the most efficient protein secretion (FIG. 25F).

DNA Vaccine Vector Optimization

The optimized expression cassettes containing the triple composite enhancer sequence upstream of the HBV antigen coding sequence with an N-terminal Cystatin S signal peptide sequence were cloned in the DNA vaccine vector pVax-1 (Life Technologies, Thermo Fisher Scientific, Waltham, Mass.). The expression cassette in pVax-1 contains a human CMV-IE promoter followed by the bovine growth hormone (BGH)-derived polyadenylation sequence (pA). Bacterial propagation is driven by the pUC ori replicon and kanamycin resistance gene (Kan R) driven by a small eukaryotic promoter. The pUC ori replication, KanR expression cassette, and expression cassette driven by the CMV-IE promoter are all in the same orientation within the plasmid backbone. However, a marked reduction in core antigen expression was observed in the pVax-1 vector as compared to the expression level observed in the pcDNA3.1 vector.

Several strategies were employed to improve protein expression: (1) reversal of the entire pUCori-KanR cassette into counterclockwise orientation (pVD-core); and (2) changing the codon usage of the KanR gene along with replacement of the Kan promoter with the Amp promoter from the pcDNA3.1 vector (pDK-core). Both strategies restore core antigen expression, but core antigen expression was highest with the pDK vector, which contained the codon-adjusted Kan R gene, AmpR promotor (instead of KanR promoter), and inverse orientation of the pUCori-KanR cassette.

The four different HBV core/pol antigen optimized expression cassettes as shown in FIG. 25G were introduced into the pDK plasmid backbone to test each of the three expression strategies illustrated in FIGS. 25A-25C. The plasmids were tested in vitro for core and pol antigen expression by Western blot analysis using core and pol specific antibodies. The most consistent expression profile for cellular and secreted core and pol antigens was achieved when the core and pol antigens were encoded by separate vectors, namely the individual DNA vectors pDK-core and pDK-pol (FIG. 25H). A schematic representation of the pDK-pol and pDK-core vectors is shown in FIGS. 26A and 26B, respectively.

Example 2. Electroporation Mediated Intramuscular Administration of Nucleic Acid Based Biopharmaceuticals with TriGrid Delivery System (TDS-IM) Device The intracellular delivery of nucleic acid sequences in the skeletal muscle of the upper or lower limb in a subject can be enhanced with the use of an exemplary device, e.g. TriGrid Delivery System (TDS-IM) model II, as provided herein. In some embodiments, the TDS-IM device is used in conjunction with agents approved for investigational use with the TDS-IM device. In an exemplary embodiment, the approved agent is nucleic acids, i.e., DNA or RNA. In some embodiments, the use of TDS-IM device is restricted to a subject in need thereof. In some embodiments, the use of TDS-IM device is restricted to a subject enrolled in an open clinical trial of electroporation mediated intramuscular nucleic acid delivery.

To start up the system for administration, the main power of the device is connected to the stimulator and the system battery is adequately charged for use. The main power switch is turned on and the front panel power button is depressed. The applicator is connected to the applicator connector. Proper connection of the applicator is confirmed by the illumination of the applicator power indicator. The start screen appears once the system completes all self-checks. The OK button is pressed to proceed with the procedure administration.

To insert a syringe into a TDS cartridge, the syringe cap is removed from the syringe, and the syringe flange is aligned with the TDS cartridge syringe loading port. The syringe should snap into place and be fully seated in the TDS cartridge. Once the syringe is loaded, the OK button is pressed on the pulse stimulator to continue. The cartridge cap should remain affixed to the cartridge until the cartridge is loaded into the applicator.

To insert the syringe loaded cartridge into the applicator, the cartridge is aligned with the applicator with the cartridge syringe loading port facing upward. When the cartridge is inserted into the applicator, and the cartridge is automatically drawn into its fully loaded position in the applicator. Successful loading of the cartridge is indicated in the stimulator. Once the cartridge is loaded, the applicator is returned to its cradle, and an appropriate injection site on the subject is selected. In some embodiments, the injection site for intramuscular nucleic acid delivery is medial deltoid muscle at approximately three finger widths below the edge of acromion process (shoulder bone). In an exemplary embodiment, the injection depth at medial deltoid is about 0.75"-1.25" (19-30 mm). In some embodiments, the injection site for intramuscular nucleic acid delivery is vastus lateralis muscle (outer thigh) at approximately the midpoint between the hip and the knee. In an exemplary embodiment, the injection depth at vastus lateralis is about 1.0"-1.5" (25-38 mm). Once the injection site is selected, the applicator depth selection button followed by the injection depth selection button corresponding to the injection site/depth are pressed. In some embodiments, the injection depth selection indicator turns to solid illumination, confirming the selected injection depth. In some embodiments, the depth selection button on the right side corresponds to a deeper injection depth. In an embodiment, wherein the initially selected injection site is to be changed, the selection button corresponding to the other injection depth is pressed, and the other injection depth is selected when the select injection depth screen returns.

To start administration of an approved agent via TDS-IM device to the subject, the cartridge cap is removed and discarded. The device is aligned with and firmly pressed against the target injection site. When the device is firmly pressed against the target injection site, all four bars of the applicator placement indicator illuminates, and the procedure countdown timer illuminates with "8" seconds, indicating the time remaining in the administration procedure. The applicator trigger is depressed for the agent to be administered while the pressure is consistently maintained. When the procedure countdown timer reaches "0," the electrical stimulation is delivered. Once the administration procedure is completed, the procedure complete indicator illuminates, and the device can be withdrawn from the injection site. The device may not be withdrawn from the injection site until the procedure is completed or a procedure fault indicator illuminates. In some embodiments, wherein the device detects a problem during the administration procedure, the device aborts the administration procedure and illuminates the procedure fault indicator. In an exemplary embodiment, wherein the device aborts the administration procedure and the device promptly is removed from the subject, the stimulator display of the device provides further instructions.

To eject the cartridge from the applicator after completion of the agent administration to the subject in need thereof, the eject button located on the stimulator is depressed. The applicator automatically advances the cartridge to the position where it can be manually removed from the applicator. Once the cartridge stops moving, the sides of the cartridge as indicated by arrows can be grasped for pulling the cartridge out of the applicator. After the cartridge is removed, completion of the full injection can be verified by inspecting the syringe plunger position. To turn off the device, the applicator is placed in the holster, and the front panel power button is pressed for 5 seconds.

Example 3. TDS-IM Electroporation to Mouse and Non-Human Primate

TriGrid Delivery System-Intramuscular (TDS-IM) electroporation technology is used to enhance the delivery of DNA-based constructs in muscle tissue. The TriGrid electrode array for intramuscular (IM) delivery is comprised of four electrodes arranged in two equilateral triangles to form a diamond shape surrounding a central injection needle (FIG. 22). Integration of the agent delivery and the electric field propagation into a single device assures that induction of the electroporation effect occurs at the site of agent distribution and allows injection of the plasmid construct and application of the electric pulses in a single step. In this manner, IM delivery of plasmid DNA is achieved in an effective and reproducible manner.

The TriGrid electrode arrays for each animal model are scaled to efficiently deliver the DNA plasmids, such as those made in Example 1, to the selected muscle regardless of size and overlying tissue characteristics. The primary electroporation device parameters that are scaled for use in each animal model are the TriGrid size (i.e., electrode spacing), applied voltage (250 V/cm where cm is the TriGrid size), electrode diameter, and the electrode penetration depth. Secondary adaptations to the device include variation in syringe volume, plasmid DNA volume, and hypodermic needle gauge/length.

The mouse studies were performed with a TDS-IM v1.0 device using an electrode array with a 2.5 mm spacing between the electrodes. This adjustment in electrode array size is to accommodate the smaller size of the mouse muscle. FIG. 23A depicts a TDS-IM v1.0 TriGrid version adapted for use in the mouse model. The non-GLP monkey studies were also performed with a TDS-IM v1.0 device, but with a 6 mm electrode array spacing. FIG. 23B depicts a TDS-IM v1.0 TriGrid version adapted for use in the non-human primate (NHP) model.

The device used in the GLP monkey study was a TDS-IM v2.0 device, which is also intended for human clinical study. This device has a 6 mm electrode spacing and the same activation conditions as the TDS-IM v1.0 device. The electrode materials of the TDS-IM v2.0 device are identical with the TDS-IM v1.0 device used in the NHP study described above, but the Cartridge support structure and syringe used for administration are different. Also, the insertion depth for humans and non-human primates is different. Therefore, the TDS-IM v2.0 device was fitted with a spacer in order to adapt the TDS-IM v2.0 device for use in the much smaller NHP muscles. FIG. 24 depicts the TDS-IM v2.0 TriGrid version adapted for use in the non-human primate (NHP) model.

In each animal study, the animals were anesthetized to immobilize them prior to the electroporation procedure administration. The administration site was located using regional bony anatomical landmarks as reference points and the hair was removed over the selected site with an electric hair clipper followed by an aseptic swab. The TDS-IM array was inserted percutaneously into the selected muscle with the major axis of the diamond configuration oriented in parallel with the muscle fibers. Following electrode insertion, the injection was initiated to distribute the DNA in the muscle. Following completion of the IM injection, a 250 V/cm electrical field was locally applied for a total duration of 400 ms at a 10% duty cycle (i.e., voltage is actively applied for a total of 40 ms of the 400 ms duration). Once the electroporation procedure was completed, the TriGrid™ array was removed and the animals were recovered. The variable components for each TDS-IM version and/or animal model are as follows in Table 1 and Table 2.

TABLE 1

TDS-IM version and TriGrid details

| TDS-IM Version | Animal Model | TriGrid size (mm) | Electrode diameter (in) | Conductive length (mm) | Effective Penetration depth (mm) | DNA Injection Volume (cc) | Syringe Volume (cc) | Injection needle gauge | Injection method |
| --- | --- | --- | --- | --- | --- | --- | --- | --- | --- |
| TDS-IM v1.0 | mouse | 2.5 | 0.030 | 3.2 | 3.2 | 0.020 | 3/10 cc | 30 | manual |

TABLE 1-continued

TDS-IM version and TriGrid details

| TDS-IM Version | Animal Model | TriGrid size (mm) | Electrode diameter (in) | Conductive length (mm) | Effective Penetration depth (mm) | DNA Injection Volume (cc) | Syringe Volume (cc) | Injection needle gauge | Injection method |
|---|---|---|---|---|---|---|---|---|---|
| TDS-IM v1.0 | NHP | 6.0 | 0.021 | 5.0 | 15.5 | 1.0 | 1.0 cc | 22 | automated |
| TDS-IM v2.0 | NHP | 6.0 | 0.023 | 5.0 | 9.0* | 1.0 | 1.0 cc | 22 | automated |

*NHP body weight and muscle size required a shorter penetration depth; a 10 mm depth limiter was used to shorten the penetration depth to 9 mm.

TABLE 2

TDS-IM version and Pulse Stimulator details

| TDS-IM Version | Animal Model | Applied electric field (V/cm) | Applied Voltage range (V) | Applied Current limits (A) | Applied current limit (A/sec) | Total pulse number | Active stimulation duration (ms) | Maximum sequence duration (ms) |
|---|---|---|---|---|---|---|---|---|
| TDS-IM v1.0 | mouse | 250 | 59.4-65.6 | N/A*-4 | 0.16 | 6 | 40.8 | 369.3 |
| TDS-IM v1.0 | NHP | 250 | 142.4-157.6 | 0.6-4 | 0.16 | 6 | 40.8 | 369.3 |
| TDS-IM v2.0 | NHP | 250 | 142.4-157.6 | 0.6-4 | 0.16 | 6 | 40.8 | 369.3 |

*low current limit disabled to accommodate mouse model characteristics

Example 4. TDS-IM Electroporation to Human

A TDS-IM v2.0 device is used in the clinical study. The device which is essential the same as that used for the GLP monkey. The insertion depth for humans and non-human primates is different. Therefore, the TDS-IM v2.0 device was fitted with a spacer in order to adapt the TDS-IM v2.0 device for use in the much smaller NHP muscles. The stimulation conditions were essentially the same as those used for GLP monkeys, with the exception that the penetration depth about 19 mm, instead of 9 mm as in the GLP monkeys.

While preferred embodiments of the disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments described herein, or combinations of one or more of these embodiments or aspects described therein can be employed in practicing the disclosure. It is intended that the following claims define the scope of the disclosure and that methods and structures within the scope of these claims and their equivalents be covered thereby.

The invention claimed is:

1. An apparatus for a controlled delivery of an HBV vaccine to a predetermined tissue site within a subject in need thereof, comprising:
a cartridge assembly comprising an outer cartridge, an inner cartridge, and a reservoir containing the HBV vaccine, wherein a reservoir containment volume is contained within the outer cartridge and configured to receive the reservoir;
a needle hub operatively connected to at least one injection orifice through which the HBV vaccine is capable of being administered;
a reservoir detection cap configured to engage with the reservoir upon insertion into the reservoir containment volume;
an applicator comprising a cartridge assembly receiving volume, and an insertion detector, wherein the insertion detector is configured to sense a position of the reservoir detection cap;
a plurality of penetrating electrodes arranged with a predetermined spatial relationship relative to the at least one injection orifice;
an electrical field generator for generating an electrical signal operatively connected to the plurality of penetrating electrodes; and
a controlled source of energy sufficient to transfer a predetermined amount of the HBV vaccine at a predetermined rate from the reservoir through the at least one injection orifice to the predetermined tissue site within the subject,
wherein the HBV vaccine comprises:
a nucleic acid molecule comprising a polynucleotide encoding an HBV polymerase antigen, wherein the HBV polymerase antigen comprises an amino acid sequence that is at least 98% identical to SEQ ID NO: 4 and wherein the HBV polymerase antigen does not have reverse transcriptase activity and RNAse H activity;
and
a pharmaceutically acceptable carrier.

2. The apparatus of claim 1, wherein the reservoir detection cap is mounted in a breech mechanism operatively connected to a reservoir interlock comprising a tab extending through the inner cartridge and into the reservoir containment volume, wherein the tab is configured to be moved from a first position to a second position by the reservoir after the reservoir has been seated within the reservoir containment volume, thereby allowing the breech mechanism and the reservoir detection cap to slidably engage the reservoir.

3. The apparatus of claim 2, wherein the apparatus further comprises a force interlock, which is configured to sense a force applied against the predetermined tissue site of the subject and is configured to prevent administration of the HBV vaccine to the subject when insufficient force is provided.

4. The apparatus of claim 1, wherein the apparatus further comprises at least one sensor.

5. The apparatus of claim 4, wherein the at least one sensor is configured to detect a reservoir label and is further configured to verify the presence of the reservoir containing HBV vaccine.

6. The apparatus claim 1, wherein the HBV vaccine is capable of inducing an immune response in a mammal against at least two HBV genotypes, and wherein the nucleic acid molecule is present in a plasmid DNA vector.

7. The apparatus of claim 6, wherein the HBV vaccine comprises: the plasmid DNA vector, which comprises, from 3'-end to 5'-end, a promoter sequence comprising the polynucleotide sequence of SEQ ID NO: 7, an enhancer sequence comprising the polynucleotide sequence of SEQ ID NO: 8, a signal peptide coding sequence comprising the polynucleotide sequence of SEQ ID NO: 5, the polynucleotide encoding the HBV polymerase antigen comprising the polynucleotide sequence of SEQ ID NO: 3, and a polyadenylation signal sequence comprising the polynucleotide sequence of SEQ ID NO: 11; and the pharmaceutically acceptable carrier, wherein the plasmid DNA vector further comprises a kanamycin resistance gene having the polynucleotide sequence of SEQ ID NO: 12, and an origin of replication having the polynucleotide sequence of SEQ ID NO: 10.

8. The apparatus of claim 1, wherein the insertion detector is configured to detect a visible line of sight through a set of reservoir locking holes, or occlusion of the set of reservoir locking holes.

9. The apparatus of claim 8, further comprising an IR or visible light emitter paired with the insertion detector.

10. The apparatus of claim 1, which further comprises a needle comprising an asymmetrical bevel and a mounting feature for the needle hub, wherein the mounting feature for the needle hub is on the inner cartridge and the mounting feature is capable of offsetting a position of an injection orifice of the needle relative to the plurality of penetrating electrodes prior to deployment to account for expected deployment characteristics of the asymmetrical bevel of the needle.

11. The apparatus of claim 1, further comprising a controller and a force contact circuit, wherein a feedback loop exists between the controller and the force contact circuit such that upon insertion of the plurality of penetrating electrodes in the predetermined tissue site, detection of a change in an applied force is configured to prompt initiation of a check as to whether the plurality of penetrating electrodes remain properly deployed in the predetermined tissue site.

12. A method of inducing an immune response against an HBV infection in a subject in need thereof, comprising delivering a HBV vaccine to a predetermined tissue site within the subject using the apparatus of claim 1.

13. The method of claim 12, wherein the predetermined tissue site is located in a skeletal muscle of the subject.

14. The method of claim 13, wherein the skeletal muscle of the subject is medial deltoid muscle or vastus lateralis.

15. The method of claim 12, wherein an electrical signal operably connected to the plurality of penetrating electrodes comprises an electrical field strength of 100 V/cm to 400 V/cm; has a voltage of 50 to 200 V; and a current of 0.5 to 5 A/sec.

16. A method of treating an HBV-induced disease in a subject in need thereof, comprising delivering a HBV vaccine to a predetermined tissue site within the subject using the apparatus of claim 1, wherein the HBV-induced disease is selected from the group consisting of advanced fibrosis, cirrhosis and hepatocellular carcinoma (HCC).

17. An apparatus for a controlled delivery of an HBV vaccine to a predetermined tissue site within a subject comprising:

- a cartridge assembly comprising an outer housing, an inner cartridge, and a reservoir containing the HBV vaccine, wherein a reservoir containment volume is contained within the outer housing and configured to receive the reservoir;
- a needle hub operatively connected to at least one injection orifice through which the HBV vaccine is capable of being administered;
- a reservoir detection cap configured to engage with the reservoir upon insertion into the reservoir containment volume;
- an applicator comprising a cartridge assembly receiving volume, and an insertion detector, wherein the insertion detector is configured to sense a position of the reservoir detection cap;
- a plurality of penetrating electrodes arranged with a predetermined spatial relationship relative to the at least one injection orifice;
- an electrode support structure comprising a hole and a wall, wherein the electrode support structure prevents inadvertent perpendicular motion of the electrodes;
- an electrical field generator for generating an electrical signal operatively connected to the plurality of penetrating electrodes; and
- a controlled source of energy sufficient to transfer a predetermined amount of the HBV vaccine at a predetermined rate from the reservoir through the at least one injection orifice to the predetermined tissue site within the subject, wherein the HBV vaccine comprises:

- a nucleic acid molecule comprising a polynucleotide encoding an HBV polymerase antigen, wherein the HBV polymerase antigen comprises an amino acid sequence that is at least 98% identical to SEQ ID NO: 4 and wherein the HBV polymerase antigen does not have reverse transcriptase activity and RNAse H activity;

and

- a pharmaceutically acceptable carrier.

18. The apparatus of claim 17, wherein the electrode support structure is capable of providing an operative connection between a conductive contact region located on a distal region of the plurality of penetrating electrodes and the controlled source of energy when the plurality of penetrating electrodes are deployed into the predetermined tissue site within the subject.

19. The apparatus of claim 17, wherein the electrode support structure is a planar support structure positioned perpendicularly relative to the elongate orientation of the electrodes, the planar support structure comprising at least one aperture configured to allow passage of the electrode through the predetermined tissue site.

20. The apparatus of claim 17, wherein the electrode support structure is an adaptive electrode support, wherein the adaptive electrode support structure is a compression spring.

21. The apparatus of claim 17, wherein the electrode support structure further comprises at least one of a telescoping tube, and a stick shield spring, and at least one lateral support member attached to the plurality of penetrating electrodes with at least one optional hinge feature.

22. A method of inducing an immune response against an HBV infection in a subject in need thereof, comprising delivering a HBV vaccine to a predetermined tissue site within the subject using the apparatus of claim 17.

23. A method of treating an HBV-induced disease in a subject in need thereof, comprising delivering a HBV vaccine to a predetermined tissue site within the subject using the apparatus of claim 17, wherein the HBV-induced disease is selected from the group consisting of advanced fibrosis, cirrhosis and hepatocellular carcinoma (HCC).

\* \* \* \* \*